US006706522B1

(12) United States Patent
Blattner et al.

(10) Patent No.: US 6,706,522 B1
(45) Date of Patent: Mar. 16, 2004

(54) PLASMID DNA FROM *YERSINIA PESTIS*

(75) Inventors: Frederick R. Blattner, Madison, WI (US); Valerie Burland, Cross Plains, WI (US); Debra J. Rose, Fond du Lac, WI (US); George F. Mayhew, Madison, WI (US); Nicole Perna, Madison, WI (US); Robert D Perry, Lexington, KY (US); Susan C Straley, Lexington, KY (US); Jacqueline D. Fetherston, Lexington, KY (US); Luther E. Lindler, Wheaton, MD (US); Gregory V. Plano, Miami, FL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/409,800

(22) Filed: Sep. 30, 1999

(51) Int. Cl.[7] .................................... C12N 15/63

(52) U.S. Cl. ........................ 435/320.1; 435/252.3; 536/23.1

(58) Field of Search .................. 536/23.1; 435/320.1, 435/252.3

(56) References Cited

PUBLICATIONS

GenBank Accession AJ001708, Version AJ001708.1, GI: 2660511, Oct. 1997.*

Rakin et al. (Microbiology (Dec. 1996) 142 (Pt 12) 3415–24).*

Yu et al. (Journal of Bacteriology, Oct. 1998, p. 5192–5202).*

GenBank Accession AF053945, version 1, Oct. 6, 1998, accessed Dec. 4, 2001.*

Altscul et al., "Gapped BLAST and PSI–BLAST: a new generation of protein database search programs," *Nucleic Acids Research* 25:3389–3402 (1997).

Bercovier, et al., "Intra– and Interspecies Relatedness of *Yersinia pestis* by DNA Hybridization and its Relationship to *Yersinia pseudotuberculosis,*" *Current Microbiology* 4:225–229 (1980).

Birnboim et al., "A rapid alkaline extraction procedure for screening recombinant plasmid DNA," *Nucleic Acids Research* 7:1513–1523 (1979).

Borodovsky et al., "Genmark: Parallel Gene Recognition for Both DNA Strands," *Computers Chem.* 17:123–133 (1993).

Brubaker, Robert R., "Factors Promoting Acute and Chronic Diseases Caused by Yersiniae," *Clinical Microbiology Reviews* 4:309–324 (1991).

Drozdov et al., "Virulent non–capsulate *Yersinia pestis* variants constructed by insertion mutagenesis," *J. Med. Microbiol.* 42:264–268 (1995).

Du et al., "Genetic Analysis of Virulence Determinants Unique to *Yersinia pestis,*" *Yersiniosis: Present and Future* 13:321–324 (1995).

Ferber et al., "Plasmids in *Yersinia pestis,*" *Infection and Immunity* 31:839–841 (1981).

Fetherston et al., "The pigmentation locus of *Yersinia pestis* KIM6+ is flanked by an insertion sequence and includes the structural genes for pesticin sensitivity and HMWP2," *Molecular Microbiology* 13:697–708 (1994).

Filippov et al., "Plasmid content in *Yersinia pestis* stains of different origin," *FEMS Microbiology Letters* 67:45–48 (1990).

Forsberg et al., "The virulence protein Yop5 of *Yersinia pseudotuberculosis* is regulated at transcriptional level by plasmid–plB1–encoded trans–acting elements controlled by temperature and calcium," *Molecular Microbiology* 2:121–133 (1988).

Forsberg et al., "Genetic Analysis of the yopE Region of Yersinia spp.: Identification of a Novel Conserved Locus, yerA, Regulating yopE Expression," *Journal of Bacteriology* 172:1547–1555 (1990).

Galyov et al., "Nucleotide sequence of the *Yersinia pestis* gene encoding F1 antigen and the primary structure of the protein," *FEBS* 277:230–232 (1990).

Galyov et al., "Expression of the envelope antigen F1 of *Yersinia pestis* is mediated by the product of caf1M gene having homology with the chaperone protein PapD of *Escherichia coli,*" *FEBS* 286:79–82 (1991).

Humphreys, et al., "A simple Method for the Preparation of large Quantities of Pure Plasmid DNA," *Biochimica etBiophysics Acta*, 383:457–463 (1975).

Karlyshev et al., "Caf1R gene and its role in the regulation of capsule formation of Y. pestis," *FEBS* 305:37–40 (1992).

Lipman et al., "A tool for multiple sequence alignment," *Proc. Natl. Acad. Sci. USA* 86:4412–4415 (1989).

Miller et al., "Nucleotide Sequence of the *Yersinia enterocolitica* aid Gene and Characterization of the Ail Protein Product," *Journal of Bacteriology* 172:1062–1069 (1990).

Moore et al., "Hybridization of Deoxyribonucleotide Sequence of *Yersinia enterocolitica* and Other Selected Members of Enterobacteriaceae," *International Journal of Systematic Bacteriology* 25:336–339 (1975).

Nakai et al., "Expert System for Predicting Protein Localization Sites in Gram–Negative Bacteria," *Proteins: Structure, Function, and Genetics* 11:95–110 (1991).

Perry et al., "Identification and Cloning of a Hemin Storage Locus Involved in the Pigmentation Phenotype of *Yersinia pestis,*" *Journal of Bacteriology* 172:5929–5937 (1990).

(List continued on next page.)

*Primary Examiner*—Jeffrey Fredman
*Assistant Examiner*—Juliet C. Switzer
(74) *Attorney, Agent, or Firm*—Quarles & Brady LLP

(57) ABSTRACT

The complete DNA sequence of three plasmids from the bacterium *Yersinia pestis*, the causative agent for bubonic plague, have been determined and are set forth. The open reading frames, or protein coding regions, of the plasmids have been determined. The DNA sequence and ORF information is useful for the creation of diagnostic, prophylactic and therapeutic tools for combating the disease caused by this agent.

2 Claims, 2 Drawing Sheets

OTHER PUBLICATIONS

Portnoy, et al., "Characterization of Common Virulence Plasmids in Yersinia Species and Their Role in the Expression of Outer Membrane Proteins," *Infection and Immunity* 43:108–114 (1984).

Portnoy et al., "Role of a Plasmid in the Pathogenicity of Yersinia Species," *Current Topics in Microbiology and Immunology* 118:29–51 (1985).

Protsenko et al., "Detection and Characterization of *Yersinia pestis* Plasmids Determining Pesticin I, Fraction I Antigen, and "Mouse" Toxin Synthesis" *Genetika* 19:838–846 (1984).

Protsenko et al., "Integration of the plasmid encoding the synthesis of capsular antigen and murine toxin into *Yersinia pestis* chromosome," *Microbial Pathogenesis* 11:123–138 (1991).

Rakin et al., "Virulence–associated fyuA/irp2 gene cluster of *Yersinia enterocolitica* biotype 1B carries a novel insertion sequence IS1328," *FEMS Microbiology Letters* 129:287–282 (1995).

Samoilova et al., "Virulence of pPst+ and pPst– strains of *Yersinia pestis* for guinea–pigs," *Bacterial Pathogenicity* 440–444 (1996).

Smith et al., "The ancestral IncP replication system consisted of contiguous oriV and trfA segments as deduced from a comparison of the nucleotide sequences of diverse IncP plasmids," *Journal of General Microbiology* 139:1761–1766 (1993).

Straley et al., "Cytoplasmic and membrane proteins of yersiniae cultivated under conditions simulating mammalian intracellular environment," *Proc. Natl. Acad. Sci. USA* 78:1224–1228 (1981).

Straley, Susan C., "The Plasmid–Encoded Outer–Membrane Proteins of *Yersinia pestis," Reviews of Infectious Diseases* 10:S323–S326 (1988).

Straley, Susan C., "The low–$Ca^{2+}$ response virulence regulon of human–pathogenic yersiniae," *Microbial Pathogenesis* 10:87–91 (1991).

Welkos et al., "Studies on the Contribution of the F1 Capsule–Associated Plasmid pFra to the Virulence of *Yersinia pestis," Yersiniosis: Present and Future* 13:299–305 (1995).

Winans et al., "Genetic Localization and Characterization of a pKM101–Coded Endonuclease," *Journal of Bacteriology* 154:1117–1125 (1983).

* cited by examiner

PLASMID DNA FROM *YERSINIA PESTIS*

STATEMENT REGARDING FEDERALLY SPONSORED RESEARCH OR DEVELOPMENT

This invention was made with United States government support awarded by NIH Grant No. HG01428, Subcontract No. 144 FH33. The U.S. government has certain rights in this invention.

CROSS-REFERENCE TO RELATED APPLICATIONS

Not applicable.

BACKGROUND OF THE INVENTION

Over the centuries, the bubonic plague (also known as the Black Death) has claimed the lives of millions of people. The disease is characterized by chills, fever, vomiting, diarrhea, painful swollen lymph nodes (buboes), blackening of the skin caused by ruptured blood vessels, and a very high mortality rate (up to 75% if left untreated). Treatment with antibiotics in the early stages of the infection is generally effective.

Bubonic plague is caused by the bacterium *Yersinia pestis*, which is transmitted to humans from rats or other rodents by fleas that feed on infected rodents and then bite humans. Reservoirs of the bacteria persist today, and attempts to eliminate wild rodent plague have proven ineffective. Occasional outbreaks of the deadly disease continue to occur, particularly in small towns, villages, and rural areas in developing countries.

While bacteria carry genetic material in their chromosomes, bacteria also often carry genetic material in loops of DNA called plasmids. Bacterial plasmids are nonessential, extrachromosomal genetic elements capable of autonomous replication. The genetic material in plasmids often encodes functions required for maintenance of the plasmid in its bacterial host and sometimes encodes optional functions that promote survival of the bacterial host under certain environmental conditions. Pathogenicity determinants are commonly plasmid-encoded, and fall within the category of optional plasmid-encoded functions.

*Yersinia pestis* is a facultative intracellular parasite which harbors at least three different plasmids, designated pCD1, pPCP1, and pMT1, which are necessary for full virulence of the organism. One of the plasmids, designated pCD1, is also found in the enteropathogenic species *Yersinia pseudotuberculosis* and *Yersinia enterocolitica* (Ferber, et al. *Infect. Immun*. 31:839–841, 1981; Portnoy, et al. *Curr. Topics Microbiol. Immunol*. 118:29–51, 1985), whereas pMT1 and pPCP1 are unique to *Y. pestis* (Brubaker. *Clinical Microbiol Rev*. 4:309–324, 1991). Plasmids pMT1 and pPCP1 are thought to promote deep tissue penetration by *Y. pestis* and to contribute to the acute infection associated with this species. The *Y. pestis* genome shares much homology with that of *Y. pseudotuberculosis*, (Bercovier, et al. *Curr. Microbiol*. 4:225–229, 1980; Moore, et al. *Inter. J. Sys. Bacteriol*. 25:336–339, 1975), yet the infection caused by the latter organism is usually mild and self limiting (Butler, Plague and other yersinia infections, p. 111–159. In W. B. Greenbugh III and T. C. Merigan (eds.), Current topics in infectious disease, Plenum Press, New York, N.Y., 1983).

An understanding of the differences in the pathogenesis of *Y. pestis* and *Y. pseudotuberculosis* may be afforded by comparing polynucleotide sequences or genes found on pMT1 or pPCP1 plasmids, and which are unique to *Y. pestis*. It has been found that *Y. pestis* strains lacking the pCD1 plasmid are completely avirulent. Therefore, determination of the complete pCD1 sequence may provide important information about the role of the plasmid in virulence in various pathogenic yersiniae.

The 9.5 kb plasmid pPCP1 encodes a bacteriocin termed pesticin, a pesticin immunity protein and a plasminogen activator activity. Loss of this plasmid increases the $LD_{50}$ of the organism by a factor of one hundred thousand, as measured by subcutaneous injection in the mouse model. (Sodeinde, et al. *Science* 258:1004–1007, 1992).

The second plasmid unique to *Yersinia pestis*, designated pMT1, is a 100 kb plasmid that encodes the capsular protein Fraction 1 and the murine toxin (Protsenko, et al. *Genetika* 19:1081–1090, 1983). The genes for the capsular proteins have been cloned and sequenced using *Y. pestis* strain EV76 (Galyov, et al. *FEBS Lett*. 277:230–232, 1990; Galyov, et al. 286:79–82, 199.1; Karlyshev et al. *FEBS Lett*. 305:37–40, 1992). The role of these proteins in plague pathogenesis has not been unequivocally determined, and the effect of mutational loss of these proteins on the $LD_{50}$ varies, depending on the animal model and route of infection (Brubaker *Curr. Top. Microbiol*. 57:111–118, 1972; Brubaker Rev. Infect. Diis. 5: S748-S758, 1983). However, pMT1 does appear to contribute to the acute phase of plague infection, as evidenced by a reduced morbidity associated with infection by strains lacking pMT1 (Drozdov, et al. *J. Med. Microbiol*. 42:264–268, 1995; Samoilova, et al. *J. Med. Microbiol*. 45:44.0–444, 1996;Welkos, et al. *Contrib. Microbiol. Immunol*. 13:229–305, 1995).

Information pertaining to the genetic characterization of the pMT1 molecule is limited. The size of the plasmid has been found to vary, either from variations in the versions of the plasmids or in technique to measure the plasmids, from 90 kb to 288 kb (Filippov, et al. *FEMS Microbiol. Lett*. 67:45–48, 1990). It is known that pMT1 is an integrative plasmid capable of integrating into *Y. pestis* chromosome with high frequency and at multiple sites, with integration likely resulting from IS100 homology between the plasmid and chromosome (Protsenko, et al. *Microbiol. Pathogen* 11:123–128, 1991).

Previous characterization of pMT1 has identified five genes that may be involved in the synthesis of murine toxin (MT) and F1 capsule antigen, both known virulence factors. Expression of both the capsular protein and murine toxin genes has been characterized with respect to environmental cues (e.g., temperature and-calcium) (Du, et al. *Contrib. Microbial. Immunol*. 13:321–324, 1995). F1 capsule synthesis is maximal at 37° C. in the absence of extracellular calcium, conditions similar to those that induce expression of a major *Y. pestis* virulence determinant (Straley *Rev. Infect. Dis*. 10:S323–S326, 1988; Straley *Microbial. Pathoaen* 10:87–89, 1991; Straley et al. *Proc. Natl. Acad. Sci. USA* 78:1224–1228, 1981). Murine toxin expression is induced at 26° C., conditions similar to those that would be expected to occur in the flea vector. The occurrence of plasmid genes that are induced under widely different conditions suggests regulation of *Y. pestis* virulence determinant expression by at least two networks.

The plasmid pCD1 is found in *Y. pestis*, as well as in certain other pathogenic Yersinia species, including *Y. pseudotuberculosis* and *Y. enterocolitica*. The plasmid encodes a complex virulence property called the low-$Ca^{2+}$ response (LCR). The LCR was discovered in *Y. pestis* growing in vitro, where the bacteria respond to the absence of $Ca^{2+}$ at 37° C. by the strong expression and secretion of a virulence protein called V antigen, or LcrV. In certain media, expression of LcrV is accompanied by a response termed "restriction," in which the yersiniae undergo an orderly metabolic shutdown and cease growth. Under LCR-inductive conditions, the transcription, translation, and secretion of a set of virulence proteins called Yops (for Yersinia outer proteins) is maximally induced. The operons encoding these and other similarly regulated operons on the LCR plasmid have been referred to as the LCR stimulon (LCRS). Millimolar concentrations of $Ca^{2+}$ permit full growth at 37° C., reduced expression of LcrV and Yops, and essentially no secretion of these proteins. Under ambient temperature conditions outside a mammalian host, the Yops and LcrV proteins are produced at a low, basal level and are not secreted, which suggests that the LCR is designed to function within a mammal. Expression of LCR is apparently modulated by other environmental factors, including $Mg^{2+}$, $Cl^-$, $Na^+$, glutamate, nucleotides, and anaerobiosity. The molecular basis for these effects has not been determined, but these elements of environmental modulation could be important in adjusting virulence protein expression and secretion in response to the wide range of niches that yersiniae are expected to encounter during an infection.

The pCD1 plasmid also encodes a type III secretion system called Ysc (for Yop secretion) that is involved in the secretion of Yops, LcrV, and some regulatory proteins in the LCR. The Ysc system is locally activated by cell contact at the interface between a bacterium and eukaryotic cell. This cell to cell contact causes the opening of the secretion system's inner and outer gates (LcrG and LcrE (or YopN), respectively), thereby allowing secretion of negative regulatory proteins (e.g., LcrQ also called YscM, a key regulatory protein). Secretion of negative regulatory proteins allows full transcriptional activation of LCRS operons by LcrF, an AraC-like activator protein.

Yops are secreted locally, without processing. The secretion mechanism recognizes two signals: one in the first 45 nucleotides of the yop mRNA and one related to a domain that has been found for some Yops to bind a specific Yop chaperone (Syc), also encoded by the LCR plasmid Certain of the Yops (e.g., YopB, YopD, YopK) are involved in targeting effector Yops (YopE, YopH, YpkA, YopM, and possibly YopJ) into the eukaryotic cell. Once inside the cell, the effector Yops act on intracellular target molecules, thereby interfering with cellular signaling and cytoskeletal functions. LcrV acts functions both as a regulatory protein involved in Yop secretion and targeting and as a potent anti-host protein. LcrV is the only LCRS protein that is secreted in large amounts into the surrounding medium by yersiniae in contact with eukaryotic cells. LcrV adversely affects the host organism when administered alone to mice, whereas all other secreted proteins depend on the Ysc machinery of yersiniae, in intimate contact with mammalian cells, for delivery into the mammalian cells.

Expression of the LCR has a profound immunosuppressive effect that results from the interference with innate defenses at the site of infection and the host organism's inability to mobilize an effective cell-mediated immune response. *Y. pestis*, and, in immunocompromised individuals, the enteropathogenic yersiniae grow unchecked in the lymphoid system in a fulminant-disease associated with high mortality, absent appropriate antibiotic treatment. In contrast, yersiniae lacking the LCR plasmid pCD1 are completely avirulent.

Several other important pathogens have virulence systems with many striking similarities to the LCR; however, the LCR is the best characterized of these and remains a prototype for investigations at the forefront of molecular pathogenesis.

A more complete understanding of the role of LCR plasmids may be obtained by determining the entire sequence of an LCR plasmid.

The development of additional sequence information from plasmids of *Y. pestis* is needed for comprehensive efforts in the detection, diagnosis, prophylaxis and treatment of infections caused by the organism.

BRIEF SUMMARY OF THE INVENTION

One aspect of the present invention is an isolated *Yersinia pestis* plasmid pMT1- or pCD1-specific polynucleotide sequence selected from the group consisting of any portions of the sequences present in SEQ ID NO:1 through SEQ ID NO:6 set forth below.

The present invention is in part summarized by the presentation of the complete nucleotide sequence of two plasmids from *Yersinis pestis*, which enables diagnostic, prophylactic and therapeutic tools to be developed for use in combating the pathogen.

The DNA sequences of the present invention may include an open reading frame (ORF), an insertion sequence element, or a plasmid maintenance function, for example.

It is an object of the invention to provide essentially the entire sequence of pMT1 and pCD1 from *Yersinia pestis* KIM5 to allow methods of detecting, diagnosing, preventing, and treating infections with *Yersinia pestis.*

Other object, advantages and features of the present invention will become apparent from the following specification when taken in conjunction with the following drawings.

DETAILED DESCRIPTION OF THE INVENTION

Figure 1:
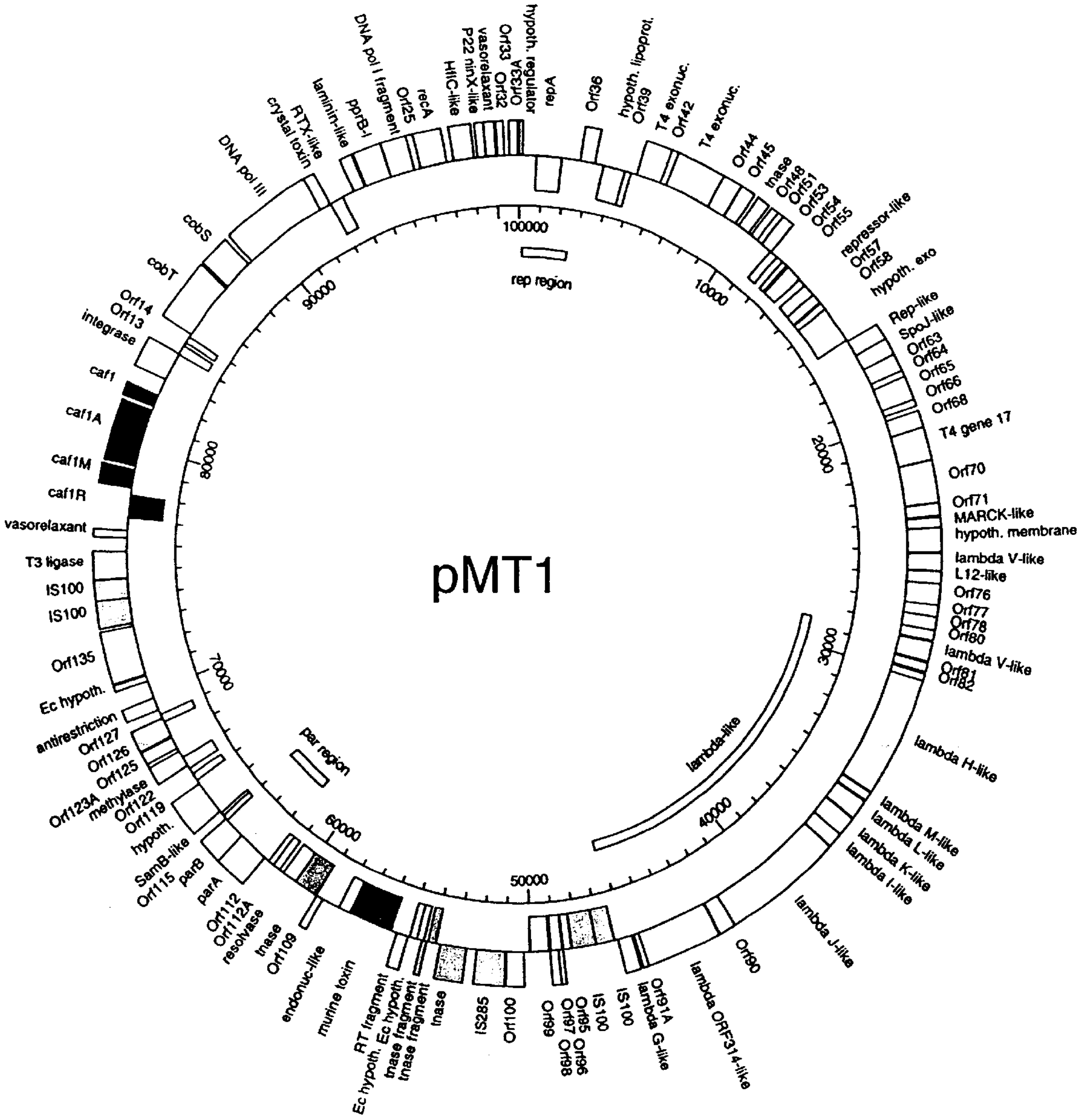
FIG. 1 is a plasmid map of the plasmid pMT1, showing in schematic fashion the relative positions of notable features of the plasmid.

This specification describes the complete DNA sequencing of the plasmids, pPCP1, pMT1 and pCD1 from *Yersinia pestis*, all of which are associated with the pathogenicity of the organism. Presented below is both the complete DNA sequence of the plasmids as well as tables listing the open reading frames (ORFs) of the plasmids, indicating which portions of the plasmid DNA encodes the production of proteins. Some other important regions of the plasmid DNA, such-as the integration sequences (IS) are also indicated. With the information provided by this complete DNA sequence information, several things become possible. It now becomes possible to design and implement nucleotide-sequence based diagnostic tools to diagnose and identify virulent strains of *Yersinia pestis* in a biological sample based on the presence of DNA sequence in such a sample. The identification of the ORFs contained in the plasmids makes possible the comprehensive identification and characterization of the toxins and other proteins encoded by the plasmids thereby enabling the ability to make antibody and other molecular forms of prophylactic and therapeutic treatment for the pathogen. This information also allows identification of new potential virulence factors that may be useful in the development of vaccines, or which may be suitable targets for therapeutic drugs. In addition, the sequencing data provides information about maintenance functions, horizontal gene transfer, conjugation, integration, insertion sequence (IS) elements, and evolution of these plasmids. The sequences from pCD1 and pMT1, and their significance, were first published by the inventors here in Lindler et al. *Inf. Immunity* 66:5731–5742, 1998 and Perry et al. *Inf. Immunity* 66:4611–4623, 1998, both of which are incorporated herein by reference in their entirety. Identification of maintenance functions provides information that is useful in designing cloning vectors, which can be used, for example, to study factors associated with pathogenicity.

Briefly, as described below in the examples, we determined the entire nucleotide sequence of the plasmid pMT1 from *Y. pestis* strain KIM5. We then analyzed the sequence and identified potential open reading frames (ORFs) encoded by the 100,990 bp pMT1 molecule. The complete sequence is set contained in SEQ ID NO 2 below. Based on yersinial codon usage for known yersinial genes, homology with known proteins in the databases and potential ribosome binding sites, it was determined that 115 of the potential ORFs likely encode proteins in *Y. pestis*. Seven new potential virulence factors that might interact with the mammalian host or flea vector were identified. The deduced amino acid sequences for 43 of the remaining 115 putative ORFs display no significant homology to proteins in the current databases. Furthermore, DNA sequence analysis allowed the determination of the putative replication and partitioning regions of pMT1.

A single 2,450 bp region within pMT1 that may function as the origin of replication (ori) was identified. The identification of this putative ori may allow construction of cloning vectors capable of replicating in Yersinia species. Such vectors will facilitate further research into the pathogenicity of these bacteria. The putative ori includes a RepA-like protein similar to those of the RepFIB, RepHI1B, P1 and P7 replicons. A plasmid partitioning function is located about 36 kilobases from the putative origin of replication and is most similar to the parABS bacteriophage P1 and P7 system. *Y. pestis* pMT1 encodes potential genes with a high degree of similarity to a wide variety of organisms, plasmids and bacteriophage. Accordingly, our analysis of pMT1 DNA sequence suggests the mosaic nature of this large bacterial virulence plasmid and provides insight into its evolution. The MT- and F1 encoding regions of pMT1 are surrounded by remnants of multiple transposition events and bacteriophage, respectively, suggesting horizontal gene transfer of these virulence factors.

The pCD1 sequence is 70,509 base pairs, and is presented as SEQ ID NO:1 herein. The SEQ ID NO:1 is actually 70,559 base pairs in length since it incorporates a 50 base pair repeat at each end of the linear representation of the circular plasmid. Sequencing of pCD1 has revealed a potential new Yop and Yop chaperone, two new IS, a set of LCRS genes very similar to those sequenced in the enteropathogenic yersinae, the IncFIIA replication region, and SopABC partitioning functions. Remnants of IS elements were found to be scattered throughout the plasmid, which suggests that pCD1 has undergone numerous insertional events as well as genetic recombinations and rearrangements during its history.

*Yersinia pestis* has an unique 9.5 kb plasmid, designated pPCP1, which contains genes encoding plasminogen activator/coagulase and pesticin. The total length of pPCP1 is 9,610 bp with a GC of 43%. The plasmid pPCP1 contains a copy of IS100. Three known gene functions located on this plasmid are as follows: 1) plasminogen activator and coagulase activity that is encoded on the same gene (pla), 2) pesticin, a toxin that inhibits growth of closely related bacteria, and 3) pesticin immunity gene whose product protects the bacteria from toxic effects of the pesticin. The origin of replication of pPCP1 is encoded on 780 bp region which is very similar to the origin of replication and the immunity region of Escherichia coli ColE1 plasmid. Loss of this plasmid leads to ineffective infection in guinea pigs and mice suggesting that the plasmid plays an important role in the invasion and infection of its mammalian host. The plasmid pPCP1 has also been sequenced and its sequence is presented as SEQ ID NO:3.

The sequences presented here are accurate to the best capabilities of the current state of the art, but may contain some minor errors, deletions, insertions or substitutions. It is also understood and expected that other strains of the host organism will have allelic variations of the genes in the host and therefore may carry different forms of the genes set forth in the sequence listing here. However, those of skill in the art expect such minor variations, and such minor sequence variations in *Yersinia pestis* -specific nucleotide sequences associated with nucleotide additions, deletions, and mutations, whether naturally occurring or introduced in vitro, would not interfere with the usefulness of these sequences in the detection of *Yersinia pestis*, in preventing Yersinia infection, and in methods for treating *Yersinia pestis* infection. Therefore, the scope of the present invention is intended to encompass such variations in the claimed sequences.

A *Yersinia pestis* -specific nucleotide probe is a sequence that is able to hybridize to *Yersinia pestis* target DNA present in a sample containing *Yersinia pestis* under suitable hybridization conditions, and which does not hybridize with DNA from other Yersinia species or from other bacterial species. It is well within the ability of one skilled in the art to determine suitable hybridization conditions based on probe length, G+C content, and the degree of stringency required for a particular application.

The probe may be RNA or DNA. Depending on the detection means employed, the probe may be unlabeled, radiolabeled, or labeled with a dye. The probe may be hybridized with a sample that has been immobilized on a solid support such as nitrocellulose or a nylon membrane, or the probe may be immobilized on a solid support, such as a silicon chip.

The sample to be tested for presence or absence of *Yersinia pestis* DNA may include blood, urine, feces, or other materials from a human, rodent, or flea susceptible to infection by *yersinia pestis*. The sample may be tested directly, or may be treated in some manner prior to testing. For example, the sample may be subjected to PCR amplification using appropriate oligonucleotide primers. To have reasonable assurance of success under conditions of variable stringency, it is preferred that such diagnostic probes uses sequences which are at least 15 nucleotides or longer in length. While probes as short as 15 base pairs can be made to work, probes of at least 25 base pairs or longer are preferred. Any means of detecting DNA-RNA or DNA-DNA hybridization known to the art may be used in the present invention. Since the plasmids set forth below are diagnostic of pathogen strains of *Yersinia pestis*, any set of 25-mers or longer from the sequences set forth below may usefully be employed as diagnostic probes for the presence of this pathogen in a biological sample.

Any and all of the ORFs presented here are of particular utility. Since these ORFs contain the coding regions for the proteins expressed by these plasmids, these ORFs are not just useful for diagnosis of the presence of the pathogenic host, they may be used to express the encoded proteins in other hosts. Placing the coding regions of-the ORFs under the control of non-native promoters permits the expression of the proteins encoded by the ORFs in other hosts. The ORFs can be inserted into any known expression vector adapted for a particular host and then can be transformed into that host for expression to produce proteins. Such proteins can be used for both prophylactic and therapeutic purposes. The proteins can be used to generate antibodies to the proteins natively produced by the *Y. pestis*, the provide pathogen specific. antibodies for diagnostic or therapeutic purposes. Proteins, or even peptides from the proteins have potential for targets for vaccination studies.

EXAMPLES

Isolation of pMT1 DNA

*Y. pestis* KIM10+ (Perry, et al. *J. Bacteriol.* 172:5929–5937, 1990), a strain that contains only pMT1, was grown in Heart Infusion Broth (Difco Laboratories, Detroit, Mich.) at 26–30° C. Plasmid DNA was isolated from the bacteria using alkaline lysis and polyethylene glycol precipitation (Birnboim, et al. *Nucleic Acids Res.* 7:1513–1523, 1979; Humphreys, et al. *Biochim. Biophys. Acta* 383:457–463, 1975). DNA libraries were prepared from purified pMT1, as described below.

Isolation of pCD1 DNA

*Y. pestis* strain KIM5 is conditionally avirulent due to deletion of the 102 kb pgm locus; it possesses all three prototypical *Y. pestis* plasmids (pPCP1, pCD1, and pMT1). Plasmid DNA was isolated from *Y. pestis* KIM5 by alkaline lysis followed by precipitation with polyethylene glycol. A mixture of pCD1 and pBR322 was transformed into *Escherichia coli* HB101. Transformants containing pBR322 were selected on the basis of ampicillin resistance. Ampicillin resistant transformants were transferred to nitrocellulose membranes and hybridized against pCD1 radioactively-labeled by nick translation, which allowed identification of cotransformants containing both pCD1 and pBR322. A selected cotransformant was cured of pBR322 by fusaric acid selection and used for isolation of pCD1. The pCD1 plasmid appears to be stably maintained in *E. coli* HB101. Plasmid DNA from *E. coli* HB101 (pCD1) cells grown in Luria broth was isolated by alkaline lysis followed by further purification with polyethylene glycol. Purified pCD1 DNA was used in subsequent sequencing.

pPCP1

DNA of pPCP1 was isolated for sequencing in a similar fashion.

DNA Sequencing.

DNA libraries of pPCP1, pCD1 or MT1 were prepared from nebulized, size fractionated plasmid DNA (Millon, et al. Gene, submitted) in the M13 Janus vector (Burland, et al. Nucleic Acids Res. 21:33.85–3390, 1995). DNA templates were purified from random library clones (Romantschuk, et al. Mol. Microbiol. 5:617–622, 1991), and DNA sequencing was preformed using dye-terminator labeled fluorescent cycle sequencing Prism reagents and ABI377 automated sequencers (Applied Biosystem Division of Perkin-Elmer). Sequences were assembled into segments of DNA sequence, referred to as contigs, by the SeqMan II program (DNASTAR), and clones were selected for sequencing from the opposite end to fill in coverage, resolve ambiguities and close gaps. Final coverage was about eight fold. The complete sequences of ball three plasmids are set forth in SEQ ID NO: 1 through 3 below.

In several instances,. pCD1 sequences differed from previously published sequences from the yersiniae or yielded unexpected results. To ensure that this did not result from mutations to pCD1 during carriage in *E. coli*, we sequenced these regions using pCD1 isolated from the conditionally virulent *Y. pestis* strain KIMS or pJIT7, a recombinant plasmid containing the IS1616 region adjacent to sopAB.

Sequence Annotation.

Open reading frames (ORFs) putatively encoding polypeptides at least 50 aa in length were identified using Geneplot or GeneQuest (DNASTAR) programs to display start codons (including GUG), stop codons and codon usage statistics plots for each reading frame. Codon usage analysis, used to predict ORFs, was assessed in the program by second and third order statistical comparisons with a matrix built from all available sequences for Yersinia species (Borodovsky, et al. Computational Chemistry 17:123–133, 1993). Although this matrix was more useful than one derived from *E. coli* genes, it was necessarily constructed from a relatively small data set. Generally, the start codon (including GTG and TTG) farthest upstream was used to annotate the ORF start. An ORF having fewer than 150 bases was included if it had a high codon usage score. For the first pass, putative amino acid sequences were searched against SWISS-PROT 34 using the BLOSUM26 matrix, by the DeCypher II System (TimeLogic Inc., Incline Village, Nev.).

Subsequent searches of the Swiss Protein, *E. coli* and non-redundant GenBank databases were obtained over the Internet using BLAST software (Altschul, et al., *Nucleic Acids Res.* 25:3389–3402, 1997) from the National Center for Biotechnology Information homepage (which can be found on the world wide web under ncbi.nlm.gov/BLAST). Pairwise protein alignments were with the BLAST algorithm. Protein localization was predicted for relevant translated orfs using the PSORT program (Nakai, et al. *Proteins: Structure, Function, and Genetics* 11:95–110, 1991). The prediction of membrane associated helices was with the TMpred program (Hoffman, et al. *Biol. Chem.* 347:166–172, 1993). Where appropriate, multiple protein sequences were aligned using the algorithm developed by Lipman et. al. (Proc. Natl. Acad. Sci. USA 86:4412–4415, 1989). These programs can be found as part of Pedros Molecular Biology Tools at Internet site www.iastate.edu.

Bank Accession Number

The annotated sequence for pMT1 and pCD1 were deposited in GenBank under accession numbers AF074611 and AF074612, respectively. These deposited sequences are also hereby incorporated by reference.

Sequence of pMT1

The fully-assembled pMT1 DNA sequence is a circular DNA sequence 100,990 bp in length. A map of the plasmid is set forth in FIG. 1, which illustrated the general location of sequences of interest. The complete DNA sequence of the plasmid is presented here as SEQ ID NO:2. Screening of the entire plasmid sequence using the DNASTAR program GeneQuest revealed 145 potential open reading frames (ORFs) along the entire length of the plasmid. The putative amino acid sequence of each ORF was used to search the various databases (GenBank, Swiss Protein,GenPept and *E. coli*) for proteins with potentially significant homologies. Table 1, set forth below, identified the location and other information of interest about many of the ORFs which were found to have homologies to known sequences.

TABLE 1

ORFs identified in Y. pestis pMT1 DNA sequence by classification.[a]

| Designation | ORF Class | Function or Comments | Organism or Element (Gene if known) | Accession Number | Location (bp) |
|---|---|---|---|---|---|
| DNA Metabolism | ORF1 | IS100 | *Y. pestis* IS100 (orfB) | U59875 | 73,885–74,661 |
| | ORF2 | Ligase | Bacteriophage T3 | X05031 | 74,680–75,777 |
| | ORF12 | Integrase | *Vibrio cholera* | U39068 | 82,931–84,109 |
| | ORF16 | DNA Pol III | *E. coli* | M19334 | 88,955–92,479 |
| | ORF26 | RecA | *Bacteroides fragills* (recA) | M63029 | 96,910–97,986 |
| | ORF34 | RepA | *E. coli* plasmid ColV | L01250 | Complement 717–1,781 |
| | ORF41 | exoA | Bacteriophage T4 (gene 47) | X01804 | 4,968–6,053 |
| | ORF43 | exoB | Bacteriophage T4 (gene 46) | X01804 | 6,271–8,199 |
| | ORF46 | IS200 | IS200 | U22457 | 9,675–10,184 |
| | ORF60 | Rep-like | *Coxiella burnetti* plasmid pQPH1 | L34077 | 16,197–16,895 |
| | ORF61 | SpoJ-like | *Streptococcus pneumoniae* | AF000658 | 16,862–17,563 |
| | ORF69 | Gene 17-like | Bacteriophage T4 (gene 17) | X52394 | 20.457–21,713 |
| | ORF93 | IS100 | *Y. pestis* IS100 (orfB) | U59875 | Complement 46,449–47,231 |
| | ORF94 | IS100 | *Y. pestis* IS100 (orfA) | U59875 | Complement 47,228–48,250 |
| | ORF101 | IS285 | *Y. pestis* IS285 (orf2) | X78303 | 51,013–52,221 |
| | ORF102 | Transposase TN4321 | *Enterobacter aerogenases* TN4321 (tn pA) | U60777 | 52,648–53,712 |
| | ORF108 | Membrane Endonuclease | *E. Coli* plasmid pKM101 (nuc) | U09868 | Complement 57,629–58,117 |
| | ORF111 | Resolvase | *Pseudomonas syringae* (stbA) | L48985 | Complement 60,161–60,781 |
| | ORF113 | ParA | Bacteriophage P1 (parA) | X02954 | 61,767–63,041 |
| | ORF114 | ParB | Bacteriophage P1 (parB) | K02380 | 63,038–64,009 |
| | ORF123 | Adenine specific DNA methylase | *E. coli* pEC156 EcoVIII methylase | U48806 | 66,648–67,325 |
| | ORF128 | Antirestriction | *E coli* | Z34467 | 69,208–69,714 |
| | ORF135 | DNA Partitioning | *Rhizobium meliloti* (Orf1, Orf2 of pRmeGR4a), *Shigella sonnei* (psiB), *Streptoccus pneumoniae* (spoOJ) | X69105, U82272, AF000658 | 70,730–72,739 |
| | ORF136 | IS100 | *Y. pestis* IS100 (orfA) | U59875 | 72,863–73,882 |
| Protein Metabiolism | ORF28 | HflC-like | *Vibrio parahaemolyticus* (hflC) | U09005 | 98,281–99,111 |
| | ORF63 | ABC transporter/ATP binding | *Archaeglobus fulgidus* (AF1064) | AE001029 | 17,500–18,198 |
| | ORF75 | L12 Ribosomal protein L12e | *Haloferax volcanii* | X58924 | 25,927–26,361 |
| Gene Regulation | ORF5 | Caf1R | *Y. pestis* (caf1R) | X61996 | Complement 77,118–78,041 |
| | ORF22 | PprB-like | *Pseudomonas putida* (pprB) | X80272 | 94,557–95,636 |
| | ORF56 | Repressor of flagella synthesis | *Salmonella abony* (fljA) | D26167 | Complement 13,278–13,841 |
| Known Virulence | ORF6 | Caf1M | *Y. pestis* (caf1M) | X61996 | 78,318–79,127 (GTG Start) |
| | ORF8 | Caf1A | *Y. pestis* (caf1A) | X61996 | 79,152–81,653 |
| | ORF9 | Caf1 | *Y. pestis* (caf1l) | X61996 | 81,734–82,246 |
| | ORF107 | Murine toxin | *Y. pestis* (ymt) | X92727 | Complement 55,788–57,551 |
| Lambda-like | ORF80a | V major tail fiber Intimin | *Bacteriophage lambda* *E. coli* O157:H7 (eae) | P03733 P43261 | 28,560–29,303 |
| | ORF84 | H tail fiber protein | *Bacteriophage lambda* | AF007380 | 30,041–34,618 |
| | ORF85 | M minor tail fiber protein | *Bacteriophage lambda* | P03737 | 34,660–34,995 |
| | ORF86 | L minor tail fiber protein | *Bacteriophage lambda* | P03738 | 35,052–35,783 |

TABLE 1-continued

ORFs identified in Y. pestis pMT1 DNA sequence by classification.[a]

| Designation | ORF Class | Function or Comments | Organism or Element (Gene if known) | Accession Number | Location (bp) |
|---|---|---|---|---|---|
| | ORF87a | K tail assembly protein | *Bacteriophage lambda* | P03729 | 35,815–36,570 |
| | ORF88 | I tail assembly protein | *Bacteriophage lambda* | P03730 | 36,561–37,148 (GTG Start) |
| | ORF89 | J host specificity protein | *Bacteriophage lambda* | P03749 | 37,164–41,801 |
| | ORF91 | Hypothetical protein ORF314 | *Bacteriophage lambda* | P03745 | 42,469–45,405 |
| | ORF92 | Tail fiber assembly | *Bacteriophage lambda* (tfa) | 225931 | 45,707–46,315 |
| Hypothetical in database[b] | ORF15 | CobT | *Pseudomonas denitrificans* (cobT) | P29934 | 85,075–87,441 |
| | ORF15a | CobS | *Pseudomonas denitrificans* (cobS) | P29933 | 87,539–88,771 |
| | ORF29 | Hypothetical protein | Bacteriophage P22 (ninX) | X78401 | 99,265–99,636 |
| | ORF33a | Hypothetical regulatory protein | Bacteriophage P1 | 76816 | 100,922–147 |
| | ORF38 | Hypothetical lipoprotein | *Bacillus subtllis* (orfK, yzeA) | L16808, Z93102 | Complement 3,530–4,552 |
| | ORF59 | Long hypothetical protein | *Pyrococcus horikoshii* (PHBW005) | AB009472 | Complement 14,573–16,132 |
| | ORF73 | SRP1 Hypothetical protein | Synechococcus PCC7942 pANL | Q55032 | 24,271–25,146 |
| | ORF104 | Hypothetical protein | *E. coli* | U70214 | Complement 54,405–54,803 |
| | ORF105 | Hypothetical protein | *E. coli* | U70214 | Complement 54,694–55,002 |
| | ORF116 | Hypothetical protein | Sphingomonas S88 (spsJ) | U51197 | 64,388–65,785 |
| | ORF131 | Hypothetical protein | *E. coli* | AE000133 | 70,427–70,657 |
| Fragments[c] | ORF23 | DNA polymerase 1 | *Lactococcus lactis* | U78771 | 95,646–96,641 |
| | ORF33 | Type II restriction enzyme | *Helicobacter pylori* | AE000647 | 100,590–100,925 |
| | ORF99 | Hypothetical protein | *Methanobacterium thermoautotrophicum* | AE000913 | Complement 49,210–50,004 |
| | ORF103 | Hypothetical transposase | *Salmonella typhimurium* | Z29513 | Complement 53,911–54,234 |
| | ORF103a | IS600 | *Shigella sonnei* | X05952 | 54,281–54,481 |
| | ORF106 | Hypothetical | *Shigella flexneri* | U97489 | 55,073–55,543 |
| | ORF106a | IS801 | *Pseudomonas syringae* | X57269 | 55,589–55,729 |
| | ORF110 | Hypothetical | *Salmonella typhimurium* | Z29513 | Complement 59,154–60,140 |
| | ORF115a | SamB-like | *Salmonella typhimurium* | D90202 | 87,539–88,771 |

In the above Table 1, the location of each of the ORFs is given in base pair number corresponding to the entire 100,990 base pairs of the entire plasmid. ORFs listed were assigned a putative function according to our criteria outlined in the general overview section of the results and discussion. Classification then was based on these putative functions.

If there was insufficient homology, by our criteria, with known proteins in the database the ORF has not been assigned a function in the table. In evaluating the significance of potential matches, several factors were considered. In general, if the putative translation product of a pMT1 ORF exhibits significant similarity to known proteins in the database, the putative protein was assigned a similar function. Homologies were considered to be significant if at least 25 percent of amino acids were identical over at least 35 percent of the protein in the database. The 25% identity was chosen to give a reasonable baseline, with adjustments being made for conservative amino acid substitutions to give higher similarity scores between protein molecules.

In specific instances, we have designated a protein function as "similar" based on less than 25 percent identity. The extent of homology with the database protein was set at 35 percent to allow for the possibility that protein domains might have different functions in different molecular contexts. The stringency was lowered when deciding if a putative protein might function in pathogenesis. In these cases, if the region of homology included at least 20 percent identical amino acids with a protein that might interact with or substitute for the action of a host protein, it was considered a potential virulence factor. Greater weight was given to potential alignments if the homology between the *Y. pestis* ORF and the target protein sequence was in a domain having a known function in host physiology. Finally, if the putative protein does not contain significant similarity to any known proteins, the upstream DNA was analyzed for ribosome binding sites (RBS) and the known codon usage for Yersinia genes was considered. After applying these criteria to the 145 potential ORFs initially identified on pMT1, 30 were eliminated and 115 putative coding regions remained. Of these 115 putative ORFs, 38 percent had no significant regions of homology to any protein in the current databases and seven percent had significant homology with previously described hypothetical proteins.

Newly Identified Virulence Factors of pMT1

Because *Y. pestis* is a facultative intracellular parasite and pMT1 is thought to enhance deep tissue spread of the organism, several ORFs having limited homology with proteins that may function during various stages of the plague life cycle were carefully examined. The ORFs include ORF 4 (base pairs 76,298 to 76,603), ORF 17 (bases 92,476–92,919), ORF 18 (complement to bases 92,949–93,512), ORF 21 (bases 94,015–94,448), ORF 72 (23,873–24,244), and ORF 74a (25,221–25,883). Again, all base pairs locations refer to the complete 100,990 sequence. Additional information about these identified virulence factors is presented in Table 2, below. Although many of these homologies are below our criteria for general ORF homologies, a more relaxed standard was indicated to aid in future research relating to plague pathogenesis.

TABLE 2

ORFs that may be potential virulence factors.

| ORF Designation | Location | Homologus Protein (Target) | Amount of Homology[a] | Accession Number | Reference |
|---|---|---|---|---|---|
| ORF4 | 76,298–76,603 | C-type natriuretic peptide from *Squalus acanthias* | 43/30 | P41319 | 83 |
| ORF17 | 92,476–92,919 | Delta insecticidal protein from *Bacillus* thuringiensis | 40/18 | P05628 | 35 |
| ORF18 | Complement 92,949–93,512 | RTX Toxin of *Actinobacillus pleuropneumoniae* | 21/11 | D16582 | 32, 65 |
| ORF21 | 94,015–94,448 | Laminin of *Homo sapiens*, | 23/5 | Q16787 | 79, 95 |
| | | Paramysin-related protein of *Onchocerca gibsoni* | 21/18 | U20609 | 25, 99 |
| ORF72 | 23,873–24,244 | Major Myristoylated Alanine-rich Protein Kinase C Substrate (MARCKS) | 24/32 | P29966 | 41 |
| ORF74a | 25,221–25,883 | *Bacteriophage lambda* V protein, | 40/41 | P03733 | 81 |
| | | *Citrobacter freundii* intimin | 30/10 | Q07591 | 82 |

[a]Percent identical amino acids over the percent of the total target protein sequence.

In addition, one potential new IS element, designated IS1618, is located from bp 52,465 to 53,758 (or bases 2365–3658). This sequence, the boundaries of which are defined by two directly repeated sequences (GATGATAA), flanks a putative transposase designated ORF102. ORF102 had the greatest identity with a putative transposase previously found in *Enterobacter aerogenases* (Smith, et al. *J. Gen. Microbiol.* 139:1761–1766, 1993)(40% over 96 percent of the target protein) and a putative transposase previously described in *Yersinia enterocolitica* (Rakin et al. *FEMS Microbiol. Lett*. 129:287–292, 1995) (36% identity over 96% of the target protein).

The nucleotide sequence of *Y. pestis* pMT1 has provided a wealth of new information. Our analysis has allowed us to identify several genes to target for further study in order to access their possible role in pathogenesis. Deciphering the potential role of these proteins improves our understanding of disease as well as host physiology. As more complete virulence plasmid DNA sequences become available, we will begin to understand the mosaic nature of these molecules and what new combinations we might expect in the future. Detailed molecular analysis of the structure of virulence plasmids will impact our ability to predict the emergence of bacterial pathogens as well as detect their presence.

Sequences of pCD1

Figure 2:
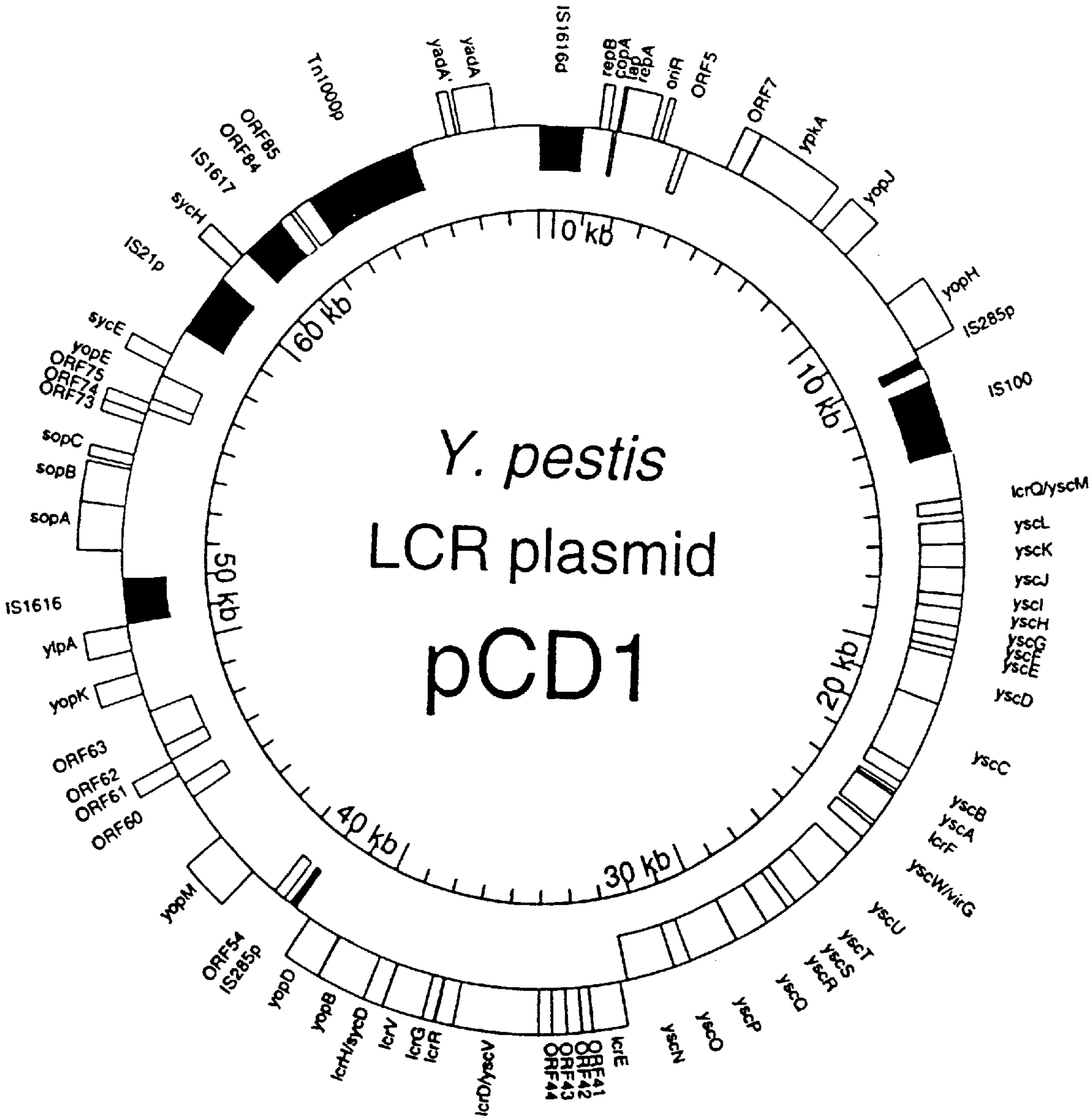
FIG. 2 is a similar plasmid map of the plasmid pCD1.

A genetic map of the *Y. pestis* KIM5 pCD1 plasmid, which is 70,509 nucleotides in length, is shown in FIG. 2. Again the complete DNA sequence of the plasmid is contained in the sequence listing appended hereto, this sequence being SEQ ID NO:1. Again the ORFs of the sequence was determined by computer analysis and searched against existing data bases. Table 3 below lists significant ORFs and their primary characteristics. Most IS element remnants and partial ORFs that appear to be nonfunctional due to IS-related events or other deletions and rearrangements are not included in Table 3.

TABLE 2

ORFs encoded on pCD1 of *Y. pestis* KIM5[a]

| geneb or ORF | Function | Orientation | Begin-ing of ORF | End of ORF | Number of amino acids | Isoelectric point | kDa |
|---|---|---|---|---|---|---|---|
| repB (copB) | Negative regulator of repA transcription | + | 1,171 | 1,425 | 85 | 9.72 | 9.58 |
| tap | Required for translation of repA | + | 1,667 | 1,741 | 25 | 9.31 | 2.82 |
| repA | Plasmid replication | + | 1,734 | 2,600 | 289 | 10.96 | 33.55 |
| Orf5 | Unknown | – | 3,645 | 3,427 | 73 | 9.96 | 8.22 |
| Orf7 | Unknown | + | 4,758 | 5,186 | 143 | 4.39 | 15.78 |
| ypkA (yopO) | Targeted effector; ser thr kinase | + | 5,204 | 7,402 | 733 | 6.53 | 81.74 |
| yopJ (yopP) | Targeted effector; causes apoptosis in macrophages and interferes with cell signaling | + | 7,798 | 8,664 | 289 | 7.07 | 32.46 |
| yopH | Targeted effector; protein tyrosine kinase; interferes with cell signaling at focal adhesions | + | 10,347 | 11,753 | 469 | 8.68 | 50.87 |
| lcrQ (yscM) | Negative regulator of LCR expression | – | 16,148 | 15,801 | 116 | 6.34 | 12.41 |
| yscL | Type III secretion component | – | 17,038 | 16,373 | 222 | 4.57 | 24.65 |
| yscK | Type III secretion component | – | 17,613 | 16,984 | 210 | 6.75 | 23.99 |
| yscJ | Type III secretion component | – | 18,347 | 17,613 | 245 | 7.43 | 27.04 |
| yscI | Type III secretion component | – | 18,701 | 18,354 | 116 | 4.47 | 12.67 |
| YscH (yopR) | Secreted; unknown function | – | 19,199 | 18,702 | 166 | 5.14 | 18.35 |
| yscG | Type III secretion component | – | 19,543 | 19,196 | 116 | 6.60 | 13.07 |
| yscF | Type III secretion component | – | 19,808 | 19,545 | 88 | 7.13 | 9.49 |
| yscE | Type III secretion component | – | 20,009 | 19,809 | 67 | 7.31 | 7.61 |
| yscD | Type III secretion component | – | 21,265 | 20,006 | 420 | 5.85 | 46.93 |
| yscC | Type III secretion component | – | 23,085 | 21,262 | 608 | 6.49 | 67.35 |
| yscB | Unknown | – | 23,504 | 23,091 | 138 | 9.27 | 15.41 |
| yscA | Unkown | – | 23,828 | 23,730 | 33 | 9.82 | 3.86 |
| lcrF (virF) | Activator or LCR expression | – | 24,722 | 23,907 | 272 | 8.91 | 30.84 |
| yscW (virG) | YscC lipoprotein chaperone | – | 25,241 | 24,846 | 132 | 10.12 | 14.71 |
| yscU | Type III secretion component | – | 26,881 | 25,817 | 355 | 8.81 | 40.39 |
| yscT | Type III secretion component | – | 27,666 | 26,881 | 262 | 5.67 | 28.45 |
| yscS | Type III secretion component | – | 27,929 | 27,663 | 89 | 6.32 | 9.57 |
| yscR | Type III secretion component | – | 28,584 | 27,931 | 218 | 4.68 | 24.43 |
| yscQ | Type III secretion component | – | 29,504 | 28,581 | 308 | 5.08 | 34.42 |
| yscP | Type III secretion component | – | 30,868 | 29,501 | 456 | 5.44 | 50.42 |
| yscO | Type III secretion component | – | 31,332 | 30,868 | 155 | 7.84 | 19.00 |
| yscN | Type III secretion component | – | 32,648 | 31,329 | 440 | 6.48 | 47.81 |
| lcrE (yopN) | Secretion control | + | 32,846 | 33,727 | 294 | 5.07 | 32.67 |
| tyeA | Secretion and Yop targeting control | + | 33,708 | 33,986 | 93 | 4.21 | 10.75 |
| Orf42 | Unknown | + | 33,973 | 34,344 | 124 | 5.54 | 13.61 |
| Orf43 | Unknown | + | 34,341 | 34,709 | 123 | 6.32 | 13.76 |
| Orf44 | Unknown | + | 34,706 | 35,050 | 115 | 6.92 | 13.12 |
| lcrD (yscV) | Secretion | + | 35,037 | 37,151 | 705 | 5.04 | 77.81 |
| lcrR | Unknown | + | 37,148 | 37,588 | 147 | 10.27 | 16.46 |
| lcrG | Secretion control; efficient Yop targeting | + | 37,630 | 37,917 | 96 | 8.15 | 11.02 |
| lcrV | Diffusible effector; secretion and targeting control | + | 37,919 | 38,899 | 327 | 5.66 | 37.24 |
| lcrH (sycD) | YopB and YopD chaperone | + | 38,912 | 39,418 | 169 | 4.61 | 19.02 |
| yopB | Yop targeting | + | 39,396 | 40,601 | 402 | 7.09 | 41.83 |
| yopD | Yop targeting; negative regulator | + | 40,620 | 41,540 | 307 | 6.80 | 33.39 |
| Orf54 | Unknown | – | 42,709 | 42,386 | 108 | 9.66 | 12.61 |
| yopM | Targeted effector | + | 43,481 | 44,710 | 410 | 4.23 | 46.21 |
| Orf60 | Unknown | – | 46,365 | 45,946 | 140 | 7.79 | 15.81 |
| Orf61 | Unknown | + | 46,637 | 47,026 | 130 | 7.33 | 14.80 |
| sycT | YopT chaperone | – | 47,468 | 47,070 | 133 | 4.43 | 15.42 |
| yopT | Targeted effector | – | 48,436 | 47,468 | 323 | 9.13 | 36.31 |
| yopK (yopQ) | Yop targeting | + | 48,936 | 49,484 | 183 | 4.37 | 21.00 |
| ylpA | pseudogene | + | 50,089 | 50,718 | 210 | 5.80 | 22.40 |

TABLE 2-continued

ORFs encoded on pCD1 of *Y. pestis* KIM5[a]

| gene[b] or ORF | Function | Orientation | Begin-ing of ORF | End of ORF | Number of amino acids | Isoelectric point | kDa |
|---|---|---|---|---|---|---|---|
| sopA | Plasmid partitioning; negative regulator of sopAB transcription | + | 52,730 | 53,896 | 389 | 5.82 | 43.41 |
| sopB | Plasmid partitioning; binds to sopC region | + | 53,896 | 54,858 | 320 | 10.19 | 35.61 |
| Orf73 | Unknown | + | 56,087 | 56,362 | 92 | 6.16 | 10.10 |
| Orf74 | Unknown | + | 56,355 | 56,654 | 100 | 5.51 | 11.67 |
| Orf75 | Unknown | − | 56,792 | 56,496 | 99 | 9.88 | 11.19 |
| yopE | Targeted effector; causes actin depolymerization | − | 57,453 | 56,794 | 220 | 6.59 | 22.99 |
| sycE (yerA) | YopE chaperone | + | 57,647 | 58,039 | 131 | 4.49 | 14.65 |
| sycH | YopH chaperone | + | 60,796 | 61,221 | 142 | 4.81 | 15.76 |
| Orf84 | Unknown | − | 62,897 | 62,568 | 110 | 8.98 | 13.00 |
| Orf85 | Unknown | − | 63,500 | 63,036 | 155 | 4.97 | 17.71 |
| yadA' | pseudogene | + | 67,532 | 67,783 | 84 | 5.21 | 8.92 |
| 'yadA | pseudogene | + | 67,900 | 68,835 | 312 | 6.84 | 32.47 |

[a]ORFs within transposable elements as well as disrupted or partial ORFs (except for ylpA, yadA', and 'yadA) are not included in the table.
[b]Except for copB, yopN, yscV, and yerA, all alternate gene designations, in parentheses, are *Y. enterocolitica* terminology; copB - plasmid R100 terminology; yopN - *Y. enterocolitica* and *Y. pseudotuberculosis* terminology; yscV - proposed terminology change; yerA - *Y. pseudotuberculosis* terminology

New Potential Virulence-related ORFs

Fourteen ORFs are not obviously associated with IS elements and either have no significant similarity to proteins in the database with known functions or have features suggesting a virulence-related role. These are ORFs that deserve future study as potentially having virulence or virulence-accessory functions.

ORF75 (Table 3) lies just 1 bp downstream of yopE and lacks an obvious ribosome binding site or upstream promoter. The ORF could encode an 11,192 Da protein with at least one likely transmembrane domain and a noncleavable signal sequence. Its expression conceivably is translationally coupled to that of yopE suggesting that it could be a member of the LCR. yopE has been called monocistronic, based on its estimated transcript size (750 bases in *Y. pseudotuberculosis* ). The presence of this ORF has not been noted in the literature, even though the beginning of Orf75 is present in the sequences previously submitted for *Y. pseudotuberculosis* yopE, *Y. enterocolitica* 0:9 and *Y. pestis* EV76. Interestingly, it is intact but separated from yopE by an insertion element in *Y. enterocolitica* 0:8 strain 8081. At high doses, a *Y. pseudotuberculosis* mutant containing an insertion in this ORF did not cause loss of virulence in mice infected orally (Forsberg, et al. *J. bacteriol.* 172:1547–1555, 1990). Given that YopE's importance in virulence was determined with polar insertion mutants, the significance of this ORF needs to be thoroughly tested.

While assembling this data, we learned that two new ORFs we found in *Y. pestis* have been designated as YopT and SycT in *Y. enterocolitica* (Miller, et al. *J. bacteriol.* 172:1062–1069, 1991). sycT and yopT are arranged in what appears to be a bicistronic operon upstream 500 bp and on the opposite strand from yopK (FIG. 2). These genes indeed have properties suggestive of a Yop and associated Syc. sycT is predicted to encode an acidic 15.42 kDa peripheral protein (Table 3). The database search brought up weak homology with SycE (with which there is 22% identity). Alignment of SycT with SycE, LcrH (SycD), and SycH shows the greatest similarity toward the C termini of the proteins, as previously demonstrated in a comparison of SycE and LcrH/SycD. YopT is predicted to be a peripheral 36.31 kDa basic protein (Table 3). It shows 36.7% identity in residues 98–322 with the C-terminus (residues 648–874) of a surface antigen in *Haemophilus somnus* that is associated with serum-resistance. The regulation, mechanism of action, and role in plague of YopT should be investigated.

ORFs 42, 43 and 44 (Table 3), located immediately downstream of tyeA (FIG. 2), have been noted to exist in *Y. enterocolitica* (Winans et al. *J. bacteriol.* 154:117–1125, 1083). ORF42 has been sequenced in *Y. pseudotuberculosis* and a polar insertion near its 3' end caused a calcium-independent growth phenotype (Forsberg, et al. *Mol. Microbiol.* 2:121–133, .1988), typical of mutations in genes necessary for the functioning of the type III secretion system. Because this mutation was complemented by DNA lacking a complete lcrD/yscV gene (downstream of ORF44), the phenotype is not likely to be caused by disruption of lcrD/yscV. This, taken together with their location (within the LCR cluster and downstream of tyeA, which is involved in Yop secretion control), suggests that one or more of the ORFs 42 through 44 have a role in secretion or secretion control.

ORF5 (Table 3) is isolated from other virulence-related genes, within a gap between the origin region and an IS1236 remnant. It is presently unknown whether the sequence. encodes a virulence-related factor.

ORFs 59, 60, and 61 (Table 3; FIG. 2) lie between yopM and sycT. Orf59 is closest to yopM (242 bp away), on the opposite strand, and is predicted to encode a 4 kDa soluble acidic protein (Table 3), which is significantly smaller than typical Sycs. Orfs 60 and 61 lie 875 bp from Orf59, are separated by 272 bp, and are divergently oriented. Both are predicted to encode membrane-associated proteins with mildly basic pIs that hence do not resemble typical Sycs (acidic, soluble, ca. 16 kDa) or Yops (soluble). Orf 60 has an uncommon translation initiation codon (leucine) (Table 3).

ORFs 73 and 74 (Table 3) lie in the vicinity of yopE. The predicted proteins are 10–11 kDa soluble acidic proteins that show high similarity to unknown proteins of similar lengths in *Mycobacterium tuberculosis*; however, neither ORF has a common translation initiation codon (leucine [ORF73] and valine [ORF74]). Both ORFs are predicted to be transcribed in the same direction, with Orf74 overlapping Orf73 by 8 bp (Table 1).

ORFs 84 and 85 (Table 3; FIG. 2) occupy the region between IS1617 and Tn1000p. They are separated by 139 bp and would be transcribed in the same direction. The predicted product of Orf84 is a basic soluble protein and the product of Orf85 is predicted to be an acidic soluble protein (Table 3).

We identified a number of intact, defective, and partial IS elements in pCD1. The site of an IS100 insertion, an element with numerous copies in the *Y. pestis* genome (Fetherston, et al. *Mol. Microbiol.* 13:697–708, 1994; Portnoy, et al. *Infect. Immun.* 43:108–114, 1984), was confirmed and refined. Two new IS elements, which we have named IS1616 and IS1617, were discovered (FIG. 2) and were registered through Dr. Esther Lederberg Plasmid Reference Center, Stanford, Calif. In addition, numerous IS element remnants were identified; these partial Iss primarily cluster in four regions of pCD1 (discussed below).

It is curious that IS100 is nearby one end of the yscM to yopD LCR cluster and two partial IS285 elements bound this same region (FIG. 2). The type III secretion system and regulatory genes, exemplified by this LCR cluster, is widespread among bacterial pathogens and has been suggested as a possible pathogenicity island (PAI). PAI hallmarks include carriage of virulence genes, a distinct GC content compared to the host bacterium, a discrete genetic unit often flanked by direct repeats, association with tRNA genes and/or insertion sequences, presence of "mobility" genes (transposases, etc), instability, and absence in less pathogenic strains. An additional requirement of a chromosomal location may be somewhat artificial given the large sizes of many virulence plasmids. Although the LCR cluster does have IS elements associated with it, we failed to detect any tRNA genes anywhere on pCDT. In addition, the LCR cluster does not contain effector Yops (except for lcrV). Finally, the GC content of this region (44.8%) matches that of the entire plasmid and is similar to the 46–47% GC content of the genome of *Y. pestis.*

Insertion elements. Several mobile genetic elements have been found in the pathogenic yersiniae and most of them are present on LCR plasmids as well as the chromosome. ISs known to be associated with the LCR plasmid of *Y. pestis* include IS100 and IS285 Additional elements are found on the LCR plasmid of *Y. enterocolitica* but are not present on the *Y. pestis* plasmid Sequence analysis of pCD1 from *Y. pestis* KIM5 revealed the presence of three complete insertion elements and numerous partial IS elements. Complete and partial IS elements with >85% identity at the DNA sequence level were considered to be the same as previously described IS elements. For the remaining elements, the highest database match at the aa sequence level was considered the closest relative. Only complete IS elements were given new IS number designations.

An intact copy of IS100 is located downstream of yopH in pCD1 (FIG. 2). There are numerous copies of IS100 throughout the genome of *Y. pestis* KIM strains; the IS100 element (bp 12,609 to 14,562) in pCD1 (bp 12,609–14,562 of SEQ ID NO:1) is 100% identical in size and nucleotide sequence to a copy of IS100 present on the pesticin plasmid of *Y. pestis* strain EV76-6. A five base pair direct repeat flanks the IS100 which appears to have inserted within the relic of another insertion element. Five and seven base pair duplications have been found flanking other IS100 elements in *Y. pestis.*

IS1616 is a new 1,254 bp insertion element located at bp 50,753 to 51,987 of the entire assembled sequence, between ylpA and the sopABC partitioning region. The inverted repeats at the ends of IS1616 are 40 bp long and contain 9 mismatches. No direct repeats were detected flanking this element. While some elements do not generate a direct repeat upon transposition, the absence of direct repeats could be indicative of changes in the flanking DNA as a result of mutations that have occurred over time. There are three open reading frames within IS1616, the first ORF (OrfA, bp 50,825 to 51,142) is predicted to encode a protein of 105 aa with a pI of 12.6. A second ORF of 186 aa (OrfB, bp 51,064 to 51,624) overlaps OrfA in the −1 frame. An additional 101 aa (orfc, bp 51,625 to 51,930), which may have originally been part of the second ORF, are encoded in the same frame just past the stop codon at bp 51,622 for OrfB.

IS1617 is a new 1,214 bp element, with inverted repeats of 39 and 40 bp containing 13 mismatches, located downstream of sycH. The five bases flanking each end of IS1617 are identical in 4 out of 5 positions. Like IS1616, this element belongs to the IS3 family and contains 2 overlapping ORFs with OrfB in the −1 frame relative to OrfA. OrfA could encode an 88 aa protein (bp 62,202 to 62,468, complement) while OrfB is open for 289 aa.(bp 61,369 to 62,238, complement). A potential translational frameshift window of AAAAAAG is present in OrfA. IS1617 is more closely related to IS1222 from *Enterobacter agglomerans* and to ISD1 found in *Desulfovibrio vulgaris* than to IS1616. A remnant of IS1617 is present downstream of yopj in pCD1 as well as in *Y. pseudotuberculosis* pIB1.

We found no evidence for the existence of yopL and, in *Y. pestis*, ylpA and yadA-are pseudogenes. Although regulatory and secretory components of the LCR constitute a contiguous LCR cluster, elements suggesting this region is a pathogenicity island were not identified. Effector Yops are scattered throughout the plasmid and have widely varying GC contents, indicative of multiple gene acquisition events. This observation coupled with the presence of IS remnants from only distantly related microorganisms suggest a very complex history of DNA acquisition, insertions, deletions, and rearrangements was required for assembly of pCD1.

We failed to find genes with similarities-to putative virulence factors that are not potential members of the LCR. However, we did identify eight ORFs of unknown function (Orfs 5, 59–61, 73, 74, 84, and 85). Orfs 7, 42–44, and 75 as well as YopT and its chaperone SycT are potential new members of the LCR virulence system. Sequence analysis of Orf7 suggests that it could be a chaperone for YopJ. Further investigation of these Orfs will allow assignment of their functions as LCR members or non-LCR virulence determinants.

We corrected the sequence of yopM, showing that it has two additional LRR repeats that are absent in *Y. enterocolitica*. While most LCR-related *Y. pestis* gene products showed 98% identity to their analogous *Y. enterocolitica* gene products, YopJ, YscG, YscE were ~94% identical to *Y. enterocolitica* products. It will be necessary to determine whether any of the differences in YopM, YopJ, YscG, YscE and the lack of a functional YlpA gene product are involved in differing levels of virulence among the pathogenic yersiniae.

An analysis was also done of the ORFs present in pPCP1. This analysis is presented in Table 4 below.

TABLE 4

| Gene ID | Coords. | Genpept | Gi#match | Description of Match |
|---|---|---|---|---|
| Y0002 | 971 > 1165 | gi\|455143 | RNA I | inhibition modulator protein (rom) |
| Y0003 | 1532 > 1903 | gi\|144312 | ORF | [Plasmid ColE1] |
| Y0004 | 2389 > 2826 | gi\|1200166\|gnl\|PID"e223344 | | pesticin immunity protein [*Yersinia pestis*] |
| Y0005 | 2861 < 3934 | gi\|984824 | | pesticin [*Yersinia pestis*] |
| Y0006 | 4052 > 4468 | | | unknown |
| Y0007 | 4711 > 5649 | gi\|155525 | | plasminogen activator [*Yersinia pestis*] |
| Y0008 | 5836 < 6135 | gi\|1806206\|gnl\|PID\|e293663 | | unknown [*Mycobacterium tuberculosis*] |
| Y0009 | 6135 < 6482 | | | unknown |
| Y0010 | 7312 < 7686 | | | unknown |
| Y0011 | 7743 > 8765 | gi\|1655837 | ORFA; | putative transposase [*Yersinia pestis*] |
| Y0001 | 8762 > 9544 | gi\|1655838 | ORFB; | putative transposase [*Yersinia pestis*]-- |

Thus the genes Y004, Y005 and Y007 are of particular interest as targets for use in treatment strategies due to their relationship with pathogenicity.

We claim:

1. A recombinant DNA construction comprising an open reading frame placed under the control of a non-native promoter, the open reading frame being SEQ ID NO:3, base pairs 2389 to 2826, as found in *Yersinia pestis* plasmid pPCP 1.

2. A host transformed with the DNA construction of claim 1.

* * * * *

SEQUENCE LISTING

<160> NUMBER OF SEQ ID NOS: 3

<210> SEQ ID NO 1
<211> LENGTH: 70559
<212> TYPE: DNA
<213> ORGANISM: Yersinia pestis

<400> SEQUENCE: 1

```
tttactctgc ttcgctgaat tttcgggttg atgtaaaacg tctgcaactg cgtgaattgc     60

atcaacagag ccggggagca gccggcagca gaacactgag tctgctgatg cgtcagtcgg    120

gttataacgt ggtgcgctgg ctggcccgca ggctgatgcg ggaatgtggt ctggcgagtc    180

gccaacccgg aaaacctcgt taccgtggcg aacgggaggt gtcactggca tcgccagact    240

tactgaaaag gcagtttaag ccgtcggagc ccaatcgtgt gtggagtgga tatatcagct    300

atatcaaagt caatggtggc tggtgctacc tggcactggt gattgacctt tactctttcc    360

attggtgagt tatccaggca gttacccctg cggctcatac tctgcatcac tccgttcctc    420

cacagtaact gcctgtattt cttactcctg tactgccctc cttgatccga atgaaacagc    480

agcctctttt cccttgggcg cgtctccagt gcattacgcc aggctcgaca caccagctca    540

gcatccgggg atgacgatat ggcactgccc actatccgac gggagtaaac cgaagcctga    600

aaagtgaatg gctgcctgta gggggctata tggatgtcca tcatgcggta cgagatatcg    660

gtgaatggat acaaagttat tacaacacac ccccatcggc acaatggtgg attaccgccc    720

tgtgaatacg aagagcggtg gaaaaaggct acgaaggtgt cctgattttg tgatccacta    780

caggatggat ctgttggtca atgccggcat tcctgtccga actgtcaaca gtttcaaagc    840

gcttcacgac aaggtgatta tcgttgatgg caagaatacg cagatggggt cgttcaattt    900

tagccaagca gccgtacagt ccaactcgga gaatgtgctg attatatggg gggacttcac    960

ggtggtacag gcgtatctgc agtattggca gtcacgctgg aataaaggaa ctgactggcg   1020

ttcgtcgtac tgatctcact cttttcgctg agtcattaat gtgatccgtg cgccaacacg   1080

ggttatgtct gcaaaagtta agtcgctgat ttcataaatc tgttgtattc tctgcgaaac   1140

gatccttgtt tgatctttga gggggctgat atgtcgcaga tcgaaaatgc agtaacttcc   1200

tcatcgaaac gtgcctacag aaaggggaac ccgttaactg gagccgagaa acaacgtatg   1260

tctgtttccc ggaaaaaaga gacacataaa gctataaatg tgttcattca gaacgatctc   1320
```

-continued

```
aaaaacgaac ttttacaact ctgtgaagat tcaggtttga ctcagacaga aatgattgag   1380
cgctggattc agagagaaaa ggccgctaga actaatgcag cttgaatggc aactaagtta   1440

ctttcttgat ccttcaggca gtgagtgcta gattaccgat tgtttaaaga atttttggct   1500

ggccacgccg taaggtggca gggaactggt tctgctaagg tgtttacttg gaaccagaaa   1560

agcaaaaacc ccgataaact tcctcatctt tggcgaggcg agaaggttac cggggcccac   1620

ttaaaactgt atagaagctg ttgctctata cagggagtat atgtgcatgt tcagaaaagt   1680

tcaatacctt ctgcgcttgt tactccttcc gtgcaacata agtgcgggaa ggtgtgacta   1740

accaccaggc cctgttcaca catcattatc gacaggttaa aaacccgaat ccggaattta   1800

cgccgcgaga gggtaaaaaa accctgccgt tctgccgtaa gctgatggcg aaagccgaag   1860

gcttcacatc tcgttttgat ttctccatgc acgtcgcatt cgcgcgttct ctgagtttgc   1920

gtcatcgtat gccgccgtta ctacgtcggc gtgctatcga tgcattactg cagggtatgt   1980

gtttccacta cgacccactg gccaaccgta tccagcgctc gattaccaat ctggccattg   2040

agtgtggtct ggcgacagag tcaaagagtg gcaacctttc catcacccgc gccacgcgtg   2100

cgctgcgctt tttatctgag ctggggctga ttacctacca gaccgaatat gatccacaga   2160

ttggctgtaa tattccgact gatatcacgt tcacaccggc gctgttttct gcgttggatg   2220

tgtcggacgt tgctgtcgca gcagcccgac gcagccgcgt tgaatgggaa aatcagcaaa   2280

gggagaaaca acgtctgcct agattggaga tggatgagct gatagcaaag gcatggcggt   2340

tcgtccgcga gcgtttccgt agctatcaaa ctgaacgtaa ggctcatgga ttgaaacgtg   2400

cccgtgcgcg ccgtgatgtt gaccgtacgc gccgtgacat tgaagctatc gttaaccggc   2460

agctgacgcg tgagatagct gaggggcggt ttgtcggtaa tctggatgcg gtacgcaggg   2520

agaaagcccg tcgcgtgaag gaacgcatgc tgatgtccag gaacaataac tacacccggt   2580

tggccaccgg cgctacctga cgtcgtattt actgaaaatc cggttagcgc cggaggattt   2640

cgctcgtctg cctcctgtca gtgcttgtta tttgagcgat gtgacggccg ctacatgacc   2700

tatcttctct ttcccgccct gaaaatgccc tcgaattctc ccaatatcgt cgcttgaatg   2760

tactgattta ggttatccac agttaactgc aagggaactt cccataaagt tacaaccgat   2820

atgtttttta agcgccagcc gaacttgttt taaagtgcgt ggtttctttt aaaccactga   2880

tcagcacttc ttttaaatac cttttctttt attcctataa ataaataacc tattcgtcgt   2940

ctgccttttg gacagactat gataatgccc gcccttgcag cgaacttacg ttcgcgccgg   3000

ttcggaaaca aagaaatacc tcctatcacg atgctacgag cgcataaacc cttattagtt   3060

acaacattca cgattcgacc aaaaaaatac cagaccgcat acatctgaga ccactgcgcg   3120

cacccttacc cactaaaaag ccgccccgcc ccgggccaac ggcccggaac agagtggctt   3180

tacaatgagt gttgtaacta aaattttcga gtcgctgcaa gtcatgtcgc tggaagtcat   3240

tcgaacacgc tcgtaagcgg ccctaatggc ccgctaacgc ggagatacgc cccgcctgcg   3300

gcaaagcctt gtcgggacca ctccgaccgc gtaatgaagc acctacgcta cttttagtgg   3360

gtttagcttt gcagggagga gattgggatt ggtgaaacct atcaaaccgg aaccggctac   3420

gccgggctat cggcgccaat tgtcaacaga gttatagtta atatccgctg gcgccttcat   3480

gccgcgatgc ggcattgaaa agaccggctg cgcactgctc gcctgtccgg taaggacatg   3540

atataaacgt ttgtgtttat aagcactttt gtggatatcg ttatgcagct gagtgactac   3600

attgacagtg tatacggaac agccgtaagc gagcggcgat ctcatattgt taactcactt   3660

ccgttatcac actctggtct cagtcaatac aacgaacctg aggtgaaata tgacgacacg   3720
```

-continued

```
gtattctcgt agtgaacggc agcaccatct cgacgcctgg caatagagct gaatgtctaa   3780
aaaacactac tgtcggctgc atgacttgaa catcgccacc ttttattact ggctcaaaca   3840
tcatcaagat gacaccaccg ttgccattcc ccctgcgttt atccccgctc gccgggtaat   3900
accagacaat aacggtaccg aggcagtgac cctcaacctc cccaatggct gttcggtcag   3960
ttgtcttcct gctcagttac gcgctgttat gcaggcctta tccctatgtt gacgccacaa   4020
cacatctggt tggcacgcga gccggtcgat atgcgtcgcg gtatcgcaat acattaccga   4080
ccatctgcat cagccctggc aaggcgaagc cgcctttgtc ttttgcaaca aaggcgcgtt   4140
cgcgtatcaa agttctgcgt tggaacaaac acggggtctg gttgtgaaga ggctgctgtt   4200
tcattcggat cagggagggc agtacaggag taagaaatcc aggcagttac tgtggaggac   4260
cggagtgatg cagagtatga gccgcagggg taactgcctg gataactcac caatggaaag   4320
agtgttccga agcctgaaaa gtgaatggct gcctgtaggg ggctatatgg atgtccatca   4380
tgcggtacga gatatcggtg aatggataca aagttattac aacacacccc catcggcaca   4440
atggtggatt accgccctgt gaatacgaag agcaggggaa aaaggctacg aaggtgtcct   4500
gattttgtga tccactacag caacggaata gctccgctca gttatctgac ggacagcttc   4560
ttccttaaat tcaggggtaa aacgtggtgt gcccatagac tcctcctatg cttaagatat   4620
aggtcagatt tgtctacagg ttcgggggct ccccaaatat ctacaataac taaaaatcag   4680
tggctggaag tgatatattc tgggacgggt ttaatcaatg atagatatca ccgtaaatca   4740
gattaaagag cttttgtgtg attaacacca cctttactga gttactccca aaaatagcaa   4800
gtcactttgg attagataaa ttgagccaag atgaatatgg cttgtgtgag cttatcctca   4860
acgaccgagt cgttattatg ctgagggctg atgaaatatt gaatcgattg actctgttgg   4920
ggccaatctt aggattttct ggaccagagg cgcgcagcgc cgctagtcag cttttttttct   4980
gttatagcat caatgccttg aataaggacg gcccttgttt cgcttggagt gaagaactgg   5040
ggctgatcgc attcaagcac ctttctctcg acgagctgaa tgttgagaac gttagcaagg   5100
agatagcgaa cttttacgac tggttgagct tggtcagttt accagcagaa actgcccctt   5160
catactcaat ctactcaatc ggttaaatgg ggatgagtaa agcatgaaaa gcgtgaaaat   5220
catgggaact atgccaccgt cgatctccct cgccaaagct catgagcgca tcagccaaca   5280
ttggcaaaat cctgtcggtg agctcaatat cggaggaaaa cggtatagaa ttatcgataa   5340
tcaagtgttg cgcttgaacc cccacagtgg tttttctctc tttcgagaag ggttggtaa   5400
gatcttttcg gggaagatgt ttaacttttc aattgctcgt aaccttactg acacactcca   5460
tgcggcccag aaaacgactt cgcaggagct aaggtctgat atccccaatg ctctcagtaa   5520
tctctttgga gccaagccac agaccgaact gccgctgggt tggaaagggg agcccttgtc   5580
aggagctccg gatcttgaag ggatgcgagt ggctgaaacc gataagtttg ccgagggcga   5640
aagccatatt agtataatag aaactaagga taagcagcgg ttggtagcta agattgaacg   5700
ctccattgcc gaggggcatt tgttcgcaga actggaggct tataaacaca tctataaaac   5760
cgcgggcaaa catcctaatc ttgccaatgt tcatggcatg gctgtggtgc catacggtaa   5820
ccgtaaggag gaagcattgc tgatggatga ggtggatggt tggcgttgtt ctgacacact   5880
aagaaccctc gccgatagct ggaagcaagg aaagatcaat agtgaagcct actggggaac   5940
gatcaagttt attgcccatc ggctattaga tgtaaccaat caccttgcca aggcaggggt   6000
agtacataac gatatcaaac ccggtaatgt ggtatttgac cgcgctagcg gagagcccgt   6060
```

-continued

```
tgttattgat ctaggattac actctcgttc aggggaacaa cctaaggggt ttacagaatc   6120
cttcaaagcg ccggagcttg gagtaggaaa cctaggcgca tcagaaaaga gcgatgtttt   6180
tctcgtagtg tcaacccttc tacattgtat cgaaggtttt gagaaaaatc cggagataaa   6240
gcctaatcaa ggactgagat tcattacctc agaaccagcg cacgtaatgg atgagaatgg   6300
ttatccaatc catcgacctg gtatagctgg agtcgagaca gcctatacac gcttcatcac   6360
agacatcctt ggcgtttccg ctgactcaag acctgattcc aacgaagcca gactccacga   6420
gttcttgagc gacggaacta tcgacgagga gtcggccaag cagatcctaa aagataccct   6480
aaccggagaa atgagcccat tatctactga tgtaaggcgg ataacaccca agaagcttcg   6540
ggagctatct gatttgctta ggacgcattt gagcagtgca gcaactaagc aattggatat   6600
ggggggggtt ttgtcggatc ttgataccat gttggtggca ctcgacaagg ccgaacgcga   6660
ggggggagta gacaaggatc agttgaagag ttttaacagt ttgattctga agacttacag   6720
agtgattgaa gactatgtca aaggcagaga aggggatacc aagaattcca gtacggaagt   6780
atccccctat catcgcagta actttatgct atcgatcgtc gaaccttcac tgcagaggat   6840
ccagaagcat ctggaccaga cacactcttt ttctgatatc ggttcactag tgcgcgcaca   6900
taagcacctg gaaacgcttt tagaggtctt agtcaccttg tcacagcaag ggcagcccgt   6960
gtcctctgaa acctacggct tcctgaatcg attaactgag gctaagatca ccttgtcgca   7020
gcaattgaat actctccagc agcagcagga gagtgcgaaa gcgcaattat ctattctgat   7080
taatcgttca ggttcttggg ccgatgttgc tcgtcagtcc ctgcagcgtt ttgacagtac   7140
ccagcctgta gtgaaattcg gcactgagca gtataccgca attcaccgtc agatgatggc   7200
ggcccatgca gctattacgc tacaggaggt atcggagttt actgatgata tgcgaaactt   7260
tacagtggac tctattccac tactgattca acttggacga agcagtttaa tggatgagca   7320
tttggttgaa cagagagaaa agttgcgaga gctgacgacc atcgccgagc gactgaaccg   7380
gttggagcgg gaatggatgt gacaagtgcc ccctaagcct tgagttgata tatccgagaa   7440
taggttaaga tttggcaatt gcttaacaat aattattttc ttattaaaaa tacctaacac   7500
aaaaaatacg ttatatatac aaatgaaaat ttccagtatt aatctcaaca agtttctcta   7560
ccggagaata ttaatctgga atgtgtaata gagaaaattt ttgatgctat caaattttcc   7620
ttttttgcag aaatatccaa tgtataggta tgataggagt tattgggaat ttttgttcga   7680
gtgctgcccg tctgttccgg gttcacccat caacgattga acgtcttatt gcaatgtacc   7740
gtttatctgg aatataaaat tcataccgct gttaattccc tgaataagga taaataaatg   7800
atcggaccaa tatcacaaat aaatatctcc ggtggcttat cagaaaaaga gaccagttct   7860
ttaatcagta atgaagagct taaaaatatc ataacacagt tggaaactga tatatcggat   7920
ggatcctggt tccataaaaa ttattcacgt atggatgtag aagtcatgcc cgcattggta   7980
atccaggcga acaataaata tccggaaatg aatcttaatc ttgttacatc tccattggac   8040
ctttcaatag aaataaaaaa cgtcatagaa aatggagtta gatcttcccg cttcataatt   8100
aacatggggg aaggtggaat acatttcagt gtaattgatt acaaacatat aaatgggaaa   8160
acatctctga tattgtttga accagcaaac tttaacagta tggggccagc gatgctggca   8220
ataaggacaa aaacggctat tgaacgttat caattacctg attgccattt ctccatggtg   8280
gaaatggata ttcagcgaag ctcatctgaa tgtggtattt ttagtttggc actggcaaaa   8340
aaactttaca tcgagagaga tagcctgttg aaaatacatg aagataatat aaaaggtata   8400
ttaagtgatg gtgaaaatcc tttaccccac gataagttgg acccgtatct cccggtaact   8460
```

-continued

```
ttttacaaac atactcaagg taaaaaacgt cttaatgaat atttaaatac taacccgcag   8520
ggagttggta ctgttgttaa caaaaaaaat gaaaccatcg ttaatagatt tgataacaat   8580
aaatccattg tagatggaaa ggaattatca gtttcggtac ataaaaagag aatagctgaa   8640
tataaaacac ttctcaaagt ataatgtatt ttggaaatct tgctccagta tgggaatacg   8700
gttcagttct ttctggctca tggtcaccaa catagacgct tcggattgcc tgcctgtgaa   8760
gaaacagatt aactggggtt ctacgccgga atcccagatt tttccgtcac cccagtttca   8820
gcgctgctag agtacgggtg gtatgagccg ctagcagaag ctctaaatag taacttcttc   8880
caatggccga aaaagaaagc gttaaaaaat cacagtacgg gcatttctcg ggtttacgtt   8940
atttgtgcag aacgcacaaa tcaggttatt agatattatt gcttatgaac gggtagtatt   9000
cagcgaaata cagctcctaa ataactgcgc caaatagtag atcactgagg gaactcaatc   9060
cggtttaagc gatctgatca atcgctgaat atcccaaatc accacaaccg gactgagtta   9120
tgccgatcat agcaccgata cccagaaata aacgacatca gatggaaaaa attgtccata   9180
aaacagcaga caaaaaccat tccagacatc tcatcgctga tccctcccca atatccgtac   9240
caggctaaat cagagatccg gaccttttttg atgacttcgg gcaaattctg ccggagtcag   9300
gttatttaac gaagaatgcg gacgaaaatg attatattct tgccgccatt gttcaatttt   9360
ctcctgagca tcttccagag aaaggaaccc gtgcacgttc agacattcat ccctcagact   9420
gccattaaat gactcgataa aggcattatc tgtaggcttt ccggggcgtg aacagtccat   9480
cgtgaccctg ttttcatacg cccatcggtc catcgacttc gagatgaatt cgctgccgtt   9540
atctgtctgc agcctttgtg gaatacgccc cagcgaatgt tttaatctgt ccatgacagc   9600
cacaacatca tctccacgta accccctgacc gacctcgagc gccagacatt cacgactaaa   9660
attatccact atagttagcg ccctgacccg atgcccgttg aacagattat cagcaacgaa   9720
atccatgctc cagcactgat ctaacgcggt cacttctgga cgtgcgtgcc tgtgcctcgt   9780
tgtcacatgc cgccgtggac gtttcgaacg tagattgaga ccctcaagat aatcgcacgg   9840
aaaactgcat ccgtccggtg gccgtaggcc gcaagaactg gttgttcgca gggtcattgc   9900
gtgccgggca acggatggcg tccatcctga gtctgctgga aaccgccaaa ctcaacggcc   9960
acgaccctta tgtctggctg cgcgatgtac tgacccgctt gccgacctgg cccaacagcc  10020
agctcaacgc gctgctacct tacgccgaaa accgcttcag ctaattaccc cgccagctta  10080
ttgcattatt ttaatcgagc aacgcgagtt caccgttcgg ttacagtatt accatctgtt  10140
cccgcttaat tttttaaaaa atttaaggta acaatgagta tatatcttat gggaaaagcc  10200
aaaaaactaa cgaacactat aataattcga ttaacattaa tgaaaataca cggctcacct  10260
attattaaaa taatacgact agcattataa gaaaaaatat tttttatgtt tatagtatag  10320
gcgtgtattt aattaaggag ggaagcatga acttatcatt aagcgatctt catcgtcagg  10380
tatctcgatt ggtgcagcaa gagagcggtg attgtaccgg gaaattaaga ggtaacgttg  10440
ctgccaataa agaaactacc tttcaaggtt tgaccatagc cagtggagcc agagagtcag  10500
aaaaagtatt tgctcaaact gtactaagcc acgtagcaaa tgttgttcta actcaagaag  10560
ataccgctaa gctattgcaa agtacggtaa agcataattt gaataattat gacttaagaa  10620
gtgtcggcaa tggtaatagt gtacttgtca gtttacgtag tgaccaaatg acactacaag  10680
acgccaaagt gctgttggag gccgcattgc gacaagagtc gggagcgagg gggcatgtat  10740
catctcattc acattcagcc cttcacgcac cgggaacccc ggtgcgtgaa ggactgcgtt  10800
cacatctaga ccccagaact ccaccgttgc caccgcgtga acgaccacac acttctggcc  10860
```

-continued

```
atcacggggc tggcgaagcc agagccaccg caccaagcac tgtttctcct tatggcccag  10920
aagcgcgcgc agaactcagc agccgcctca ccacattgcg caatacgctg gcgccagcaa  10980
cgaatgatcc gcgttactta caagcctgcg gcggtgaaaa gctaaaccga tttagagata  11040
ttcaatgctg tcggcaaacc gcagtacgcg ccgatcttaa tgccaattac atccaggtcg  11100
gtaacactcg taccatagcg tgccagtatc cgctacaatc tcaacttgaa agccatttcc  11160
gtatgctggc agaaaaccga acgccagtgt tggctgtttt agcgtccagt tctgagatag  11220
ccaatcaaag attcggtatg ccagattatt tccgccagag tggtacctat ggcagtatca  11280
ctgtagagtc taaaatgact cagcaagttg gtctcggtga cgggattatg gcagatatgt  11340
atactttaac gattcgtgaa gcgggtcaaa aaacaatctc tgttcctgtg gttcatgttg  11400
gcaattggcc cgatcagacc gcagtcagct ctgaagttac caaggcactc gcttcactgg  11460
tagatcaaac agcagaaaca aaacgcaata tgtatgaaag caaaggaagt tcagcggtag  11520
gagatgactc caaattacgg ccggtaatac attgccgtgc gggtgttggc cgtactgcgc  11580
aactgattgg cgcaatgtgc atgaatgata gtcgtaatag tcagttaagc gtagaagata  11640
tggtcagcca aatgcgagta caaagaaatg gtattatggt acaaaaagat gagcaacttg  11700
atgttctgat taagttggct gaaggacaag ggcgaccatt attaaatagc taatgtaaat  11760
atttattcct atgagtaaat aaaattacta agagatatac accactttgc caatcaaaga  11820
aactttaaac ctcaactaaa gtaagcaatt agttgaggtt tatctgctgt agaataattt  11880
ttaacaaaaa tataaacaac aaaattaaaa gttatgtgtc tactttatgt aaccaaacga  11940
gcctgtccat aattctgtgt aatcgccact gtattaaagg tgatcgttta gacggtcacc  12000
gaactcgata ataaaacgac tcattgccaa ccgccagttt tgtattggca tgctccattt  12060
tttcgaagca tcccggatag ccagataaat aaccttccgc accgagtcgt ccgtcgggaa  12120
tactttgcat ttctttatcg cctgccggat cacactgttc agtgactcaa tggcattcgt  12180
ggtgtagatg gccttgcgga tatcgggcgg atagccgaag aaggtattga gatttcccca  12240
gtgtgtatgt agtccctcct atttttagta ccaccgccag tgaggatctc catccagttt  12300
ttgtcttgca tagataacgg gtggcatatt acccagtgag ctatgcgggc gttcttcgtt  12360
atattccgtt cgccagtctt ctgtaagcgt acggacttcg gacagtgaac ggaacaaata  12420
catatcaagt atcactccgt gatgttctgc ccattcaacc agtgctgcag caataaattc  12480
tggaccgtta tcactccgta taaaagcagg atagcctctt tctgtactta atcgctccaa  12540
aatacggacc actcggtgta ccggtatatt caagtcaatt tcaattgcca gtgcttcccg  12600
gttaaaattg taacgaacgg tgcaatagtg atccacaccc aacgcctgaa atcagatcca  12660
gggggtaatc tgctctcctg attcaggaga gtttatggtc acttttgaga cagttatgga  12720
aattaaaatc ctgcacaagc agggaatgag tagccgggcg attgccagag aactggggat  12780
ctcccgcaat accgttaaac gttatttgca ggcaaaatct gagccgccaa aatatacgcc  12840
gcgacctgct gttgcttcac tcctggatga ataccgggat tatattcgtc aacgcatcgc  12900
cgatgctcat ccttacaaaa tcccggcaac ggtaatcgct cgcgagatca gagaccaggg  12960
atatcgtggc ggaatgacca ttctcagggc attcattcgt tctctctcgg ttcctcagga  13020
gcaggagcct gccgttcggt tcgaaactga acccggacga cagatgcagg ttgactgggg  13080
cactatgcgt aatggtcgct caccgcttca cgtgttcgtt gctgttctcg gatacagccg  13140
aatgctgtac atcgaattca ctgacaatat gcgttatgac acgctggaga cctgccatcg  13200
```

-continued

```
taatgcgttc cgcttctttg gtggtgtgcc gcgcgaagtg ttgtatgaca atatgaaaac  13260
tgtggttctg caacgtgacg catatcagac cggtcagcac cggttccatc cttcgctgtg  13320
gcagttcggc aaggagatgg gcttctctcc ccgactgtgt cgccccttca gggcacagac  13380
taaaggtaag gtggaacgga tggtgcagta cacccgtaac agtttttaca tcccactaat  13440
gactcgcctg cgcccgatgg ggatcactgt cgatgttgaa acagccaacc gccacggtct  13500
gcgctggctg cacgatgtcg ctaaccaacg aaagcatgaa acaatccagg cccgtccctg  13560
cgatcgctgg ctcgaagagc agcagtccat gctggcactg cctccggaga aaaaagagta  13620
tgacgtgcat cttgatgaaa atctggtgaa cttcgacaaa cacccccctgc atcatccact  13680
ctccatctac gactcattct gcagaggagt ggcgtgatga tggaactgca acatcaacga  13740
ctgatggcgc tcgccgggca gttgcaactg gaaagcctta taagcgcagc gcctgcgctg  13800
tcacaacagg cagtagacca ggaatggagt tatatggact tcctggagca tctgcttcat  13860
gaagaaaaac tggcacgtca tcaacgtaaa caggcgatgt atacccgaat ggcagccttc  13920
ccggcggtga aaacgttcga agagtatgac ttcacattcg ccaccggagc accgcagaag  13980
caactccagt cgttacgctc actcagcttc atagaacgta atgaaaatat cgtattactg  14040
gggccatcag gtgtggggaa aacccatctg gcaatagcga tgggctatga agcagtccgt  14100
gcaggtatca aagttcgctt cacaacagca gcagatctgt tacttcagtt atctacggca  14160
caacgtcagg gccgttataa aacgacgctt cagcgtggag taatggcccc ccgcctgctc  14220
atcattgatg aaataggcta tctgccgttc agtcaggaag aagcaaagct gttcttccag  14280
gtcatcgcta aacgttacga aaagagcgca atgatcctga catccaatct gccgttcggg  14340
cagtgggatc aaacgttcgc cggtgatgca gcactgacct cagcgatgct ggaccgtatc  14400
ttacaccact cacatgtcgt tcaaatcaaa ggagaaagct atcgactcag acagaaacga  14460
aaggccgggg ttatagcaga agctaatcct gagtaaaacg gtggatcaat attgggccgt  14520
tggtggagat ataagtggat cacttttcat ccgtcgttga caaaaatctc cactacattg  14580
aataatctga acctccgacc gtctgtcagg gcatcactca taaaatcgac tgaccagcag  14640
tggttcattt taagtggaat agccaaaggt tgtggatgcc gattgggcag gcgcttttta  14700
ccttttcgcc gaaagttaag cttcagtaag cgataaacgc gatatacccg ttttacattc  14760
cacggtaatc cagactgccg taacttattg aacataagac caaagccata tgccggatat  14820
tgatgtgcca atttttgtaa tacctcaaca accggtatat ccctcgcggt gttaggacaa  14880
taatgcagca aacttcgact gatacccata atccggcacc cgcgccgttc actggcctga  14940
tattccgtca tcacgtaacg caccagttcg cgcttttcag gtaccgttaa agtttttttg  15000
ccacgacatc cttaagaatt tcatgatcta aactcagaga ggcatacatc tgctttaatc  15060
gtcggtttc ctcttcccgc tctttcattc gctttatatc agaggactcc atgccaccat  15120
atttggattt ccagttgtag taactggctt cagatccgcc gttctcgcga cagacatcct  15180
tcacatgccg gccaccttca acttctttta gaacccgcag gatctgagtt tcagtaaaac  15240
gtgctttctt cataatgacc tccgctgatt atatattaac cagagaactc cattaaacga  15300
taagactaaa ttcagggggg actacaagat aacggggagt ggacaatacg ttaataatgc  15360
gttattcatt tcaatacgca aatgtaattt aaactaatta tcatttagat aaatacgttt  15420
ttaattccaa tgccccgccg gcatggcgta aaaatataaa gtatccatcc ccccaaaccc  15480
tatttattag caataaggtc agctagccca ctggtaatgc aggaatacca gagatagcaa  15540
cgaatattga ctgggatgac atcaaaataa ccataacccg gcagtcgcta caatgtgatc  15600
```

-continued

```
tttcatccta attctctcaa tttatatgag gagcagactc tactgataaa tacccccact  15660
tcaggggatc accgaaggag gcgtattatt attctaaatt ggctcagggg aaagaattga  15720
tacatgactc cttgaaaaat ggttacgtaa atcaacctgg gggatattat tgcctcaata  15780
tacagtagat atatattatc tcagccgtca gccgccgtat cctggcgcat ggcggcttct  15840
agcaataatt tagcatcgct aagcgagagt tgttcagtac gcaagccggt cactatcact  15900
tcccctgcct tgccctgctt tagttccaaa ttagaaacgc gtggtaataa gcaggcaata  15960
tcgtgacgac tgagagccgt atttttcaca tgttccagca cctcattggc aaaggctttt  16020
tcggcggtag atatctgatg actattctct gtgagtgggt tagtttcagt gagacgaccg  16080
gcctgccccc cgtgtcccac ttgggtaatt tgttgattta ttaacgattg aagagtattg  16140
attttcatcg agtctcctgt cgctataatt gtctctacga tattctaagt tatttatttt  16200
tgctaaacta ctgtcgtaga cgatttattt ttttaatcgg cttttaaaca gaaaatcaca  16260
ataaaaaatt atttttggga atcattctca taaaacgagg atgaaaaatc caatttaggt  16320
agataactca atcttataat agataacact aaacatatat cgatagttat tcctattctg  16380
taactttcat ttgtcctaaa gtggtagata ttgcccgaga aagtgcttca atttgcccat  16440
caatactcgc gtcaataata cctacctcag tctctaatat acagcccccct tgatccaaac  16500
gcgcatcggc agtcacctct aaatagctta tttccgggaa gtctttatgt actttagcta  16560
tttgttcacg aatagctcct gcctgatcag ggttgaccct gaccacgact tgcttctgat  16620
tactcaccaa ggctaaagcc tcccgcacaa cttgcagtgt catagccact tgatcatagt  16680
cattgaggat tttacgtacc gccaaaagta caacttcact catctgttgt tcgacgtggc  16740
gataaaattg ctgacattgt aactgtgttt catgaatcaa agtcgcctgt aaggtacgcg  16800
cctcatccat gccagcctgc catcctaact gcttttgttg ctcataaacc tcttgggcgt  16860
cagccaggat cttttcagca tcctgttttg cggcactaat caactcttcg gttgttaaac  16920
tggattggta atcttcggcg cgcaaaatac gcagaccgca agcgagcgag agattacttg  16980
gtattatttg aacaaatggc tgcatgtagg cgtaacctgt ttgacaagtt tgtgacataa  17040
agtttgggcc agtgggcgtt gtgactcggc cactaaccaa ggttctgacg gcgtagctaa  17100
tgggaggcgt aaactgagcc gtttacacca tgcctgaggt tggggttcca ttgctgctaa  17160
ccaaaaagcc agccccgact ggatcatggt acggctctct atttctgtcg gcagcgggcg  17220
ctgccagtga gtgggccaag gcccgattag cagctcatgc tgtacaataa tttgccttaa  17280
tgtttcttga ttaaccaatg tcaataattg ttgtaatggg gaggccagta cacaacggcg  17340
aatcgcctcc ccatgcagaa ctaatccaag gcgacaaagt aacagttcga gctgtgattg  17400
aggctgcaaa ggcagcgccc ccagcccatg gggctcttca tagtcggtat caagagaaaa  17460
ttcatccaat aaagcagcat tgagatgagc actatcgcgc cactgaggta agtagggcaa  17520
tattgaacgc cataatgatg gtaactgttc caagtgcaaa taagccgcgg ggcagaagcg  17580
caattgaaaa gaggtaatat aattttccat catcacttct tgcgttgtaa ccaaaaatat  17640
tgagcaagat tggtcactgg caaaagcaaa ataagcaacg acaacaagcc aataagatgc  17700
ccttttgact cttcactcac ttgaattgac agtatgctcg tgttacgagg taaatgagag  17760
ctttgacgaa catctaccga tggcaccaaa atgacactga tgcgatcata ggccagcccc  17820
tcaatactat tattcactaa ttgtttaatc tgaggtatgt aggtatcaaa ctgaatatct  17880
gctgcatgct tgataaaaac cgaagcggat gctgctacac ccttcttacc tttgttattt  17940
```

-continued

```
tgctcttcag gcaatacgac atgcactcga gccactaata ccccgtcaat ttcagataaa  18000
gtgcgggaga tctcttgcgc cttggcataa ttaagcctcg ccaactcttc tatcggtgaa  18060
gatatcaacc catctttggg gaacacatcc tgtaacgtgg agaaactctc gtgtggatag  18120
cccttccgtt tgagaatatc aatagcctga gcgacatctg actcctcaac caagagctta  18180
atcttcccat ctttgtctgg ctctttgtct gcggaaaggc cttcttggcg caacagcgca  18240
agcatttcgt tcccttcctt ctgactaatt ccggtataaa gatcaacttt gcaaccagtt  18300
aaaaacaaga ttaatatcaa tgttgacagt gaagtcttaa ctttcactag ttttcacccc  18360
cccttcgaca aggtttcaac attttggctc attcgcccgg cagtcttggc gataagttct  18420
tcttggattg ttatacggat aagtgaccat tgcattagca tcaggtcgtt gggattatca  18480
actgaaacag ccagcttagt gtgtaagtca cttttaaccg tcttaaaaga cttctgaata  18540
tcactaacct ccttgaggag tgaatggccc agtccctgcg tatcttctga cattgccgca  18600
tcaaagcgca ttatttggtc agttgttggc tctgccggcc ctaattcctc cagcgtggtt  18660
atgatcacct catcggcctg agctatttct atgttcggca tttatgtatc catatcaatt  18720
tgatggctgt tatgaagtag gctatctaca atcgagttag acggtaatag gatcattaat  18780
tctttattta ttaactctga taaataaggt aatccaacct ggctctcatt gggttttata  18840
ccctctaata cttggagcaa tattgcttcc caccgcttac caaacgagtc aaactgctgc  18900
aatacactac gcaattcagg taaatctata gccggtacaa cagacccttg atgttgaccg  18960
aaacgcgcca gtaacgcctc acgtactggc gtcgccaaaa cctcaagaac ggcatggtca  19020
ggagggttac tggcataata ttgctgccac agaacttccc gtgtcttttc agcggattca  19080
ctttttagct tattctccag ttgtgttttc agctcagatg ctaccggttg tagcgtagag  19140
actgcctgag acgaagacat caacgatgta atggaacctc tattaagggt aaccgtcatg  19200
tttttagttg ctccctcatt ccattcacaa atgtctgtat tctaggatcc tgactccttg  19260
cgagacgatt taaacgtgac tctaaggcgc tccccaaccc gaggcgatat tcacataagg  19320
ctaaccaagg ttccaaatca ggataagcta atttatttcc ttgttgcaag gcgcttgcgt  19380
agtccccacg gttcatcaaa gaggaaaggc gaatcaattg aaccgcctct tcttcacctt  19440
tcaaatgtaa ccattcagca atgcaattcg cttcttcgtg gtagtggttg ccggttccaa  19500
tcagagcaat ctctgctaac agtacgttga gtttatattt catattatgg gaacttctgt  19560
aggatgcctt gcattaagtc tttcatgcta cgaactatgg ttgagtttat attgtaaatt  19620
accgaccatt tattaattga atgttgtaag tcagcaagta gcgccgggtt gtcaggctta  19680
tctttcaatg ctgctatcga gtcattaacc gctttgtttg catcgtctgc tggcttcttg  19740
agcgtttgag ccaccgcatc taagtctgcg atatcggttc ctttcgtaaa tccagagaag  19800
ttactcattt attttaggtc tcctgctaca taatgaataa tggctatagc tgactcaaga  19860
gctttagatt ctctctgcca aacctgatac tgcttggcat caccaccgcg catcatatct  19920
tttttgagct tagttagtgc catttctagt tgcatggtga tagagcgcac tgtctccacg  19980
ttatgcagtt gctcctctaa ttgtgtcatc gaggtttacc tccattgagt tggatcacaa  20040
attcccgttt tcctttactc acaatcaccg catcgcgtcg aatagccaga atacgaacgc  20100
cattgttaag tatggcacct tctggatagc gttgatgatt gtcgagtacc acataaggca  20160
ctttccctaa cgagatagct tgcacctcga aattcaattc atcatgctgg ggttgccccc  20220
cgacattgac cagttctaat ttaggtcgat tgccaaactc ttggcgaaaa gtttgttgta  20280
gttgattaaa tgaattcaat ttttcatcat tgacttgccc gcgtaattca atcagctcac  20340
```

-continued

```
ctttaacatt tacagtgaaa tctgaatcca gaccaaattg ttcaagtaat gcatcaagcc  20400
gcttgcgttg attaccggca atccgcactt tactttctac accgagcagc cctggcactt  20460
cagcttgcag caggctatca attttttgct tttgtatttc ctctgacact tccccattca  20520
attgtagcca tcccgcttgc ggtgctaaag aaacctcaat tccatggtat cccaaccgtt  20580
gcaggatgaa ttctgccccc tgacgcagtt cttccatgct gcgcagttca agccggaatg  20640
gaatgccatg gctctcaaga aaattttgca gtgacaagcg ggcatgatta tcctggatat  20700
aaccagttaa taaccaaggt tcaccctctt ttttgggcga tgttaaaacg acatccttgt  20760
aagcagcagt tgccagcaag cgccgtactt cttgctcaac aagttgtcca tcctggttat  20820
actcgcgcca caatccgtgc cctagcagcc ccaaaaaagt caaaagcaac aataaagaaa  20880
gaactccaag cccaatccca agtcgtgaac gaggtaacct gtcggttggc tcttttctct  20940
gcgtgggaac ctgtaacgtc tctggcaaag gttgccctac ggcgacaaat gtccacagta  21000
aaaaacctac ttccagacaa gagcccgcgc gaagaagagt ccccaacggc acgggaagcc  21060
cttcttgtag tagaggttct gcagaatcag ttaggcgaat accttcttca tcgaccatca  21120
gcactaaatg cacgggtgct atttcgctgt cagaaagaac aatatctgac tgcaacgggt  21180
ctgaaccaaa aacacagcgc ccatgaggaa gctcaacttc aacaccacgg tgcttccctt  21240
gataaaaacg acagacccaa ctcacaatac gccacgctta ggcgctgaaa cacaccatga  21300
ttccgcggga gtacaagcac cttcaaccac gcgccatccc aaacttttgt ccatcttgca  21360
ctgagtaaga taggatgatt tattgttttg actcagccat ttctgcactt cttgcgcttt  21420
gtttaaaggc tgacactgga agccacctaa taacttattc aaggtagtgc tttgattaga  21480
tatttcatca acagctaaga taccagtacg tagatcccga ccattaccta acgctaaatg  21540
atgcgcaata ccttcgtcaa taatccgtgg ttcgatgata aacagccgta ccgtacggcg  21600
agttaactca cttttacggc ggaaaagtgc gccaagataa ggaatatcac caagcaaagg  21660
caccttacta agagcaacac tcaattcgtc acgataaata ccaccaataa tcaaactctg  21720
gccatgtccc acgcgagcga cagtatcaac gaccgtacga ctgatagtgg ggattccgtc  21780
aatccctgaa ctattcggtt tttggttccc atcctcaatg tgtagattga gactgatttc  21840
tgacttatct ccttgagtca gcacccttgg tgtcatacgc agcatagtgc cgtaggtgat  21900
ccctttcagt tcagccactt ctttacctgt cactttgacg taataggttt catggtgatc  21960
aatcaccgct tgggcatttt cttgtgttag cagggtcgga cgtgaaacaa cttgagccga  22020
accttcattt tcaagtaaat tgactcttgc taataggtag tcaagcccgc gagcatcaat  22080
caaactaccc aatgcaccgt ttgaagcgat gttactttga tccccggttg tttttattac  22140
cacctgatga ttgttgccag tacgaatgcc aactcgccag tccacaccta attcagtaag  22200
ttggtcggca tttatatcga caatggataa cgccacttca atacgagcgc taggtttatc  22260
aagcgcatga attaaccgtt gatacattgg catacgctca ggagaatcgc gcactattat  22320
cgcattgagc gatggatccg cttcaacctt ggcttgagct gaagcccggg tagcggcctg  22380
cggtattctc tgattatcca ctgtcacttg ttggattgtg gcatcgctta acacgcgttg  22440
aagtatcgtt gcaaccccag gagcagccac ttcgtcatca cggtaatgaa tagttcgatc  22500
gctcgctgat gcatatttga gagggaaaat ctcaatcgct aatgcccctg ttttttcact  22560
gcgaatttgc gtctgttgtt ccaatgcggc tgcggtctgt tcaaccaatt caagataacg  22620
aggaggacca gagacgtaaa caaggcggtt gctagcatca gggcgccagc caaaacgagg  22680
```

-continued

```
ctcccatata ccagaacgtt gtaatgccag ctttaactct gcggcctcac tttcctgtaa  22740
acgaatgaga cgagacgcta cctcactatt tttaaaaatg tagagcacat tgccatcata  22800
gtaccaaacc aaattgtaaa gggaggcaat atgctgtagg aaatcctgag ggttatcatg  22860
ctcaaactgg ccggaaactt tgtcattaat cttatcgctt actaccactg tagcatcata  22920
attagcgctg aaatcaatta ataaatcgcg taaactttcc cccttcgcca cataaacata  22980
aggtataggc aaccaatcaa gttcttgcgc ccagctatag ttagaaagta acagtaacgt  23040
cccggtgagt acgcgcttga aaaaagaatg tagcggaaaa gccatattac ttaattccac  23100
cccacgcgag acgctacaga aaatggtgtt aactgaggaa ttaaatgttc tagcagagcc  23160
agttgtttat ttattacttc ttgcaatccg tgagtatcaa gctcttgtag acgtaaacgc  23220
gcctccagta ccaattgacc acaatcatcc aatactaaag tttgagggta acgtttagcc  23280
catgccaacg cttgttgcat tagggagcga agcaatgtga cgttaacgtt atttccttca  23340
cgtaacattg gtgcgtcaat aggagtgcgt aataccagtt ctgaaccatg cggagccagc  23400
atgacaagat gcttatctat agttaaacgg taaacacctt gtttatcggc aacaaacggt  23460
tttcttccta aactggctgc caagtttttt agtaaatttt gcattatttc tcggatggtt  23520
atatataaac taagtaatcc tgcgccaaat aaataaccta cttcatgtca tcgtgacata  23580
aggtttcgcg gttcagctca aacttccaga tattcaaaaa aatgttcatg ataattatca  23640
accacctgta tagcaataga tgatattacg ttaatcgaac taatgagact tgctctattt  23700
gatggaggtc gtttcttgcg ccaccgcact taataaacca gataagctat attgattatt  23760
aaacaacata ttattgccat ccagcggcga aacaatactg ttctatgttt cgttgaaatt  23820
tggctcatcc cattgaatct tcacaatcta atcccgtatt ttactttata gtccaaaagt  23880
gtcttttaaa aaaaacacag ataattttag cctgtggttg ctattttagt aagacgggct  23940
tggcttggag tgcatccgaa gcgacgtcga taactttgag tgaaataaga ctgactcgag  24000
aaccccgctt ccatggcaat atcaacaata ctcatcttac cattaagaag taattggtga  24060
gcatagagaa tacgtcgctc gcttatccag gcgcgtggtg aaatgccata aactgtacca  24120
aacagttctt tgaatgtggt taatcccatg ccgaattctc gcgcaaattt gcttagcttc  24180
cacccttgta gataattttc ctccataaat ttttgcaacc gttcttctgg gcggttgcct  24240
aaatggcgca gagccgagag aaataaagtc ccttgcgagc taaaggcaag caaaagcagt  24300
aattcctcaa tacgcagttg cgttaatact gacggaaaat cactccgttc caatatggca  24360
catagatttt gaatggattg tgataatatt ggtgaaatat taaaaattaa caatggtttg  24420
ggtgtggagt tgtctcgtcc aatttcacta agcaaagaac caaagcgatg caaaaaagta  24480
ctcaaaaaac tgccgggtaa tggaatccaa agtaattggc agggttcttt tgtaccacat  24540
cgaacagcat agctgccacg acgcaaaaac agcatattcc cctcatctaa atcatatgtc  24600
tgaccgctgc tctgccatga aatctgacct tgcaaaagaa tatataggcc atcttgtgaa  24660
tgctcaacaa ccttaaatat aggtgtgacc cattctaatt taataatctc tagtgatgcc  24720
ataaatgtta tactgtccta aaaatctaaa acttgtatat atttatctaa tgaggtgtat  24780
tgagttatta tgcgtgcgat gtacaaccat cgattaatgc aaccaaaacc aatataataa  24840
atcacctatc tggtattagg taactggcaa tttggataac atgttttagg tatcatttgt  24900
aaaacgactt tgtttttacc agtaagcttt tgctgagcca ccgcctgaac tcctcgctct  24960
ggaaaagaga gggttgaccg taggtaaagt tcaccttccc cgcgttgagc tggattcagt  25020
tttatagaaa agaataaagg taggttacct gtttcgaaat gagtgcgctg aacctctcga  25080
```

-continued

```
actttcccct catacaaccc aaacatacta acatcaatgt gtgctatgcg agataatggt  25140
cgtgacatac gcacctcccc cacaatacgc tgagctggca ttgggggggt agcgcacccc  25200
actaatagaa aagaaatgat gagtgctata atacgactca cgccagtccc tcccttgagt  25260
tcacacaaag aagatagcta gatgatagca atccgagttc gcgcaatatg tggtgaaatt  25320
tattattgta aaataacaac ccattcccaa ttatctcaac gggtccacca cgaactcatt  25380
taatttagct actgcaatat cacaccttgc gcatataaag ccaaacatcc tttctttcat  25440
aaaaaaagga tgtttggtta gaatcggaat cagcaaacaa acacatgtaa tagtaatgac  25500
aatactgtat tatttgtatt caacaaaaaa aagtcaagag attaatccta attagtgcta  25560
gttatgttta attgtaaaat gcacaggaga aatacaatta ccatactgta tatatggttt  25620
taaatcgcat catatattcc taatataagt gaacctcttg ttggttaacc atatcgaata  25680
aattacatat tcccaatagc cggtgttaat caccccattt ttccgataaa aacatagact  25740
agaaagtaga gaaaatagta tagaccaaca aaaatgtcat ctgttttaac catattccta  25800
gttacattgc agcctattat aacatttcgg aatgttgttt ctcgatattt tgcctttcta  25860
gccatcgtag cacttcagct gtggcctcta tttgctcagc cggaatatag tgatcgacga  25920
gcgcatccca ataaagagca cgggctaatg ggatacgttg taaaataggc accccttctt  25980
cttctgctat tttgcgcaca gtctgaactt gggcatcggt atatttgaat gttaccaacg  26040
gtagtggtgt ttcccctcgc ttgtaaagaa taccaatagc aatatgggtc ggattagcta  26100
ccaccactga tgagcgttta acattttccc gcatgttcct cgattggatc tcttgatgaa  26160
actgacgacg cttgcttttg atttctgggc taccctccat ttctttgtac tcgcgtttga  26220
tctcatcctt gctcatttta agttccttaa tatattgata gtattcaaag gcatagtcgg  26280
ctatggagat gaccacaaag ccaacagtac agataaccat caactgccgg agtatttgcc  26340
ccaataaagg ggtaatacat tcaattccac aggttggcaa ctgcaagagt gtgactagat  26400
ttcccttaat gattatccag atgagtatac tgagcaaaac aaccttgaga atggatttga  26460
gaaactccac taaacttttg atggaaaaga tacgcttggc accctctatt ggattgattt  26520
ttttaatatc cggtttaatt gcttcaccac ttataagaaa accatactgc acaacatgag  26580
atgcgatcgc cattaatgcc gccactgtta acaaaggaaa acagagataa aaaaactcga  26640
gcaacacatt gtcaaccaca tagctaagcg cctgcgagaa aggaagatag ctctgctctg  26700
cggggattag catcagctta ctaaaatgct cgaaatagta gtcagaaagc cccattaaca  26760
tcgcactcag cgcgacgata agcgcagtag agaccacttc cttacttttc gctacctgtc  26820
ccttttttgcg cgcatcacgg attttcttcg gggtgggttg ctctgtcttt tctccgctca  26880
ttacttctcc aaaacaggga tcagtaaact tataggatcc ataaccaaca gcattgcttt  26940
actggcatga ctcatcattt gcatacagta gataaccaac aacaggcttg ctatcgcgct  27000
ttttatcggc atagccagca caaagacgtt taaagaaggc gcaaaacgac tgatgagtgc  27060
aagtccaaat tcagctaaaa acatagcgat gagtaaagga gcagccaata cagcggcgat  27120
taatagtatc tggctgaatt ggttataaaa gaaatcaacc cactgttcac taactgcagg  27180
gaaaaagctg gccaccggcc aatttacata gctgtgaaag agggctgaaa gcaaagagag  27240
gaaagcccct ccgctgaaga aaattgttat taacgtttga gtcaaaagta aaccagtcgg  27300
actagtttga ctatcaagtc caggattgag tagagatgcc atcgcggcac ctctttggtt  27360
atctacaata aatcctgcgg attctaaggc ccagaaagga atggtggcca caaacccaat  27420
```

-continued

```
caataacccc agtatgatct ctttgccgat aagcagcatc aacgtaaacg catcaacctc  27480
aatataaggt tggttagcga cggcaggata gacataaaga gccaatgaac agacaatacc  27540
attacgcagc aatactccac cgaggagctg tttacttaac actggcaata taacaaaaca  27600
agccataaaa cgaggcaaca gcagggtata agtgagcaat ggtctttgga ttaaatccgc  27660
tatcatctta tgccttgtat cttcatcatg gtcatttctg caaaactgtg caattcatta  27720
ccaagccacg aggcggtagc aaacagtgtg accaccacag cgatcaattt gataacgaag  27780
cccagagttt gctcttggat ttgcgttaaa gcttgtacta aagataccaa agttcctacc  27840
accgcagcca ctaacaccgg cggcattgaa aggactagca ccagccataa tgcctgactg  27900
gtgaagtgaa ttatgtcacc ttgactcatg tcaccctccg tagctaatca ccagcccatg  27960
cgtgagtcgt gtccagccat caagtaaaac aaatagcagc aatttaaatg gcagtgaaat  28020
agtcatgggg gaaaccatca tcatccccat tgccaacaag atattggaaa taaccaggtc  28080
aatgacgata aatggtaaat agatgagaaa gcctatctca aatgctcgag tcaactcact  28140
caccgtaaac gcaggcaata aaatgaacag gctgtctgac tctaaccggt cagcatactg  28200
cttgggccat aactgtttag tgctgtcaac aaaaaaagag tattcttgcg cttgaatatg  28260
ctgcttaagg aacatgcgat agggggcaag cccttcatca aagaatttct caacagattc  28320
tatgttcgtg aggctaacct cattagcttg taaatagtct tgcgtcgcga agccaacggg  28380
tgccattaca taaagactaa ggatgattgc taagccatac attgccatgt tgggggggat  28440
ttgctgtacc ccaagggcat tgcggagtag tgaaaagacc accgcaaatt tgacaaacga  28500
tgtagccatt accgaaatca atggaagcag agtcagcaaa gataaaacga tgatgagatt  28560
aatttcatcc ggtaactgga tcatgaaatc gtaacctctg tcaggcgttc aattcgaacc  28620
ccgaggcgcc cttggatctc gaccaatcga ccatgtccaa gcaaccggcc gttagccagc  28680
aagcgcactt caccatcaac aggtgttgta agatcaataa gagaacccgg ctccaggcta  28740
gtgagtgtgt gccaatctaa gatttgccgc cccacttcaa agctaacttg aaccggaagt  28800
tggttcaaat cggtcaatgg ttcggggtta agttcgtcag attcatgact cataccgata  28860
aactccaatt tatttgattg taattgaaag tagccccaag ggttctcacc aacataggcg  28920
agtactggcg aattaggccc actcccctca ggggccaaca acacatcacc taatcgaagg  28980
gaatcaacct catctagagt caggtatact ttatgccaac gcaaagaaat aaggataggc  29040
aaaggtatgc gctcagaatt gggtcgtgcg ggtaacagag cgaacagagc ctcagctgag  29100
gttagccaga aggagatatg cgcattatct cgggacagcc gcaaactcaa cagaggttgc  29160
gtgacagaaa gagacgctgt cgctatatca ttacagacca gtttcggcag gaaaactgtc  29220
tggcgttcca acagcgcaag ttgcaactct ttcggcagag taaagaatgg agcccctagt  29280
aagtcggcgg ttaaccagtt agccagatca ttgccaaaac agtagagcgt gaagtgcgtt  29340
cccttccatt gtaactgtaa tatacagttc aaagacgaag gaggctcaga gacggtaagt  29400
tcgagttttc cctcttccca caagtagttt tgttgataat ggctgagccg ttgacgtagc  29460
gacagttcac ttaatttggc ctgtggcaag gttaacaaac tcattcttca gcctcccact  29520
cctcatagac gtggcgtttc tgacgtgact cctgttcact gtcatcgcta gcttgaaaat  29580
caagttgtgt tggctcaatg cgttgtaatc gctcaagaag atcataactt ccctgcgcta  29640
aaattcttaa agcttcccga ctggcgatca gttctacatg cagttttccc ggaatctcag  29700
caatacgaac cataatagcc cccaattcag gtaagttaag gtgtaattgg gttacttggg  29760
atgagccgcc gcgcagttct agttctaccg ctagtcgctg tgctaactgt ataagttgct  29820
```

-continued

```
ctgagactga tgccagcctg gtcgcgcgca ttgttgctaa taggtgatca cccggcgtga  29880
caaccggtgc tgtaaaagac aaggaataca tctccggcaa ggtttcttcg cgcggaagta  29940
acagtttttc tggtcgcggt ggttcgatgg tatctttgct gctatcaacg ccatcagtaa  30000
gatgttggga ccgatccgcc agctcggtca tgtccagttg ctctgactgc actgtcgctt  30060
tgtacggaaa acgagcagat ttttctgcta cctcagtcac aggagtagca caccatcttg  30120
ctaccaaatg atcatccggt gtggcactaa ctgccggggg acatatctct ggcaatgctt  30180
tttgatgaag agctaacggt tcttctgcaa ggcgtttttg cctgctatcg cgctggtttt  30240
ttgctatact ggccggagtt tccctaccga cagaccatac aataacctct gcgccgtcag  30300
cagccggatt caatggctga acagtcggct tgctattcaa ttgaactggt tgagcggaat  30360
cgataggcga ttgctgaaca aataactcat catgtccaga cggctcgcag gggggattcac  30420
ttgatgtccc cgtttcacaa gtcacccccct ctaaaaaggg cgccaatggc atgagagcat  30480
taataatact ctctacgcgg tcatcaaaac ggctatcctg ctggtataag tgcgctctat  30540
tggtagcacc ttcggcaagc ggagataagt tgaaatcatg attattctga tggttgtgtt  30600
gaggttttaa tcctacctct ttccttccgg gttgagacgt cgccgctaat ggcgcatgcg  30660
cacgcaagcc atctcctttc tgaccttctt ttttgccaag gtcatgcgga cgtacaggtt  30720
taagcgactc ttctttggga tgacaattcc ccttattatt atgcaacagc gcttgctcaa  30780
aatcgacaca tgcttgcaaa gcatgatgcg gcttccccag aggttgatac tcaggttcta  30840
atggggaacg agtggtgatt ttattcatta ggcgttcctg tgatgctgta gaaactcttc  30900
ttgttcttgt tcttcctgat aatgttgttg atttagctca tcttcatctt ctcgtcgcac  30960
tagctcgaga aacttatttt ccttatgacg agcctgttgc agcatctttt ggcataacgt  31020
aaggcgctca cgctcattgg ctaaacgttc caataatttg gcgcactcca gttcataatt  31080
ggcctccttt tcacgtagcg acgctatttg tcgctgccat ttctccaaat ctttacaatt  31140
cagtgtggtg ttttttcgct gatcaaatag acgttgctcc tcatcaatac gccacaaatg  31200
gtaatcctga ctggtttgca ccgcctcttg atgacgtcga tgagctgcct gcaagcaagc  31260
ttgctgagtc ttgatggctt tctccgcacg ttcaacgcgt aaaactttaa cccggtgcag  31320
gcggcgtatc attgggtcag cgtctccaat aagttcagcg tctcattgaa atggcttaac  31380
tcgtgcgtcc cctggcagag ccatcctcga atcgcccccca tgcgttcaat cgcttgatcg  31440
gcctctttgt cttgcccttt ctggtactcc ccgatttgca acagcaattc cacttcttca  31500
tatttggcca ataaacggcg taagtccccc gcccaggttt tgtgctcctt gctgacaatt  31560
tgattcatca ccctgctcgc tgaacgtaat acgtcaatgg caggataatg attagctgcc  31620
gctaatttcc gtgacagaat aatatgacca tcaagtatcg aacgtgtttc gtcggccacg  31680
ggttcggtca tatcgtcccc ttcgaccagt acggtataga gagccgtaat tgaccctttg  31740
ctggactgac cagccctttc catcaaacgg ggtaaagcgg caaatactga cggaggataa  31800
ccgcggcgag tcggtggttc tcccgcagct aagcctattt cacgctgagc acgagcaaac  31860
cgtgttacag agtccataag taacaatacg cgtttccctt gatcgcgaaa atattcagca  31920
atagatgtcg ccacgaatcc agctttggct ctttccattg agggccgatc cgaggtggcc  31980
accacgagaa ccgctttgcg taacccctct tcgcctaaat cagactcaat aaactcacgc  32040
acttcgcgtc cacgctcacc aataagcgcc agcacggtta cgtctacttc agcactacga  32100
ataagcgaag caagcagtgt acttttcccc cccccggcgg ccgcgaagat gcccattctt  32160
```

-continued

```
tgcccctcgc cacaggtaag caaaccgtca ataacccgga tccccaaaga aagtggtgtg  32220
gtaataagtt ttcggctcat cggcgctggg gcatcctgat aaactgggta ccaagccgcc  32280
ggttcaggga gatgcccccc atcgaaaggc tgccctaaac catccaacac ctgtcccagc  32340
agatgttcac ccaccccaac ctgatgcatt gtccctgtcg ggctaacttc agtattagaa  32400
gatatcccgt acatttcacc aagtggaata agtaatgctt gatgttgggc aaaacctatg  32460
acttcagcct gtaaagacag gctgttgtca gggttacgta agtaacataa ctcaccgatg  32520
cgcacacctg gcactaccgc ttttaataac gttcctgtca cttgagtgac acgtcctcta  32580
atttggatta ggcggctacc tacaatgcca tgacgaatat gatgaggtat ctgatctagt  32640
gagagcataa atccataatg gttgaaatat taaccactat tttagtgact aaaaacgcta  32700
aaaaattgta gcgggagccg cgagtttttta gaaaaatagc caagcagcac taaaatttct  32760
cggctgattt tggcatcgat aagcaagaac tatttttata atcgcggtaa ttgtaattat  32820
aaactgttca tctcagggag tagttatgac gacgcttcat aacctatctt atggcaatac  32880
cccgctgcat aatgagcgtc cagagattgc cagtagtcag atcgtaaatc agactctggg  32940
tcaatttcgg ggagaatctg tgcagatagt cagcggcact ctgcagtcta tagctgatat  33000
ggcagaagag gtaacatttg tcttctccga gcgtaaggag ctctccctcg acaaacgcaa  33060
attaagtgac agccaggctc gagttagcga cgttgaggag caggttaatc aataccttag  33120
caaagttcca gagttggaac aaaaacagaa tgtgagtgag ctgctcagtc tgttgagtaa  33180
cagccccaat ataagcttgt cccagttaaa ggcttatctg gaggggaaat cagaagaacc  33240
gagtgagcaa ttcaaaatgc tctgcggctt gcgtgatgcc ctgaaagggc gccctgaatt  33300
agcacatctt tcgcatttgg ttgaacaagc tctggtcagc atggctgaag agcaaggaga  33360
aaccattgta ttgggtgcca ggataacccc ggaagcgtac agagaatccc agtcgggtgt  33420
taatccactg cagccgctcc gtgataccta ccgcgatgca gtgatgggtt atcaaggaat  33480
ttatgcgatc tggagtgatt tacaaaaacg ttttcctaat ggggatatag actcggtgat  33540
attattcctg caaaaggcgc ttagtgcaga tctacaaagt caacaaagcg ggtctggacg  33600
ggaaaaatta ggaatagtta ttagtgactt acagaagcta aaggagtttg gtagcgtgag  33660
tgaccaagtt aaaggatttt ggcaattttt ttcagagggt aaaactaatg gcgtacgacc  33720
tttctgagtt tatgggagat attgtcgcac tggttgacaa gcgctgggcg gggattcatg  33780
acattgaaca tcttgccaac gccttttccc ttcctacgcc tgaaatcaaa gtgcgtttct  33840
atcaagattt aaaaagaatg tttcgtcttt tccctctggg ggtatttagc gatgaggagc  33900
aacggcaaaa tttattgcaa atgtgtcaaa atgcgatcga tatggctatt gagagtgaag  33960
aggaagaatt gagtgagttg gattgaaccc atcatttccc atttctgcca ggatctggga  34020
gtgccaacat ctagccccct ttcgcctctt attcaattag agatggctca atctggcacg  34080
ctgcaactgg aacaacatgg tgcgacactg acattgtggt tagcgcgttc tcttgcctgg  34140
caccggtgcg aagatgctat ggtcaaagcg ctaacgctca cggcggccca aaagagtggc  34200
gctttaccgc tgcgagcggg gtggttaggg gaaagtcagc tggtgttatt tgtctcgctt  34260
gatgagcgtt ccttaacctt gcccctttta catcaagctt tcgaacagtt actgcgattg  34320
cagcaagagg tgcttgcgcc gtgagtcgca taataactgc cccccatatt ggcatcgaaa  34380
aactgtcggc gattagcctg gaagagctat cctgtggctt gcctgaacgt tatgccttgc  34440
cgcctgatgg gcatccagtc gaaccacatt tagagcgcct ttaccctaca gcacaaagca  34500
agcgtagcct atgggacttt gcttctcccg gctatacatt tcatggatta catcgagctc  34560
```

-continued

```
aagattatcg gcgcgaactg gataccttgc agtcactgct aaccaccagt cagtcctcag  34620
agctacaagc tgccgcggcg ctgcttaaat gccaacaaga tgatgatcgg ttactgcaaa  34680
taatccttaa cctgttgcac aaagtatgaa tattacttta accaaacgac aacaggagtt  34740
cttgctgctc aacggttggt tacaactaca atgtggccat gcagagcgcg catgtattct  34800
attggacgcc ttgctgacgt taaatcctga gcatttagcc ggtcggcgtt gccgattagt  34860
cgcgctactt aataataacc agggagaacg tgccgaaaaa gaagcgcaat ggctaatatc  34920
acatgaccct ttacaggctg ggaattggct ctgtttgagc cgcgcccaac aactgaacgg  34980
cgatcttgat aaggctcgcc atgcttatca acattatttg gagttgaaag atcataatga  35040
atccccatga tcttgagtgg ctaaatcgta ttggcgagcg taaagatatc atgctggcag  35100
tgctgctgtt agctgtggta ttcatgatgg tcttaccact cccccccctt gtgttggaca  35160
ttctgattgc tgttaacatg accatttcag tggtgttgtt aatgatagcg atctatatca  35220
actctccttt acaattttca gctttccctg cggtgctact cgttaccacg ttatttcgtc  35280
tcgcactttc agttagcacc acccgcatga tcctgctaca agctgatgcg ggcagattg  35340
tttacacctt tggtaatttc gtcgttggcg gtaacctcat cgtcgggatt gtcatcttcc  35400
tgatcatcac tattgtgcaa tttttagtga taacgaaagg ctcagaacgt gtagcagaag  35460
ttagtgccag attctctctt gatgcgatgc cgggtaaaca gatgagtatc gatggcgata  35520
tgcgagccgg ggtgatcgat gtcaatgaag cgcgtgagcg acgcgcgacg atagaaaaag  35580
aaagccaaat gttcggttct atggacggcg ccatgaagtt cgtcaaaggg gatgcaatag  35640
ccggcctcat tattatcttt gtcaatatat taggcggcgt caccattggt gttacccaaa  35700
aaggattagc ggccgctgag gcactgcaac tctattccat cctcactgtc ggggatggga  35760
tggtttctca ggtacctgcc ctgctgatag ctattaccgc gggtattatc gtcacccgcg  35820
tctcttcaga agattcatca gatctgggta gcgatattgg caaacaggtt gtcgctcagc  35880
ctaaagccat gctaattggt ggcgtactgc tgttgctctt tggtcttatc cccggcttcc  35940
caacagtcac ctttctgatt ttggcgctat tggtaggctg tggtggttat atgctcagcc  36000
gtaagcagag tcgtaatgac gaggctaatc aagacctgca atccatactg acgagcggtt  36060
ctggcgcccc ggctgctcga accaaagcca aaacaagtgg ggcaaacaag ggccgactag  36120
gggaacaaga agcatttgct atgacggttc ccttgctgat tgatgtagat tcaagccaac  36180
aggaagcact ggaagcgata gcactaaatg atgagctggt tcgagtgcgc cgtgctcttt  36240
atcttgatct tggcgtacct ttccctggga tccatctgcg ttttaatgag ggatgggtg  36300
aaggcgaata tattatttcc ttgcaagaag ttccagtggc gcgaggtgag cttaaggcag  36360
gttatttact cgtgcgtgaa tccgtcagcc aactcgaatt actgggtata ccctatgaaa  36420
aaggggaaca tttgctaccc gatcaggaag ctttctgggt atcggttgaa tatgaggagc  36480
gcctggaaaa gtctcaactg gaatttttct ctcattccca agttctaacc tggcatcttt  36540
ctcatgtcct acgtgaatat gccgaagatt tcattggtat ccaagaaacc cgctatctgc  36600
tcgaacagat ggaaggaggc tatggcgaat taattaaaga agtacaaaga atcgttccct  36660
tacaacgaat gaccgaaata ttacaacgat tagttggaga agatatttct atccgtaata  36720
tgcgatctat tcttgaagct atggtggaat ggggacaaaa agagaaagac gtcgttcaac  36780
tcacagaata tatccgcagt agtctaaaac gttatatctg ctacaaatac gctaatggca  36840
acaatatatt gccggcttat cttttcgatc aagaagtaga agaaaaaatt cgtagcggtg  36900
```

-continued

```
tgcgccaaac cagtgcaggg agttatttgg cattggagcc tgctgttacc gagagtttac  36960
ttgaacaagt tcgcaagact attggcgatc tatcgcaaat ccagagtaaa ccggtgctga  37020
ttgtttctat ggatattcgt cgctatgtgc gcaaactgat tgagagcgaa tactatggct  37080
tgccggtact ttcataccaa gagctgactc agcagattaa tatccaacca cttggacgaa  37140
tttgcttatg atggcagatc ctttaattcc gtggcttacc gaacatggct tggtttgcca  37200
ccctcatact ttgtctggca cccccatttc tttaggttcg gcctttcaat tagctggcct  37260
caagcttgcc tggcgcgtag aaattgaaca aaggcgggtt tggatcgtgc ttatccaacg  37320
agtggaacaa cgtcgagggc tgaaaaatcc cttcgcggca ctttatatgt tagctaatgc  37380
agcgcgggcc gttcttggcc ctgactatta tctgtatggc aatgtcgatg tactggcggg  37440
gagttctctc agtacgcaac ggctcgctca tttttatcgg cgttggaccg gggccaaaga  37500
attaagcacc gggtggttct cactaaaagt atcacaagtc atcaccttat ctaatatgaa  37560
aaagcgacaa aacaacggct ttgcctgaca agctaaataa aaataacgta atagaatagg  37620
aggtagatta tgaagtcttc ccattttgat gaatatgaca aaacgcttaa acaggcagaa  37680
ctggcaatag ccgacagcga tcaccgcgca aaattattgc aagaaatgtg tgctgatatc  37740
ggcttaacgc ctgaagccgt aatgaagata tttgcgggcc gttccgccga agagataaag  37800
ccagcggagc gcgagttgct tgatgaaatt aagcgtcaga gggagaggca gcctcaacat  37860
ccctacgatg ggaagagacc aagaaaacca acgatgatgc gagggcaaat tatttaatat  37920
gattagagcc tacgaacaaa acccacaaca ttttattgag gatctagaaa aagttagggt  37980
ggaacaactt actggtcatg gttcttcagt tttagaagaa ttggttcagt tagtcaaaga  38040
taaaaatata gatatttcca ttaaatatga tcccagaaaa gattcggagg tttttgccaa  38100
tagagtaatt actgatgata tcgaattgct caagaaaatc ctagcttatt ttctacccga  38160
ggatgccatt cttaaaggcg gtcattatga caaccaactg caaaatggca tcaagcgagt  38220
aaaagagttc cttgaatcat cgccgaatac acaatgggaa ttgcgggcgt tcatggcagt  38280
aatgcatttc tctttaaccg ccgatcgtat cgatgatgat attttgaaag tgattgttga  38340
ttcaatgaat catcatggtg atgcccgtag caagttgcgt gaagaattag ctgagcttac  38400
cgccgaatta aagatttatt cagttattca agccgaaatt aataagcatc tgtctagtag  38460
tggcaccata aatatccatg ataaatccat taatctcatg gataaaaatt tatatggtta  38520
tacagatgaa gagattttta aagccagcgc agagtacaaa attctcgaga aaatgcctca  38580
aaccaccatt caggtggatg ggagcgagaa aaaaatagtc tcgataaagg actttcttgg  38640
aagtgagaat aaaagaaccg gggcgttggg taatctgaaa aactcatact cttataataa  38700
agataataat gaattatctc actttgccac cacctgctcg gataagtcca ggccgctcaa  38760
cgacttggtt agccaaaaaa caactcagct gtctgatatt acatcacgtt ttaattcagc  38820
tattgaagca ctgaaccgtt tcattcagaa atatgattca gtgatgcaac gtctgctaga  38880
tgacacgtct ggtaaatgac acgaggtaat tatgcaacaa gagacgacag acactcaaga  38940
ataccagctg gcaatggaat ccttcctaaa aggaggggga actatcgcca tgctcaacga  39000
aatttcaagt gacactttag agcaactcta ctctcttgca tttaaccaat accagtcagg  39060
aaaatacgag gatgctcaca aggtctttca agctctctgt gtgctagacc actatgattc  39120
acgtttcttt ttagggctag gcgcttgtcg tcaagccatg gggcaatacg acttagcgat  39180
tcatagctac agctatggcg ccataatgga tataaaagaa cctcgttttc cgtttcatgc  39240
ggccgaatgt ttactgcaaa agggagagct tgctgaagca gaaagtggct tgttcttggc  39300
```

-continued

```
tcaagagctt atcgcagaca aaactgagtt taaggagctt tccacccgag ttagctcaat  39360
gttagaagca attaaattga aaaaggagat ggaacatgag tgcgttgata acccatgacc  39420
gctcaacgcc agtaactgga agtctacttc cctacgtcga gacaccagcg cccgcccccc  39480
ttcagaccca acaagtcgcg ggagaactga aggataaaaa tggcggggtg agttctcagg  39540
gcgtacagct ccctgcacca ctagcagtgg ttgccagcca agttactgaa ggacaacagc  39600
aagaagtcac taaattattg gagtcggtca cccgcggcgc ggcaggatct caactgatat  39660
caaattatgt ttcagtgcta acgaagttta cgcttgcttc acctgataca tttgagattg  39720
agttaggtaa gctagtttct aatttagaag aagtacgcaa agacataaaa atcgctgata  39780
ttcagcgtct tcatgaacaa aacatgaaga aaattgaaga gaatcaagag aaaatcaaag  39840
aaacagaaga gaatgccaag caagtcaaga aatccggcat cgcatcaaag atttttggct  39900
ggctcagcgc catagcctca gtgattgtcg gtgccatcat ggtggcctca ggggtaggag  39960
ccgttgccgg tgcaatgatg gttgcctcag gcgtaattgg gatggcgaat atggcagtga  40020
aacaagcggc ggaagatggc ctgatatccc aagaggcaat gaaaatatta gggccgatac  40080
tcactgcgat tgaagtcgca ttgactgtag tttcaaccgt aatgaccttt ggcggttcgg  40140
cactaaaatg cctggctaat attggcgcaa aactcggtgc taacaccgca agtcttgtgg  40200
ctaaaggagc cgagttttcg gccaaagttg cccaaatttc gacaggcata tcaaacactg  40260
tcgggagtgc agtgactaaa ttagggggca gttttgctgg tttaacaatg agccatgcaa  40320
tccgtacagg atcacaggca acacaagtcg ccgttggtgt gggcagcgga ataactcaga  40380
ccatcaataa taaaaagcaa gctgatttac aacataataa cgctgatttg gccttgaaca  40440
aggcagacat ggcagcgtta caaagtatta ttgaccgact caaagaagag ttatcccatt  40500
tgtcagagtc acatcaacaa gtgatggaac tgattttcca gatgattaat gcaaaaggtg  40560
acatgctgca taatttggcc ggcagacccc atactgttta agtttaagga ggaataacca  40620
tgacaataaa tatcaagaca gacagcccaa ttatcacgac cggttcacag cttgatgcca  40680
tcactacaga gacagtcaag caaagcggtg agattaaaaa aacagaagac acccgtcatg  40740
aagcacaagc aataaagagt agcgaggcaa gcttatctcg gtcacaggtg ccagaattga  40800
tcaaaccgag ccagggaatc aatgttgcat tactgagtaa aagccagggt gatcttaatg  40860
gtactttaag tatcttgttg ttgctgttgg aactggcacg taaagcgcga gaaatgggtt  40920
tgcaacaaag ggatatagaa aataaagcta ctattactgc ccaaaaggag caggtagcgg  40980
agatggtcag cggtgcaaaa ctgatgatcg ccatggcggt ggtgtctggc atcatggctg  41040
ctacttctac ggttgctagt gctttttcta tagcgaaaga ggtgaaaata gttaaacagg  41100
aacaaattct aaacagtaat attgctggcc gcgaacaact tattgataca aaaatgcagc  41160
aaatgagtaa cattggtgat aaagcggtaa gcagagagga tatcgggaga atatggaaac  41220
cagagcaggt agcggatcaa aataagctgg cattattgga taaagaattc agaatgaccg  41280
actcaaaagc caatgcgttt aatgccgcaa cgcagccgtt aggacaaatg gcaaacagtg  41340
cgattcaagt tcatcaaggg tattctcaag ccgaggtcaa agagaaagaa gtcaatgcaa  41400
gtattgctgc caacgagaag caaaaagccg aagaggcgat gaactataat gataacttta  41460
tgaaagatgt cctgcgcttg attgaacaat atgttagcag tcatactcac gccatgaaag  41520
ccgcttttgg tgttgtctga ccattgatga ccttggttag ttaattaacc gaaagtttta  41580
ttttacctta ccccttatgg tgatagagct tatctatata aggtataagg tgctgaaaag  41640
```

-continued

```
ccctgtatta acattagtta atccagggtt gtgattatta aattaaaaat aataagttag  41700
gatcatatga caattaaaat aaaagattat ttacatgtag tagctcaaga cctgagctga  41760
cagttaccgg ttgttgaacg gcaatacgcg gtcattgagc acgtcagcgg ctgtgatcgg  41820
cattttgctc gtatacagcg agagtgttag aaatgctgtg tcattccagt aatatgcaat  41880
caaaaaagaa tgacacatat cccaataatg agagtcggtg attttactca ttgatggggg  41940
ggaataatta ggctaaaaca acctcaatgt taaagagccg aggtgttcgg taagctctgc  42000
atttaacgct gtttcgacgg taagctttgt tagcatacga gaaaatgcat taaggtcggc  42060
ttcggtttta agacctttag ccagttcagc cgcaagtgct ttaagtttct tttcgtccat  42120
aatttgcctg tctccgttgt tggagtgaag atatcaaaaa caggcaatta cacaatattg  42180
tttacagtct cgattcataa aggtagatcc ttcccgcact caatattcag gttcgtcacg  42240
gcgtaaccaa atatcaaatt gacctttatt cagtcgttgc aatgtttcaa atccctgaag  42300
cgttgaccag gcacggtttg gccgtttgaa atccccggcc gcgtttacca attttttgat  42360
gggggcatgg tcagactcga tacgattatt caggtatttg acttgccgct gctttgcagc  42420
atcccgtatc ttttccttct ttcatcaaac gagtgatagc gtaaccgtat gacgaatgtt  42480
tatcggtatt gagtatttta ggctgtcttt caacagaata gggttttaac acccgtttaa  42540
tgaatggata ggcggtattt ttatttcgtt taggcgaaaa ataaaaatct aatgtagtgc  42600
cgtgcttatt gatggcgcga tagagataaa accattttcc gttgaccctg atatagattt  42660
catcgagttg ccatgaggag tcggcatccg taaattgata tcgtttcaat ttctgacgag  42720
gtataggtgc atattcaata aactaacggt aaatggtaga gcgataaacg gaaatcccac  42780
gctctgacag catatcgctg acattggcat aactcatcgg gggcaaaatg ttcccacttg  42840
aaatcacctg ggccatgtg gattcactga agaagggatg aatagcctca gttttcatga  42900
caactccatt ttttgcaaca agcccaaata tagtgatgct gaagtggcac aaacgctgga  42960
taccgcgcaa aagcacaccc tgacggtttc aaaaggggta ctggatacgg ccaaacagta  43020
tactaacacc gtcagcagta atacattgga cagtgccaat acctatacca ataataaagc  43080
agactaacat tgaaggatgc taataattat actgttcaga aggtaaacag agatgctata  43140
agtggtgtta tagatcagga attatattga gaaaccattg aagaaactaa agagcaaatg  43200
gccggtattg aaactactgc cccaaaatac actgatttaa agtttaatga tatttccggt  43260
aaggttgact ctgcggccat acaatacttc tgacatattt cttctggtta tttatgcata  43320
aaaatggcca aaaactttca atggtagaag agctaaattc ggataaataa cgcataaaaa  43380
ttcccggcga aaaactatat acatatataa atttaatatg tatgtttttg tttgcagtga  43440
aaaactcgat aataaaaata ttttcagaaa ggcattcaat atgttcataa atccaagaaa  43500
tgtatctaat actttttttgc aagaaccatt acgtcattct tctaatttaa ctgagatgcc  43560
ggttgaggca gaaaatgtta aatctaagac tgaatattat aatgcatggt cggaatggga  43620
acgaaatgcc cctccgggga atggtgaaca gagggaaatg gcggtttcaa ggttacgaga  43680
ttgcctggac cgacaagccc atgagctaga actaaataat ctggggctga gttctttgcc  43740
ggaattacct ccgcatttag agagtttagt ggcgtcatgt aattctctta cagaattacc  43800
ggaattaccg cagagcctga aatcacttct agttgataat aacaatctga aggcattatc  43860
cgatttacca cctttactgg aatatttagg tgtctctaat aatcagctgg aaaaattgcc  43920
agagttgcaa aactcgtcct tcttgaaaat tattgatgtt gataacaatt cactgaaaaa  43980
actacctgat ttacctcctt cactggagtt tattgctgct ggtaataatc agctggaaga  44040
```

-continued

```
attgccagag ttgcaaaact tgcccttctt gactgcgatt tatgctgata acaattcact  44100
gaaaaaacta cctgatttac ctctttcact ggaatctatt gttgctggta ataatattct  44160
ggaagaattg ccagagttgc aaaacttgcc cttcttgact acgatttatg ctgataacaa  44220
tttactgaaa acattacccg atttaccccc ttccctggaa gcacttaatg tcagagataa  44280
ttatttaact gatctgccag aattaccgca gagtttaacc ttcttagatg tttctgaaaa  44340
tatttttct ggattatcgg aattgccacc aaacttgtat tatctcaatg catccagcaa  44400
tgaaataaga tccttatgcg atttaccccc ttcactggaa gaacttaatg tcagtaataa  44460
taagttgatc gaactgccag cgttacctcc acgcttagaa cgtttaatcg cttcatttaa  44520
tcatcttgct gaagtacctg aattgccgca aaacctgaaa cagctccacg tagagtacaa  44580
ccctctgaga gagtttcccg atatacctga gtcagtggaa gatcttcgga tgaactctga  44640
acgtgtagtt gatccatatg aatttgctca tgagactaca gacaaacttg aagatgatgt  44700
atttgagtag tacgcaagag cgttcataat tctgcgtcac gttaaaatat cattacaacg  44760
taatcacttt atcgaggcga ccttcaaaat aaatcgccaa ctgtgacaat gccaaattcc  44820
agctctggat tggcattgtc catctttcct gcgcattcat taatcccaga tacagtgatt  44880
tcaacagact gttctcatta gggaaaatgc ctttcgtttt tgtcagcttt ctgaacagcc  44940
gatgtaccga ttcaatggca tttgtcatgt aaatgacctt gcggatcgtt gtcggatacc  45000
ggaagtaaca cgacaaattg gcccattttt tccgccacga ctggagtacc actggatatt  45060
gttggcccca ttaccagttg aggctcaaaa gttccattgc gatcacgggg cgtggcgagt  45120
tcaaacgtac cagtgggagt tttgaccgtt tttctggacg aaccattttt gcggttggct  45180
tcgatgtcca gagccagatg agtctgacca tgcccccatc aaaaaattgg taaacgcggc  45240
cggggatttc aaacggccaa accgtgcctg gtcaacgctt cagggatttg aaacattgcg  45300
acgactgaat aaaggtcaat ttgatatttg gttacgccgt gacgaacctg aatatcgagt  45360
gcgggaagga tctaccttta tgaatcggct ctttaacatt gaggttgttt tagcctaatt  45420
attcccccc atcaatgagt aaaataccga ctctcattat ttgcagcaaa cctatatatt  45480
gcgctgaatc atagatcacc catcataact ggggataaaa ccacttaata tgttgtaacc  45540
ccacggtttc atatgagtat tctccgatta catatatgtt agttgccatg gataatccgt  45600
aatgttaaat agagttattt tctgtgtcac aatcataaat aacacaattg ttctttcaga  45660
actcaacatt ttaatatact gtagcaatgg tatcaatagt catacttatt aaaatgatat  45720
tttcctcaca gttaattaca cagcgtgaag taatgatatg gtgtttattt tgttattaaa  45780
tgtcgtatct tgtttaatgg ttttatttat gtgtttaact gatttcaatg taaaaaatat  45840
tttttacatt tagtaagtca tgtcaatgat atttgataaa gataattact gcttaattga  45900
tggatatttt ttgttttttt aatcaacggt ggcgtcgcta tcgtcttaac gttcacagaa  45960
gatatcattc tgcatagctc cgccagcatc caggcaagca tctactgtca gaaagtgctc  46020
aactttcata ccagcataaa aagcagcgca caatgcggtg gctatcacta gtcgtttttt  46080
cattgcatag tcctcgtagg ttagattatg ccccatgagc tgagaagagt gagctatcgt  46140
tgtcttgagc tttctgtccg gggtatcatc gaattttact ttatttacat agaatttata  46200
ttctatcata ccataattaa actttacttg aataaaaaca tcggtgtgct gaccatattc  46260
ctgatatgaa tataataata tagccttaat gctcatggta ataaagtgcc ctacagcaat  46320
ttcggcgggt ttgctgcaaa taatgagagt cgtgatttta ctcattgatg ggggggaat  46380
```

-continued

```
aattaggcta aaacaacctc aatgttaaag agccgattca taaaggtaga tccttcccgc  46440
actcgatatt taggttcgtc acggcgtaac caaatatcaa attgaccttt attcagtcgt  46500
cgcaatgttt aaaatccctg aagcgttgac caggcacggt ttggccgttt gaaatccccg  46560
gccgcgttta ccaatttttt gatgggggca tggtcagact caatacgatt attcaggtat  46620
ttgacttgcc gctgctttgc agcatcccgt atcttttcct tctttcagtt ttcatgacaa  46680
ctccattttt tgcaacaagc ccatagtggg gacaatgaac attaacgccg atcatgagaa  46740
aaacttaaaa gtgagcatta tatataaaat tcaactaatt ggaggaatca ccgaaatact  46800
taatggtggg gttattaact gggggatatt taacttggta ggatatttca aatcgtctat  46860
atcactaata aaaataataa ttattgataa cactaatttg gtcatgttat atgtaaaaat  46920
ttggataaat aatgaaaact tcttaattta tagtgaatta aaaacaaatg agttattata  46980
taaaccatat ctattaaatt taatagatat tattgtaact atgtagtgaa ataactttgt  47040
atggtaccgc gtatatgatt gtttacattt cagatgaata atatgggtga tgtcgagttg  47100
ggctgaaact tagtattttg cggttctttt ctctgctcaa tatcatcaat gaaacgttct  47160
aaccaagcct gcatttcatc gatatccaac cctaccagtg attgttgaga ccagagaata  47220
ggtttaccgt ccagtcttcc ttgaacatgg gcaggccaat gttcgccaaa caaattatcg  47280
ttggttggca aatcagcacc tagctcactg aacaactgta cccattgttg atgataacaa  47340
gcaatcagta cttggatgtg cccatccact tcaaatgtaa atgtataaac gtcattttca  47400
ttaacttgat ggttcaagcc aagcttcagg aaaagctgtt gcataagttc tgtgaaggtt  47460
gtctgcatta aacctccttg gagtcaaatg ttaacactct aaaacgctgc cccaccccca  47520
gaggataatg atacatagaa ttaccccaga atgagttagt aaaccatttg cggaactttt  47580
ccttatcaga aaagtggaat tcaccgaaat tgggatcgaa gaaagtaaca ccactctttt  47640
cgttgacata cgccgctatg gcgtgggctg acatttggcc tgagagatgt atttttttat  47700
aaccgtaacc tatcccatga gtatcaagga tagcgtttaa taattgatcc agcccttctg  47760
attccgtcgt accagtaaca tcaactggac gcagtaagca atgccgttca atcatacgtt  47820
ctgatatgcc atttttcttg aaccaatcta gtgttacctc atcttgatca acgtctgctt  47880
tacaaccatc tatttgcaac tgtttaattg agtaaagtgt atcgatctgg aatttcccct  47940
tacgcccgcc aacatagagc tggtcaaata agctttggcc ttgtgcatgg ctcctgatcc  48000
aatgtgcaca taaagcctca cagacaccgc tagcagtgtc tgaatgtttt attattttat  48060
gaagaaaagc ccctttggtc tgagcaaact tgaaattgat gttacctccg taatttgcaa  48120
cagactctct caccgcgggc acacgagtgc tgagtacaaa atgtatcatg cgatacataa  48180
tcatactgaa ggtaaagctg ctgcgttggt tagctttgcc gtcgctggtc aactttctat  48240
ccagcataga acggcctgac tggttatgtt ttatggtggc tgataacttt ttctgcaggt  48300
ttgagtgtga cagtgctgtt tccactttca ctcggtgtgc gccaatcacc ccttcggtga  48360
gggtagctga ttgaaggttt tcaccggcag aataattcga tagttgaata tggtagtgtc  48420
cgtgaatact gttcatctgt ataacctatt tatgttagcc attattttgc tataccgata  48480
aattgaatat atctggattt tgacgtctgg caatgaacga tagagcctac aataaattat  48540
aaccaatagg tgactcaggg attttctctg aatcagagta catgttgtac attcgattaa  48600
atattttttc aatagttaaa agttactttt tattataaaa attcaactta tggggacagt  48660
gatgttatgt tgatagcgtc ggggcgtcgc ggggagagtt tataataaac tctaatgtga  48720
taaaaatcca ttctaataat gatatattat actatatctg tagctttaaa ataaataatt  48780
```

-continued

```
atagagtgga ggatgcttga aatatttcga tgcatgggaa gctcattgag agtagatatt  48840
ctatttttat aaattacgga gtgattttaa ttatacactc gtagtgacgg ttattaaata  48900
gtgtagttta taaagtaaat ttgggagtag taactatgtt tattaaagat acttataaca  48960
tgcgtgcttt atgtaccgct cttgaacagt cggctcctga tacaataata aatacatcta  49020
aagaagaaaa taacagttac tactgcgcta ctgctcattt actgagaacg gatgtttgtt  49080
cattggtcaa tagagtaggg attgaaccac ttaaaagtgg atcaatatta tctactttag  49140
aagagttatg gcaggctgtt ggtatagtat atcgcttata cgaatggcaa catgtcagcg  49200
atattgacac caattttaag aaactaccca ataattctga ttttggtctt gtgttttctg  49260
tattagattg tgatatagag tatgtgttca tagggaaaaa agacagtgaa gggaatatag  49320
aattttatga tccgaaaaac tctctactta tagagaatga tgacataaaa aaatatttat  49380
atgatgaaga ttttcatcgt ttttgtatta tgctgatcat ctctaaatct gagttggagg  49440
aattgagtcg cgaatcctgc gatcaagaat gtattatggg atgaagctat attaaagagt  49500
ttgggatatg gtagttgatt atgttaaagg ttaattatct gtaacatata aaaaacagtg  49560
gtatgtaatc atcctgcata atcgtaccat tcatatttag agatcttccg gcatactgac  49620
cttgccaatg aaggagatcg ctaaacgggt acaccgtatc tattgcctcc tgaaactcaa  49680
tattcgccgc aaagggaaac aacgcctgcc agcctgtaac ccatcaccgc tggcggtacc  49740
ggaacgactt aacctgagcg ggtcggtcga ttttatgcac aatgcacaat gcacaatgca  49800
ctgagcggtg ggtgtcattt cagtacgtta taatgtcatg gatgattaca atcgtgaagc  49860
actggcgatt gtaatcgatc tgaacctgcc aacacagcgc cgtcatcaga gtactggatc  49920
gcattgtggt caaccgtggc tatgggaggt gccatgccct gttttaaatg gaagatgata  49980
tgaagaaaaa catgaagtta atagcaatga ctgccgtact gtcctcagta ttagtcctct  50040
ccggctgtgg tgcgatgagc acagcaatca aaaaaacgta atctggaagt gaaaacgcag  50100
atgagtgaaa cgatctggtt agagccgtct tcacagaaaa ccgtttatct acagataaaa  50160
aatatctcag ataaaaatat gcttggctta gccccccaaa tcacaaaagc tgtgcaggat  50220
aaggggtata ccgtaacatc ttccccagaa gatgcacatt actggatcca ggctaatgtc  50280
ctgaaagccg ataaaatgga tttgcgtgaa gctgaaggat ttctgagtca ggggtatcag  50340
ggtgctgcgc tgggggccgc attaggggct ggtattacag gctacaactc taactcagcg  50400
ggagccacgt taggaattgg attggcggct ggtcttgttg ggatggccgc gaatgcgatg  50460
gtcgaggaca tcaattatac tatggtgacg gatgtccaga tttccgagaa aacggacacc  50520
accctacaga ctgacaatgt ggcggcgctg aagcaaggca cctctggcta taaagttcag  50580
accagcacac agacgggcaa caaacatcaa taccagactc gcgtggtttc ttcggctaac  50640
aaggtcaacc tgaaatttga agaagcccgg ccggttctgg aagaccagct agcgaagtct  50700
atcgctaata tcctgtaagc cataagcatc ctggtatgaa gatgtactgg gatgtagtgg  50760
atcagtaata ctggacacct caatagcctg ttaatttaat gacagccaat tgaggtaatt  50820
gataatgact caacctaaac agaccaaacg ccgtttttct cctgaattca aactggaagc  50880
tattgagcag gtcgttaagt atcagcggtc aaccatcgag gttgcacgcg ctctggagct  50940
ggatcccagc caattgcgta aatggatacg ccagtacaaa gaagaagtca gcgggatgac  51000
gccggacaat cctgcactga caccagagca acgtgaaatc cagtcgctca gggcgcagat  51060
taaacggctg gaaatggaaa aagaaatact aaagcaggca gctgtgttga tgagcgagtt  51120
```

-continued

```
ccccatcaaa tctttgcgtt aacacggctg aaaacaaaat ggccagtggt cgaattgtgc  51180
cgcctgctca aaataacgcg cagtgtttac tctgcttcgc tgaattttcg ggttgatgta  51240
aaacgtctgc aactgcgtga attgcatcaa cagagccggg gagcagccgg cagcagaaca  51300
ctgagtctgc tgatgcgtca gtcgggttat aacgtggtgc gctggctggc ccgcaggctg  51360
atgcgggaat gtggtctggc gagtcgccaa cccggaaaac ctcgttaccg tggcgaacgg  51420
gaggtgtcac tggcatcgcc agatttactg aaaaggcagt ttaagccgtc ggagcccaat  51480
cgtgtgtgga gtggatatat cagctatatc aaagtcaatg gtggctggtg ctacctggca  51540
ctggtgattg acctttactc ccgtcggata gtgggcagtg ccatatcgtc atccccggat  51600
gctgagctgg tgtgtcgagc ctagcgtaat gcactggaga cgcgcccaag ggaaaagagg  51660
ctgctgtttc attcggatca gggagggcag tacaggagta agaaatccag gcagttactg  51720
tggaggaccg gagtgatgca gagtatgagc cgcaggggta actgcctgga taactcacca  51780
atggaaagag tgttccgaag cctgaaaagt gaatggctgc ttgtaggggg ctatatggat  51840
gtccatcatg cggtacgaga tatcggtgaa tggatacaaa gttattacaa cacccccca  51900
tcggcacaat ggtggattac cgccctgtga atacgaagag cggtggaaaa aggctacgaa  51960
ggtgtcctga ttttgtgatc cactacacta cattcaggag agttggacca gaaatcaggt  52020
aataaggtcc ggtccactcg ccttcaaatt caacatgtaa ttcattgtca aacagtcccc  52080
agagcagtaa aacagagatc cggttcaacc tcatacgccg tgccctcggc catgatgcgg  52140
gcaatcgata cccactttgc ggcgttcagg ctcttgggca aagcgacaga actgctccca  52200
gttgcacgta tcgcggatcc cctcgggggga acatttgtca gccagtcttc ctggctagaa  52260
tgtgtttaga ttatccgtgg tgattcagtg gttgcacggt atcaagcaaa aaccaaggac  52320
actcttagtt tgaaaaggca ggtaatatac agcttcagtt aacccatttt actgactgat  52380
atttatcgtt ttttgtagca agacgagtgt tttcgattat gtacgtatag gataaatttt  52440
tagtacctat atattggcat gccctgctgt taccgacgag caaaaagaaa ggtcatctac  52500
agcagattag gtaactgtca aacttggggt atttcccata gtcgtcatat agacggaaat  52560
gtgaacgtgc ccagttcggc attgaggctc ttacgcttca tcgcgatgct tggtcactgg  52620
ctgcggcgaa cgttgatatt ctatttatat atctttgcgt tatttgggtt gttttgcgta  52680
ttttttgatg ttttactata aagacgcaaa tttcatagag ataatacata tggacctaaa  52740
gtcaactctt gaccgctgta ttgaacgtgg acagttcatg actcaagaaa ttgctaaatc  52800
acaattcggt aatgacagtc cggctgctcg aacgattact agacgctggc gtattactga  52860
agctgctgaa cttgtcggag taacaccaca aacgatccgt aactatgaag actcaggcaa  52920
actgccaccg cctgatacag caatgattgg tcgtgttgag caacgaactg gatattccat  52980
ccagcaaatt aatgatatgc gtgatgtgtt taaaacaaga ctatccaaac caaaaggcga  53040
aaatcctgtt gttcttgcca ttgcagctca taaaggtggt gcatacaaga catcgacatc  53100
tgttcatatt gctcaatgga tggcgttaca agggttacgg gttttgttga ttgatgcgac  53160
tgatcctcaa gctacggcct ctttatatca tggctatgtt cccgatctgc atatacatga  53220
agaagatact ttgttgcctt attatcttgg tcaacgagat gatgctgctt atgcgataaa  53280
accgacttgc tggccaaatc ttgaagtcat tccttcttgt ctggcagtgc atcgtattga  53340
gtcggaaatt tatggcttgc atgatcaggg gaaattacct gtagcccctc atcttttatt  53400
acgtgctgct attgagtcag tctgggatag ttatgatgtt gtggtgttag atagtgcacc  53460
aaacttaggt attgggacta ttaatgtcgt gtgcgctgct gatgtcatcg tagtgcctac  53520
```

-continued

```
tccggcggag ctttatgact atgtttccac gttgcaattt ttcaccatgc ttagggattt  53580
gatgtcaaat attgatctca acggttttga acctgatgtg cgcgttttaa ttactaaatt  53640
tagtaatgcg atcggtagtc agtctcagtg gatggacgat cagataagga atgcatgggg  53700
tggaatggtg ttgaaagaag ttgttcgcgt gactgacgaa gtggggaaag gccaagtacg  53760
aatgcgtact gtatttgaac aggcagctaa ccagcgttca acgccagctg cttggcgtaa  53820
cgctgtttcg atttgggagc ctgtttgtgc agaaatattc aatcggctgg ttaagcctcg  53880
ttgggagaat gcatgatgaa aaggtcacca gtgttacgta atgcgccttc aattaatttt  53940
gatgatgcta aacccgcaat cagcaatgca gagccctcgg tttctgctcc ggcggtgagt  54000
cagcttgctt ctcgagttag tggcatgaaa ggcaacacaa tcgtattacc tgtttgtgga  54060
aggaacgttg cttttacgct taaagtgata gcagcacctg atgttgaatc taaaacaatc  54120
gtttttagtg gtaatgagcg aaaccaagca ttattaagtg agacgtcgtt agatgacttg  54180
atcccttcat ttttaacgtc agggcagcag atccccgcct ttgcacgtga acataacggg  54240
aacatcgagg ttgctgatgg aagtcgccga cgtaaagccg cgatactcac cggaagtgac  54300
tataaggttc tggttggtaa cttgaatgat gagcagatgc tatggctgtc ccaaattgct  54360
aatgagtatc gtccgacgag tgcttatgaa cgaggcctgc gttacgccca acggctaata  54420
tctgaatttg aaggtaatat tagtaaattg gcagaggccg agcatctctc tcgcaaaatt  54480
attcagcgtt gtattaaaac ggctgggctg ccccttaaaa ctattcaact gtttgctaac  54540
cctaatgaat taagtgctcg tagtggcgaa gcattaagta aagcttatga aaataatgtt  54600
gatacgctaa agcgagttac gcataaaatt atgaagcaaa aacaggaagg tcgccagttt  54660
actacggaag aattaatcgt attgctgatg cctgagagaa aacagccaga gaacattcat  54720
aaaaaaagct ttggcaaaaa tatagaagca aaatattcaa aagacaatgt ttctttctat  54780
ctcaaatctg tgccagagtc cttggttaaa caaatagaag aactcttgaa tacctatgca  54840
aaggaacatt ctttgtagtg cctgaataag atcagaacaa ggtgggttgt ctgcccgcct  54900
ttatttagtg tatatctatt gttttagctc atccttcgta gaagatctcc ttctttacaa  54960
ctcatttcct aagctgaact gtggccccaa tcaccaacgt tagcattgga tatccaggtg  55020
ggaccgtggt cccaattact aacgttggca ttggatatcc aggtgggacc gtggtcccaa  55080
ttaccaacgt tggcattgga tatccaggtg ggaccgtggt cccaattacc aacgttgaca  55140
ttggatatcc aggtgggacc gtggtcccaa ttaccaacgt tggcattgga tatccaagtg  55200
ggaccgtggt cccaattact aacactggca ttgaacatcc tagtggaaat gtgattcgaa  55260
ttgaaagcga ttaagtcgat gagcattttt ttagtgatag ctttagggag attaaactag  55320
cggatatttc attatggaga taataatttt cgcttcattt atcacccctt cgcaatactc  55380
tgttcaccaa gtcatactat tcttagccca gagctattga tgcatcaaca acttgcatca  55440
gatgtttact gttcgcgtgc ggcggtgttt catcaaacat atctatctga cctggtcgac  55500
tgccgacgtc attaagcatg atgtcggctt tttgatagcg atatccatcc cgccaggttg  55560
gatacggcga tttcatgtta gtatcgatgt aacaatgacg gctctattgc attaaggcac  55620
agtctggtaa catgctgttt tttttatgat attgcctgca catatcttta atcaaaaaat  55680
ttttttgtcg cctgcattac cccatcgatg ttatagctca gtgtgttcac tggtatcttg  55740
gcgatgccct gagttttcta aatctagagg aaatgatgac gaaacacggt atctctgttg  55800
agcattacac actccacagt tgggttattc gtgtggtgcc attactgcat aaagcttttt  55860
```

-continued

```
gccgttataa atgtaccgtg ggtcgccggt ggcgaatgga tgaagcctca aaggtcagtg  55920
gaaatacctg taccgggcgg ttgatactcg cggttagact atcgattttc tgctgacggt  55980
aaagcaggat gcggcggcag cactgtgccg actggtatca ggtctcccgg taaattcata  56040
tattaaagta ggcagggctg gctcattaca gattgtttag ctataattgt attactcagt  56100
aatacataac ggaggggata tggctcacgt aaccagcgta acacttggag agcatttgac  56160
aggttttgtg ggggaaatga ttcagtctgg tcgttatggc aatatatcag aagtgcttcg  56220
tgatgcctta aggctaatgg aagcacgtga acagcgtgtt caacatgtac gcgatatggt  56280
gcttgcagga acaaatgtac ctgtgagcca tcgtttaatg gatgagattt tttctgctgc  56340
ggtgaaagat actagtgtat aaactgtctg aactagctga tgaggatatt tataatattg  56400
ccagttatac tatccggcat ttcggtgtga ctcaggctaa gttataccat gagaacttgg  56460
caaaggtatt cgagctatta gctaaaaatc cagagttagg ggctgagtgt aactggattt  56520
gctctgatat tcgccgtttt cagtataaaa agcacggtat atactatata acgcttagca  56580
atgatatttt gatttctcga gtgctgcatc aatccataga tatagatgtt caggattttc  56640
cagagcatga gtagtaatac agaagagaga taagtcagaa attctaacaa tgagcatgct  56700
aaaaaacgat tcgcccctga aagatcaggg acgaagatat tcgcaatatt gatagaaaaa  56760
gggggaaaca ctatcccctt gtttttatcc atatcacatc aatgacagta atttctgcat  56820
ctgttgcgcc agccctttga tctcatttgc tgcctgcgtt agatcaacgc cactggcgac  56880
gtacgcgctg gccgccccac caatagttcc ccactgcgag aagggaatac cacaaacagg  56940
cgtgtttaag atggcactgg cctcagcttg caattcccca ccacaaaact gcatcagccc  57000
ttggcattga gtgatactgc cacgaagagg gccgctgccc gtagcgaact gatcatgatt  57060
tttctgcagc atctctgcat ccaagctatt caactgctgc atgtattttg gcagcgtctc  57120
agcagcaagt tgcttgatac tgtcactgaa agacgtagga cttggcattt gtgcaggtgt  57180
gggtgctggt gtcaccaccg gtttatggct cccctccgag aacatgcgtt ggataaaccc  57240
aatcacagag tgggccactg atgataacct ctcaatgata cggctggcta agctggaacc  57300
ctgagggctt tcagtgcgcc cggccagatt gtttgcatat tgatcacttg tttgctgtga  57360
gactgagcgc ccagacattt ctcctacgct gctagatcct gacacagatg tcggcagggg  57420
cagtgatgta gaaataaatg atgatatttt catgactatt tattaccttg gctattaaaa  57480
caaggttatc ttagtgggaa aatagccgat ggctatataa aaaatcgctg ctgtttttgt  57540
tgttatatta gacaaaacaa aaactaaaaa ttataggcta aaattgatgg tctgccgaga  57600
gtgctttggt taagttgata ttttatctaa ctattatgag atcataatgt attcatttga  57660
acaagctatc actcaattat ttcaacaact ttcgttgtct attccagata ctattgaacc  57720
ggttatcggt gtcaaagttg gggaattcgc ctgccatata acagagcatc ctgtcgggca  57780
aatattaatg tttaccctac cttctcttga caataatgat gaaaaggaaa ccttacttag  57840
ccataatata ttcagtcaag atatattaaa acccatctta tcctgggacg aggttggggg  57900
gcacccagtg ttatggaatc gacaaccatt gaacagcctg gataataact cactatatac  57960
tcagcttgag atgctggtgc agggggctga acggctacaa acctcatcac taatctcacc  58020
accacggtca tttagttgag tagatttttg gttgttgcct tattatacgg aatgacctgc  58080
ccccaggatt agatacaacg ctcacttagt aatgtcggat ccttcactat cagaattacc  58140
ctttctccag gccgccgcaa attcagacgg cgtctgataa ttcagcgtag agtgcgggcg  58200
gcactcatta taatcctgac gccattcact gatggttttc ctggcatgac tgacgtcact  58260
```

-continued

```
gaaccagtgc tcattcaggc attcatcgcg aaagcgtccg ttaaaactct caataaatcc  58320
gttctgtgtc ggcttgccgg gctggataag tcgcagttcc acgccatgct caaaggccca  58380
ttgatcgagc gcgcggcagg taaattccgg gccctgatca gttcttatcg tcgccggata  58440
gccgcgaaac agcgcaatgc tgtccagaat acgcgtgacc tgcacgcctg aaatcccaaa  58500
ggcaacagtg accgtcaggc attccttcgt gtagtcgtcc acgcaggtaa ggcactttat  58560
cctgcgaccg gtggccaatg cgtccatgac gaaatccatc gaccaggtca gattgggcgc  58620
cgccggacgg agcagcggca gacgttctgt tgccagccct ttccgacgcc ttctgcgttt  58680
tacgcccagg ccactgaggt gataaagccg gtacacgcgc ttatgattaa catgaagccc  58740
ttcacggtgt tagcgccagt gatataagac ggtaattcac cattagtatt gtccgctcca  58800
cccaacatgt tgtttccttg aggttctcac accagaaagg acatcaacat gctgagcaga  58860
gaggactttt acatgataaa gcaaatgcgc cagcaggggg cgtacattat cgatattgcg  58920
actcaggtgg gttgctctga acgaactgtc agacgctacc tcaaataccc tgaaccgcca  58980
gccagaaaga ctcgccacaa aatggttaag ctgaaaccgt ttatggacta catcgacatg  59040
cgcctggcag agaatgtctg gaatagcgag gtcatcctcg cggaaattaa ggcgatgggc  59100
tataccggcg ggcgttccat gctgcgttac tacatccagc ccaaacgtaa aatgcggcca  59160
tcaaaaagaa cggttcgcgt cgaaacccag ccgggatatc agctccagca cgactggggc  59220
gaagtcgagc tagaggttgc tgggcaacgg tgtaaagtta acttcgcggt taatacgctg  59280
gggttctccc gacgcttcca tgtcttcgct gcgccaaagc aggatgctga acacacctat  59340
gagtcgctgg tccgtgcctt ccgttacttc ggcggcagtg tgaaaaccgt gctggttgat  59400
aaccagaaag ccgcggtgct gaaaaataac aacggaaaag tggtgttcaa ctccgggttc  59460
ctcttgttgg ccgaacatta tgacttcctg ccacgggcct gccgcccgcg cagggccaga  59520
accaaaggta aggtggagcg gatggtgaaa tatcttaagg ataacgtctt cgtccggtac  59580
cgcaggttcg acagcttcac ccatgttaac caacagctgg agcagtggat ggcggatgtt  59640
gctgataaac gcgagcttcg ccagttcaga caaacaccgg aacagcgctt cgcgctggaa  59700
caggagcatc tgcagccgtt gccggatacg gacttcgata ccagctactt cgacatccgc  59760
catgtgtcct gggacagcta tatcgaggtt ggcggcaatc gttacagtgt tcccgaggct  59820
ctgtgcgggc aaccagtctc gatacgtata tcgctggatg acgagctgcg gagctacagt  59880
aatgagcagc aggtggcctc acatcgactc tgttcagcat cgtctggctg gcagactgtg  59940
ccggagcacc acgccccgct ctggcaacag gtcagcatgg tagaacatcg cccactgagt  60000
gcttatgagg agttgctgtg atgcatgaac ttgaagcgct gctgagtcgc ctgaaaatgg  60060
agcacctgag ctatcacgtt gaaagtctgc tggagcaggc ggctaaaaaa gagctgaact  60120
accgggagtt cctgtgcatg gcgctgcaac aggagtggaa cggcagacat cagcgcggca  60180
tggagtcccg actgaagcag gcgcgtctgc cgtgggtcaa aacgctggag cagttcgact  60240
tcaccttcca gccgggcatc gatcgtaagg ttgtccggga gctggccggt ctggcgtttg  60300
tggagcgctg cgagaatgtg atcctgctgg gtcctccagg tgtcgggaaa acccatctgg  60360
ccgttgctct cggcgtgaaa gcagcggatg cagggcatcg ggtactgttc atgccacttt  60420
atgaagacat tactaacatc ggggtgtact aatcaacgag gagcaggtca ggaaatagcg  60480
ataacctata aatttgtggt gccagtaata tcagatttcg ctcagtaaaa gttaacacca  60540
agttggagtg ttgactttta tctcctgttt ttttttaatt tttaatgtaa aagacttgta  60600
```

-continued

```
ttaagtccat tcacttggtg gcgtcgccgc ctcctcattg gtaatgagga gtaccggaag  60660
agttctcaat gtgaatggtt gagctgtata agtttgttat actttatatc cacggtgata  60720
caacgttggg gtagcatctg ggaaggagag aaataaaaaa attctatatt tttctaattt  60780
taaagggtca gttatatgcg cacttacagt tcattacttg aagaatttgc tacagagcta  60840
ggtcttgaag aaatagaaac aaatgagtta gggcatgggg ctgttaccat tgataaaata  60900
tgggtagtac atctggcacc tatcaatgag aaggagttag tggcttttat gcgggcaggg  60960
atcttgactg gtcagtctca actttatgat attttgcgga aaaacctctt tagcccacta  61020
tctggtgtaa ttcgttgtgc gcttgataaa gatgatcact ggctattgtg gagtcagtta  61080
aacattaatg acaccagtgg gacgcaactg gcgagcgtat tgacgtcgct ggttgataaa  61140
gctgttactc tttcttgtga acccacaatg aagaaagagg aggatgatca tcgtccttca  61200
tcatctcatt tactggttta attctataaa agaaaaacgt acgatatcca ttaatgggtt  61260
tggttgagac tgtaaacaag attgtataat tgcctgtttt tgatatcttt actccaacaa  61320
cggagacagg caaatttgat ccctccccaa tatccgtacc aggctaaatc agagatccgg  61380
acctttttga tgacttcggg caaattctgc cggagtcagg ttatttaacg aagaatgcgg  61440
atgaaaatga ttatattctt gccgccattg ttcaattttc tcctgagcat cttccagaga  61500
aaggaacccg tgcacgttca gacattcatc cctcagactg ccattaaatg actcgataaa  61560
ggcattatct gtaggctttc cggggcgtga acagtccatc gtgaccctgt tttcatacgc  61620
ccatcggtcc atcgacttcg agatgaattc gctgccgtta tctgtctgca gcctttgtgg  61680
aatacgcccc agcgaatgtt ttaatctgtc catgacagcc acaacatcat ctccacgtaa  61740
cccctgaccg acctcgatcg ccagacattc acgactaaaa ttatccacta tagttagcgc  61800
cctgacccga cgcccgttga acagattatc agcaacgaaa tccatgctcc agcactgctc  61860
taacgcggtc acttctggac gtgcgtgcct gtgcttcgct gtcacatgcc gccgtggacg  61920
tttcgaacgt agattgagac cctcaagaca gtaaatacgg tgcgttttct tatggttaac  61980
aagccagcct tctctccgca gcaggatatg aatgcgcgga cagccataac ggatgcgcgt  62040
ctccgcaatt tcccgtattc gctgagtaat agcccgatcg tcacgatggc tacgatagtt  62100
gtatacagtg cggctctgca tcatcagcct gcaccctctg cgtactccga tacggtacgc  62160
cgccagcaga tattccacgg catcacgctt ctgcagcggc ctcagaactt ttttcggatg  62220
acatcctgca gcatttcctt atccagactc agatcggcca ccagacgttt gaggcgctga  62280
ttctcatcct caagctgccg aagacggcgc aattccgtga cacccattcc cccaaacttc  62340
ttcttccagt tgtaaaatgt cgcttccgaa atgcccatct tcctacagac ttcttccact  62400
cgagtacccg tttcagcctg tttgagtgca aaagcgattt gttcttcggt ataacgcgtc  62460
tttttcataa cgaatgaccc ctttttggac ggaaaagaag ggccgaaaac tctactttac  62520
agcggtactg aactaagggg gaagatcaag caatccttgt ttgtcgatta ttttaaattt  62580
gttttgactc ctccaatctt tgattcaata gacacgcatt caatggtttt tattatatca  62640
tcaatgccgg cccagagatt ttcattatta ttgttcttgt aatttgtttt taattgagta  62700
ttcaaactcc tctcaattcg catcacttca tcaatatgtt caagcttaca ctttattaag  62760
tcatccctaa gagaaatatt ttccttctca agtttagata ttcttttctc tagccgagtt  62820
gttatttctt tttcctttct atttttctct ttgttgaaaa ataaatcaaa gtagtatttt  62880
gcaaaaaatg ttaacattac actgagtgtg taaaccagaa attgaatatt tgatggtcat  62940
gtggatttag gaatataaaa cccaaccgaa gccataaaaa tagcgggaat tgcatatgat  63000
```

-continued aaaaatgtat aaatagtcat ttttatttat ctgctttagt ttacatagtt gtgttctatc 63060
cctttgtctt taaagctatt acttagcttt ttaggggcaa ttctaagaag tcccatagat 63120
gtttctagtt cattggaaaa atttggaata ccctttgagg catcaaacac catgctatat 63180
gtaaactgaa ccgtaagttc ttttctttca acgtctagcg aatttaaact tgccttaatt 63240
ccgagacata ctgagttaaa ggaatttgtt gctttatata ctgaaacttc atttggcttt 63300
ccattgctga aaaagtcaaa gttctcgaaa gtaaaaagat atttaatttc ataaatgttt 63360
aaactgtcag ttgtgaggtc tgaaaaataa taatcacctt caatataggt aaactcacca 63420
ttatttttat caagcatttt tatattctta agagattcca ctttttctaa aatagagtat 63480
aaattattct gcaaattcat tttacgcccc ttagctgttt attgtgattc attgatgact 63540
ttataaatag ttgaacgagc tatattcatt tttttggcta tttctgtcgc gcccatcccc 63600
tgttcatgca attcgagtag ttcctttctg ttgattctgc gctttcgtcc gaatttaacc 63660
ccctttagct tagcctcttc tctcccttca tttgtacgct ccagtattct ctgtcgttcg 63720
gcttgagcca ctgctgatag aatagtgaca accattttac ccatttcccc atcggtactg 63780
attccgtcat caataaactg gatggacaca ccctgggcgt caaactcttt tatcaactgg 63840
atcatgtcga cggtgtcgcg gccaagacgg tcgagcttct tcactagaat gacgtcacct 63900
tcttccacct tcatacgcag cagatccagc ccctccctgt cggcagagct gccggatgcc 63960
ttatcagtaa atatacgatt tgctttcacg cccgcgtctt tgagtgtttt gatctgaata 64020
tcgagggatt gctgactggt tgatacccgc gcgtaaccaa aaagtcgcat aaaaatgtat 64080
cctaaatcaa atatcggaca actggtgtct attataacaa aaaatcgatt aaatagacac 64140
acaaaccgca ccatttcagt gtgtccgaca acttataata tttcggacgg ttaaaaagtt 64200
gttaacaaat aaccgtcagg cagggaggcc tgtatgccag tcgattttct gaccactgag 64260
caagaacaga attacggttg ttacgttgca gaacccaatg acgtgcaact ggtgcgctat 64320
tttcatcttg acgagcggga tcttgctttc atttaccagc ggcggggaaa gcataaccgc 64380
ctgggaatag cacttcagct cacaacggcc cgttttctgg gaacctttat tacggattta 64440
acccaagttc tgccaggtgt tcagcatttt gtcgccgtac agcttaatat acgccgtccg 64500
gaagtcctct cccgctatgc cgagcgtgat accactcgca gggaacatac cgcgcagata 64560
aaggaatatt acggctatca tgaatttggt gattttccgt ggtctttccg cctgaaacgt 64620
ctgctgtaca cccgtgcatg gctcagcaat gaacgccccg gtctgatgtt tgattttgcc 64680
actgcgtggc tgcttcagaa taagattctg ttgcccggag caaccacact tgtacgtctc 64740
gtcagtgaaa tacgcgaaag ggcaaatcag cggctctgga aaaagctggc cgccattcat 64800
tatctgaccg aactaaacgg cacgaaaaaa cgcctcctgg atgatgctcc tgaacatatt 64860
attaccggcc cctggaaacg cctggtgtac gatgcggagg gccggataca acgtgccggt 64920
tactcgcttt gtctgctgga gcgccttcag gatgcattga gacgccggga catctggctg 64980
aaaaatagcg atcgctgggg agatctccgc gagaagttgt tgcagggggga agagtggcag 65040
gctcagcggg tcctcgtctg ccgggcgttg ggacatccca ccgatggaca taaaggcgta 65100
caacagttgg cggtccaact ggatgaaacc tggagagcag ttgcatcccg ctttgaagga 65160
aatacggaag tccatatctg caatgacggt aaatatcctt ccctgactat cagcagtctg 65220
gagaaattgg aggagccact gtcgttgctt cgtctaaaca atcgggtcag gcaactgcta 65280
ccgccggtag atttgacgga actgttgctt gaaatagatg ccagaacggg atttacacgt 65340

-continued

```
gagtttacac atgtcagtga atccggggct cgagcgcaag atctgcacat cagcctgtgc  65400
gcggtactga tggctgaagc ctgcaatatc gggctggaac cgctgataaa gcacaatata  65460
ccggcactga cgcgccaccg gctcagttgg atgaaacaga attaccttca ggcagaaacg  65520
ctggtcagcg ccaatgcccg gttagttgat tttcagtcca cgctggagct tgctcgccgc  65580
tggggtggcg gcgaagtggc ttcagttgac ggtatgcgct ttgtcacgcc agtgaaaacg  65640
gtcaattccg ggccgaacag aaaatatttt ggctccgggc gtggcatcac ctggtacaac  65700
ttcgtctctg atcagtactc tggattccac ggcatcgttg tccccggcac attacgggat  65760
tccatttttg tgctggaagg ccttctggaa cagcagacag ggctgaatcc ggttgagatc  65820
atgacagaca cagccggtac cagcgacatt atatttggcc tgttctggct acttgggtat  65880
cagttttccc cccgtctggc tgatgccggt gaagctgtat tctggcgagt ggataaatcg  65940
gcaaattacg gagcacttga tgagcttgct cgtgggtgtg cagatctgtc gaaggcagaa  66000
aatcagtggg atgagatgat gcgaactgcg ggttcgctca agctgggcac cattcatgct  66060
tcagaactca ttcgctcact actgaaaagc tcacggccgt cagggctggc tcaggccatc  66120
atggcggtgg ggcgtgtaaa caagacgctg tatcttctta attatattga tgatgaagat  66180
tatcgtcgcc ggatcctgac gcaactcaat cggggagaga gccgccatgc cgtggcacgt  66240
gcaatttgtt acgggcagcg cggtgagatc agaaaacgct accgtgaggg gcaggaagat  66300
caactgggcg cattggggct ggtcactaac gcagtggtac tgtggaacac gctttatatg  66360
caggaagcac tgagctggat gcgcagtaat ggagaagaaa ccagggatga ggatatcgcc  66420
cggttatctc cactgatgca cgggcatatc aatatgctgg ggcattatac gttcacgcta  66480
tcggatgata ttttaaacgg agaactgaga gcattaaatt tcaatttaaa caatgaatta  66540
tctccttaac gtacgttttc gtcccattgg acctcaaaac ccatcaccgg gtagccacgg  66600
ttgaccacaa tgcgatccag tactctgatg acgtgctgtg ttggcaggtt cagatcgatt  66660
tcaatcgcca gcttttcacg attgtaatca tccacacaga tcagtgcatc gtgcataaaa  66720
tcgaccgccc cgctcaggtt aagtcgttcc ggcaccgcca gcggtgatgg ggtacgagct  66780
ggcaggcgtt gtttcccttt gcggcgaata ttgagtttca ggagacaata gatacggtgt  66840
acccgtttat ggttccagac atatccccat cgcctcagga tttgaaaaac cttaaagaaa  66900
ccgtcgcgtg gataacgctc gaccactgat ctggtgttca gtgaatcagt ttttttcgca  66960
tggtgaactc ctcaaaatac atattcagta tgtcggaaat tctctaaaag agaatggtta  67020
tttttgatgg tcattacagt acagattatt ttatataatt tattacccac ttttttttata  67080
ttttttgata gagggaggat aataaataaa aaaattataa agtaatggtt tcttgctgtt  67140
ttctggtgtt tttctctata tttatgtttt tttggtgaaa ataagtgtgt tgtcaggtaa  67200
tttcaaagga ttatacaaaa tatccggttt gaggtgaggg atttttttttt atattatctg  67260
cataacactt ttcgtgttat ctgaaagtat tttgtagtgg gctgactccg acgattcgat  67320
tagagattac aaacgatgca tatattcagt agttaatcga tatcttttta agatcgatta  67380
gtgctgtttt ttgcatgatt atcagaaaat aagtcataga taatcctatc cctcttctat  67440
gggaggcgtt cgctttaatt aatatatttc tcagatgtta taactgagct tttattcacg  67500
ggaaattaaa gaaatataaa aggtgcttac aatgactaaa gattttaaga tcagtgtctc  67560
tgcggcatta atatctgcgt tgttctcatc tccatatgca tttgccgagg agcccgagga  67620
tggcagcgat ggtattcctc gtttgtcagc agttcaaata agcccaaatg ttgatcctaa  67680
attgggtgtg ggattatatc cagcaaaacc aatattacgt caagaaaacc caaaattacc  67740
```

-continued

```
tccacgaggt ccacaaggtc cagaaaaaaa agagctagat tagcagaagc aatacaacca  67800
caagtactag gcgcaggcgg gctcaatgct cgcgctaagg atccctatag cattgcgatt  67860
ggtgctactg ctgaagcagc aaaaccagca gcaattgctg tgggctctgg ttcaatggca  67920
acaggcgttg attctgttgc aattggtcct ttaagtaagg cattgggaga ttcggcagtt  67980
acttatgggg taagtagtac cgcccagaaa gatggagtag ctatcggtgc gaaagcatca  68040
gcttcggata ctggtgtcgc tgtcggtttt aactcgaaag ttgatgcaca aaactctgtt  68100
gccattggac actctagtca cgttgcggca gatcatggtt attcaattgc aattggggat  68160
cattctaaaa ctgaccgaga gaatagtgta tccattggtc atgaaagcct taatcgccaa  68220
ttaacacatc ttgcggctgg cactgaagac actgatgcag tgaatgtcgc gcaattaaag  68280
aaagaaatgg ctgaaacatt ggaaaatgca cgtaaagaga ctttggctca gtctaacgat  68340
gttttggatg cggccaaaaa acactcaaat agtgttgcca gaacaacttt agaaactgct  68400
gaagaacatg caaataaaaa atcagctgaa acgttagtaa gcgctaaagt gtatgcagac  68460
agcaattctt ctcaaacact aaaaactgca aatagctata ccgatgtgac tgtaagtaat  68520
tcgactaaga aagcaacccg tgaatctaat caatacacag atcataaatt cagtcaactt  68580
gacaaccgtt tagataaact tgacaaacga gttgacaaag gtttagccag ttcagccgct  68640
ttaaacagct tgttccagcc atatggtgta gggaaagtaa actttactgc aggtgtcggg  68700
ggatatcgtt ctagtcaggc attagcaatt ggttctggct atcgtgtaaa tgagagtgtc  68760
gcatttaaag ccggtgtggc ttatgccggt tcctcgaatg tcatgtacaa cgcatcattt  68820
aatatcgagt ggtaatatca tttagaaatt aacaagtcta taggaaaaca ccgattacat  68880
aatcgtaatt ggtgttttat taatatgcta atgaaaaatt ttttagtaat tctgcttttt  68940
atcatggttt cagttacatg gggaactaca tggttagcga tgaaattaac cgtcgaaaca  69000
atctctccga tatttgctac gggcatccga tttatgttgg ctgcgcctgt attaatccta  69060
attacatcaa cccgcaaatt cagcgaagca gagtaaacac tgcgcgttat tttgagcagg  69120
cggcacaatt cgaccactgg ccattttgtt ttcagccgtg ttaacgcaaa gatttgatgg  69180
ggaactcgct catcaacacg gctgcctgct ttagtatttc tttttccatt tccagccgtt  69240
taatctgcgc cctgagcgac tggatttcac gttgctctgg tgtcagtgca ggattgtccg  69300
gcgtcacccc gctgacttct tctttgtact ggcgtatcca tttacgcaat tggctgggat  69360
ccagctccag agcgcgtgca acctcgatgg ttgaccgctg atacttaacg acctgctcaa  69420
tagcttccag tttgaattca ggagaaaaac ggcgttatcc agaacgtgaa gcgatttacg  69480
cggcgctgga gtaaaccaat gggcggcatg gccgcccatt ggtttactta tcagtacgca  69540
gtgccatttt gcggccgcgc gaaaaccctt gtcactctaa gtaacgcgga gggtgagtcg  69600
gtactgattt ctccgcagca gaataccgcg caggatattt ccctgttcat gccccgggaa  69660
ctgacggtca gtcaaggtga tcgggtgcga tttacccgct cagacacaga ccggggttat  69720
gtggccaata gtctgtggga agtggcgggt tttactgaag acggtgctgt gcgttttcgt  69780
cagggcgacc aggaaaagat tgtcgatcca caaaaggcca ccgaagaccg ccatattgac  69840
ctggcctaca cgctgacagc ctatggtgtg caaggggcca gtgagcggtt tgtcatcgcc  69900
ctgtttgggg ctgaaggtgg cagaaagagg atggccactc tgcatctctt tacgtgacat  69960
tgtcacgcgc caaagagcat gtctaggtct atacggacaa cgttgttaaa tggttgggtc  70020
ttgccgggca gtcaaatgcc ggaaaaaccg cgcattgtag tggatcagta ataccggaca  70080
```

-continued

```
ccctcaatag cctgttaatt taatgacagc caattgaggt aattgataat gactcaacct  70140

aaacagacca aacgccgttt ttctcctgaa ttcaaactgg aagctattga gcaggtcgtt  70200

aagtatcagc ggtcaaccat cgaggttgca cgcgctctgg agctggatcc cagccaattg  70260

cgtaaatgga tacgccagta caaagaagaa gtcagcgggg tgacgccgga caatcctgca  70320

ctgacaccag agcaacgtga aatccagtcg ctcagggcgc agattaaacg gctggaaatg  70380

gaaaaagaaa tactaaagca ggcagccgtg ttgatgagcg agttccccat caaatctttg  70440

cgttaacacg gctgaaaaca aaatggccag tggtcgaatt gtgccgcctg ctcaaaataa  70500

cgcgcagtgt ttactctgct tcgctgaatt ttcgggttga tgtaaaacgt ctgcaactg   70559
```

<210> SEQ ID NO 2
<211> LENGTH: 100990
<212> TYPE: DNA
<213> ORGANISM: Yersinia pestis

<400> SEQUENCE: 2

```
aaacagcccg gcgtgctgga gcgactggaa cgtgaggacg gtgtcattat ccaccagcgt     60

cgcgagtggc gcatgtacga tccggaaaca ggtaagctca cgacgaaggc cggaacgctc    120

tggggtctgc tgaagaaaat ccactgataa caccaaccac tgcggtgagt agccagctca    180

ccgcgcgcgt atctgggtca taaccactgt agtgagtaaa acggctgccg tggcatccgg    240

tatccactgt agtgagtaaa gtggtgatta tcgacttcac tatccactgt agagagtaaa    300

caggcgttca ttcacagcaa acaaccacta tggagagtga tggaatgcga cctccagcgg    360

gtatccacta tggagagtaa accttcactg ttttcagcgg atgtctactc tccacagtgg    420

atagtaaatc cagccaaccg attctgctct ccatagtgga tagccaatag cgaagggagc    480

aacgataacc actatagaga gtggatttaa caagtcaccc agtgaccact aacctcgcag    540

cccttgtttc atctaggttt gtaaccacta acattcattt cgttatttga gcgctactgc    600

ctacagtggt tactattcgg ttgttgttac tcactacagt ggatagcgga cttcagataa    660

acaaaaggcc cactacagcg gaatagtgag cctttctact ctctacagtg attgggctat    720

ttgcgagcct ttgccttgcg cagctcttcg agaatcgcca gttcttcctt gctcaacatg    780

accatctcac cgtctttttc ttcaggaaca acatcgatga tgtcctcctg accatcgcca    840

ggcaagttat cttcctgctc ttctggttct tccggcgcag ctttagttgg tggcaatgcc    900

gggcgtaact tcggccgcct atagtggatg atgaagtaga ccgagctgcc gcgcttcact    960

tcggtgtaat cgagatagcc gatctcccgc agctgctcca tcgccttcct gactgtcgcg   1020

ttctgggtaa tggtgcggct ggttaagtta agtctggcgc gtaagcgagc caacgagatt   1080

ggtgccgggt caggtggcaa actttcgatg aatgtgtaga gtgcctgggc ggattctttt   1140

ctggagagtt cgttgattgc ccggagttgc agaagaacct ttttgtcgaa ctggtagagt   1200

tcgaaaatct taggatcagc ctgcagcgag accgtgtcgt tcttagtgct gtactttgct   1260

gtctgcacaa ggtgagttac gtaatactca tcagagcctt tactgcggaa tgagatagtg   1320

tttgtggcga tacgagttag agaactgtcc aggcgcttac gtaacttcgc ggacgatctg   1380

gccgttggta tgccacagag cctgacgaac tcgacgaacg gtaacgtgac agtgtcgcca   1440

acaaccttgt gcttggcgaa cgcgtggatg atgcctaccc acgttttaaa gtcgttatcc   1500

atatccagac gaacgccgga gatccttatg tcctcatacc cttcggcttt ggccagagac   1560

agctgtttga gttcagcaga ggcgtccata gagaccattt gccccttcct gcccctggac   1620

gtcgatttca gcgtcggaac gaagagacca agacgcatca gagcaacggg ctgaacagtg   1680
```

-continued

```
ttgttggtgt taggaactaa cgtaacaact tcgcctgtct ttttgtctgt ttctgagaat   1740
gcttcaacga tcgctatgtt tttattgccg ttttcgctca ttccaagtgt ctctttttat   1800
tcgacggctt tggtggcctt tgctgattac agtggatatt agcactcatc acagcggtta   1860
tcctaccgcc tatagtggtt tttctactct ctacagtggt tggtttactc ttcatagtgg   1920
ctgatcttct ctctatagtg gatatcgatc acctctgagg ccagatggca caacggtttg   1980
cgggatgcgg ggatcttttt gggtctttgt gggtctcttt ggttctattt gggatctgaa   2040
ttactggatc gggcctgtgt ataaaaatca ggtaattgca aaaccagcca tcactccctt   2100
tctggggata atgtgtggtg gaaacaaaca cgcctgaacg caagattaac gatatatcca   2160
tgaatatcag ctatctaaca cagaaaaaca ggcaaagagt tatccagtca agacaatgcc   2220
tcctactcac tacagtggat accgaccact ctccagagag gttgttttgc tcttcatagc   2280
ggttattatg ctctctacag aggttacttt gctccccata gtggatagta accccctctc   2340
aggccagtaa ccgcaacggc tggagacgat cggggatctc ttttgatctt ctgtaggatc   2400
tctctgggga tctaattatt ggatcggtcc tgtgaataat gggtataagt aaaacaggca   2460
tttgcaaaca tcggtgcgcc ttgtcagtta tcgttgcccc ggacaaaact atttgaataa   2520
gaattatgga tctcaaacgc acgcgctggg ttcgccgtct tgaagatggc tcctacacca   2580
ttgaatcgaa cactatcctg aacaaacaga aattgctctg cgacctatgc ggcatagcgt   2640
cgaagtgccc gattaacgaa actcggctca aactctacga cgccggtgcg cacttccact   2700
tgaacagctg catacgttac gtgccactgc tggcatttcg taaaccgatc atcggattgg   2760
acgcacccta cttcaacacg ctccgctctg gtgtaacatg gcgagaccgg gtcgaacctg   2820
gcaagctcgt ttgtctggtt gaggctgata ctggaaatat catccggttc gggagagtcg   2880
ataaagtcta ctccggcccc gtggatgaga tgctgcggaa acacagccgg tttaaccatc   2940
tctgcatggg cggagagaaa attgataagg ttggcgaagt gatccgcaaa tcctacggac   3000
acttcctgaa cgacgacagc cttctcacgg ccatctacat tcgccatgtc gatcgggagt   3060
tcgatacgga gtatcacagt gctgaagagt tgaatcttgt cgaccctcgc ccaaaagctg   3120
gggtaatcga catcagcgta gcgcgtcaga agccctctga gacgttttaa acgtaaactc   3180
atggttttac cggggcataa aatatggtgt cttagaaaga cactgagagc tttagggatt   3240
aatacatgag tgaattttat tcaagggcgg cggctgtggc agaccaagct ggcaatgaag   3300
acgaacgagc agggccggtt tttaatttgc agcccccgtt aatcatagtg acagtaaaat   3360
atctgtcaca aaaacagtac gagagagatt aggatctcag tagtggtcag aagaaaaata   3420
tgtactaggt taaaacaggt acatgtttac tggtacgcat cacataaata atagtaatgc   3480
actccaggta aataggcgat tgtccagtag acaaccgcct gtaatgagac tatttgcctg   3540
tttcttgctt gtttaagccc actgctttct gataatagct ggtatcataa tatttatgcg   3600
tatctgtcag atttttctct ggcttagcaa gcctgcttcg caacagtaga acatttttta   3660
ccccttctgc attaatagca gcatcccgtt gcagcccatt gttaagtaat tcctgtaatg   3720
caggtcctgc cagctccgcc gtcattcctg gtgccttttt gaccagaatt tcttctgctt   3780
ctttttggtt acgggggtca taaatccagt tcagtccgtc gatatagcta cggatgtaac   3840
ttaccagaat atcaccattc tgagccgccc aggagcgggt tgtaatgcca gttgtgccct   3900
gatagtcgcc aagttcactt ccggaggcaa ggatcttaaa cccattttct ttcgcctgca   3960
gatttaatgg agtacggaga agtgttgcat ctgtcttacc ggcgagaagt gcattaaagc   4020
```

-continued

```
gatcattcgt actgccaaca cttgtatagt ggacatcatt ttgtgtcagc ccgtttttct   4080

caagataatt ccggataaca aaggcatagc cagtggtcaa agcgtcgact gaaacttgtt   4140

ttcctttaag atcactgatg ttcttaattt gagggttagc aactaatgaa agaagcccgt   4200

tatccactcc ataaaacgcg aacatatccg gattcactac cggctctttc acctggccct   4260

cttgatacgc gatgacgtta tcaatacctg ctactgcaat attatacttg ccattcagca   4320

ggtttctgac cagttgaccg gaattgggtg tgtaatccat tttcacatta agaccatttt   4380

ttctgaaaaa gccttttttcc tgggcaaccc aaacaggcag gttccacccc ccctgaaaag   4440

taatgacgtt aatatccctg atagatgagc ttgattcccg ggtatccgcc gcgtgtaggg   4500

cgccgggcag gataaatgca agtgaaacgg ttaaagccaa gcatctgaac ataatattta   4560

cctcttactg tgaacagttc gtaagagttt aaaaaaatgg gtaatgataa taaagtagaa   4620

agcattctgg ctatctggcg aataactggc tcatttttac cagcaaatgg ataagcataa   4680

gcgccggtaa ggcagcctcg aatgcgcaga tctcggtcca ttgccagtga cgaaagccca   4740

gactgctgag agcggattct agagacatgc ctataaattc tgacgtgacg aagagttgct   4800

cgttacattt agaaatcatt accgccatga aaataggtat tcacttactt atgtattttg   4860

tcataatcat gtgcctgtag attttcttct gtgccgtgtt gtctgggttg ttcgcctctc   4920

aagcacgctt aatatctgta tcaaaataac cacaaaggaa aagacacatg acattgccat   4980

acggggtgat atcagatccc cattatcatc gttgggatgc ttttgcgaca acaaacgctg   5040

acgggctgaa ctctcgactg gagatccaac tggatgccac gaaagaagct gccaaagcca   5100

tgaaagctgc gggctgcaag cacatgctgg tggctggtga tactttccat gttcgtggtg   5160

ctatatcgcc ttccgtcctg catttcgtga ccgaaactta cgagtggatc atcaaagagt   5220

tgggcctcga agtggttatg ctggccggca accacgacct cgaaaccaac gattccgtat   5280

acagcgccaa tgcagcggcc tctctgcgct caatcggtgt ggaaatcgtc tgcggcaaac   5340

gtcctcactc catcaaaatt ggcgacgtta ccgtccatct gattagctgg cgcaataacc   5400

acgcagagct tatcagcgac ctcaaaacac tgcgttccgg gctggatggc gacaatcacg   5460

atgtcgttgt gcatacctcg atcaacaaag cgatccctac catgcctgat gtcggcatcg   5520

acgcacagga actgaaagat atcggcttcc gtttgttgtt gtccggacac taccacaacc   5580

acaaagaagt gctgcctggg gtggttagca tcggggcgct gacgcaccag aattggggtg   5640

atgttggctc gctggctggc ttcatgatcg tcaaccctga cggcacattc acccaccacg   5700

aaacctctgc acccaagttc gtgaaccttg aggacgatgt ggaagacgat caaattcgcg   5760

gtaactacgt gcgctttcgt gccgttgttg agaacgatga agaaggcatc aaactccaga   5820

acgtcctgaa aacaatgggc gcgaagggtg tcgtctgcaa cttcatccgc aaggcatcga   5880

tgatggaagg ctctgccagt actgcggaga ccagcaaaat agacagcctg ggcgagtccg   5940

tcgcggcgta ctgcaagatc gttcacgaca ctgatggcgg cttcgacctg agcaagctgg   6000

acatgctgtg tcaggaaatc ctgaccgaag cggagagtgc ggaggcagtg tgagtacgaa   6060

ccattctggg agctttcggg acttcgtctc cacaatgaga agacttgaac gaggccagac   6120

ggtgatgttc cacaagccct acccacctaa tggaaaccct gtggcgtttt acctgggaag   6180

attgagcaaa aagggcgtac taaaacgcaa atccttcccg gctcacacgg agtttcaact   6240

acgaaaaggc cagcatttga atcaaaaagt ttgaggcatt gtatgaaatt tctaaagctc   6300

caggttgaga acttcatggc gttagccagc gccgaagttg agttagacca acgcggtctg   6360

gtgctcattc agggtgttaa cagtggcgac tcttccgctg ccagcaatgg cgcgggcaaa   6420
```

-continued

```
tcgactttga tgaacagcct gatgtggtgt ctgtatggcg aaactgcgca tggcgtcaaa   6480
ggtgacgacg tgctgtctac aggtcacgaa aaaaactgtc gtgtgatggt aactgttgag   6540
gatgaaggaa agcgttacgc catcattcgc caccgcaaac acaaagagtt caagaaccgg   6600
ctgatcgtcc gtggcgaaga cggtgacatg accaaaggca aagacacact gacgcaggag   6660
ttcgttgaac gcctgattgg tgcatcgaaa gaggtgttca tggcgtccat ctacgccagt   6720
caggaagcaa tgccagatct gccgggtatg tccgacaaga acctcaaaac catcgttgaa   6780
gaagccgctg gcgtcgaccg gttaacgcga gcctatgcca ttgctcgcga gcgtgctaat   6840
gcagctgccg cacgcatgga tgttaccaaa tccaaaatgg acgcctgtct cacgcttatc   6900
gagaccgcgc agtcagagat tgaggcggcc aaagcgtcct ctgatagttg ggaacgcgat   6960
cgcggcgaac gtctggacaa ggcccgcgta gatttggctg gcgcggaggt aacgctgtct   7020
gaagtcgtga tggaaattcg ctcgctgccg gaacagatcc gggatacgga aaacgcgatt   7080
gctggcgaac gctgcaagct ggcctccaaa gaagagcatg acgccaaact gctgaaggtg   7140
cgcggtgcga ttacggagat ccgctcaagc atccgcactt cagaagcggc acagaacgag   7200
tcgatgaacc gtgctcgctc gtttaaaacc aaagcagaag aggtcagcac aaaggtcgga   7260
gcaccttgtg ttacttgcgg aaagccctac tgcgaagaag atttgtccac cgtgaaggag   7320
agtttcattg aacaagcgcg taatgagatc ggccaggcgc aagcatcagc ttcggcagtg   7380
gctcaacaca aagctcgtct tgagaaagcg ctcggcatcg aatctgcact ggtcgcagcc   7440
acacccgacg tttcagaaat catcgccaaa atcgaacgcc tgaccaatga gctaagtgcg   7500
ctgcgtcatc gcgaacgtga agttgtggcc gtcgaagcga tggtggcgcg ggcgcgtacc   7560
gatgtgaatc gcattatggc agaggtaaac ccatttctgg ccgttattaa gcgtcatgag   7620
gacaacctgg ctgccaataa atctaatcat gcagtactta aaaatgagtt aaagagtatt   7680
caagaacagg ctctgttgct ggagaaggct cgccaggttt actcccctgc aggtgttcgt   7740
tcacacatcc tgacctccgt tacgcctttc ctgaacatca ggactgcgga gtatctcaac   7800
acgctatcgg acggcaatat cgttgccgaa tggtcgacaa tggagacaac gaagaaaggc   7860
gagtatcgcg acaaattcaa tataagcgtg accaaaacag gttccagcaa atccttccag   7920
acgttgtctg gtggtgagaa gcgtaaggta cgtattgcgt gctctctagc cttgcaggat   7980
ctggttgcca gtcgcgccag taagaatatc gagctgttta tcggcgatga aattgacgac   8040
gcgctcgaca ctgccggtct ggagcgtctc atggggattc tggaagccaa agcgcgtgaa   8100
cgcggcacag tgatgatcat ctcccacaaa gagatgaaat cgtggttccg ggaaaccatc   8160
actgtcgaag tcaaagaggg tcgcagctat gtcgtttaac ttgagccgca cgcagttttt   8220
gcagatgttt gccgtgatgc aatctataaa gctgataaac caccatacgg caaaagcagc   8280
tgcgcctgca cttttgtgga aaaacgaaaa catcaatgac gaccagttct cggtattaac   8340
cagtctgttg tcatcgactc cgttgatgcc gagcttggct atgttgccgt caggaagcac   8400
tgcgccgatc cttgttaacc catttacgga aggtggatat ctcccacatt ctgggccggg   8460
gttcgttgcg atacctgaaa ccggaacgct gaatatccaa gaaaatgcgc tcttcaatgc   8520
aatggagacg cacatcagca ccgcattcac caatctgatt cgacacgcta acgcacgcgc   8580
tgatcacgtt gcaatgcctg gtgctgcttt cgccagcgtc tctgttgact atgatcggca   8640
cgcgccaatc tcaaagcggg cgaaactctg cttttacgag gagggatgtg aagtagcggt   8700
tattaaagtt cttctccccc atgtattcag cgcgaatgaa aaggttgcac accatctgat   8760
```

-continued

```
cgacatcatg cgacatttca tcggccagag catgattgat gcagacattg ctgcaggtgt   8820
tctaaccaac gatagcattc atgttgttag cgacattccg aagccgccaa ctcgcgagcc   8880
ggagaagaca cttgaacaga aactaatgga atgcccaacc tgggctacgt ggtaaggaga   8940
ccaaaaaatg agtaaaacca ttcgtgtggt tggcgtcgac ccttcaatga gcaactttgg   9000
cctggcgatt ggcacgctgg atctggaaac ggataagctg gacattcatg gcctgacatt   9060
ggtggaaacc aaagctggtg gcaacaagaa gacggttcgc gtaaacagcg acgatctacg   9120
ccgcgctaac gaaatctggc gcaccgccaa gcccataatc gagcaggctc atatggtgtt   9180
ttgcgagttg ccggttggta gccagtccag tcgcgcacaa acctcatacg gcatctgcat   9240
tggcgtactg gcgtgcgtgg ataagccact gatacaggtc acgccaaacg agattaagca   9300
ctatgtcggg aataagctga ccacgtcgaa ggaagagatc attcagtggg ctacgcagaa   9360
gcagccaaac gccccgtggt tgcgccgcaa gcaatctggt aaggaagtgc tggtgaataa   9420
aaacgagcac cttgcggacg ctgtcgcgtc gatttacacc ggaatgcaaa ctgatcaatt   9480
ccgtcaggtt cgcgatgtgc ttgcagggat tttataagtc gataattgat aggtaggtgc   9540
ttatctatta acataaggcc actatattta gtggcctttt ttgtgcccag aaaacccccca   9600
gctaggctgg gggttcagta aagctttcag ctttgggtca gttataaaaa cccctttttga   9660
tttgttaaaa cagtttgcgg tctggcaact gcaaatgttc aacaagaaat caaaaggggg   9720
tcccaatgag ggatgaaaag agcttagcgc acacccgatg gaactgtaaa tatcatatag   9780
tttttgcgcc gaagtaccga aggcaggtgt tctacaggga aaaacgcaga gcgattggca   9840
gtattttaag aaaactgtgc gaatggaaaa acgtgaatat cctggaagca gaatactgtg   9900
tggatcacat ccatatgctt ctggagatcc cgcccaagat gagtgtctcg ggatttatgg   9960
ggtacctgaa gggaaagagc agtctgatgc tttatgagca gtttggcgat ttgaagttca  10020
aataccgtaa cagggagttt tggtgtcgag ggtattacgt tgatacggta gggaaaaaca  10080
cggccaggat acaagaatac ataaagcacc aattggaaga ggataaaatg ggtgagcaac  10140
tctcgatccc gtatcccggt agcccgttta cgggccgtaa gtaatccata gatgcaaatg  10200
tcagatcgcg atgcgcctgt tagggcgcgg ctggtaacag agccttatag gcgcatatga  10260
aaaacctccg gctatgccgg aggatattta ttatacccga taacaaaatg ttttttgcct  10320
tatccacatt gcgataatta caccaacaag aaaacaagat gtttacgcat ggaggatatg  10380
cacatgaccg atttcactat ctcccctaaa gctgaaaacg tatggctgga atcctggctc  10440
gacctgtcat cggaagagaa gcgagaaatg gatcatattg aacaggacga acagtgtgat  10500
gcccgcttct tccactttga gggcagcgtt tatgacattg ccgacttcat gcgcgatgac  10560
cgattcccgg gctggcacgc aggctaccca ttaaatgcct tcgccatgct gatgatccgc  10620
gtggatggct caggcgatac catcgacgtc ggtttgctcc actaagagaa cgaggccacc  10680
catgctggtg gccttaaatg gccatcctgt ttcccgcagg ctaaaaacac ccacctctta  10740
ccgccaggct accgaacaac cctccgactc cctgcaggcc accatctgcc ggaacagaac  10800
gcttggacgc cttatgcgcg tagcgataat taaaccaaca agaaaacaaa ttgtttaaag  10860
gattatcacc atgaatttta tcgctactgt taacacccct tcgcatggcc atatttctgt  10920
gacgttctct gataacgata aaagcgtgct gggcgcctgg cgtgacaatg taaccatcga  10980
gctgtccggt aaagagaaac agcagatcac caatgacatt atctgcaacc gtcgccataa  11040
gcgcgtattt gaaaaagcgt atgtctccac ctcgggattt ggtgtattca tcttcccggt  11100
acgcagcggt cgcttctgcc ggtcaaaact catcgagttc gccacgcaga tcgcgctatg  11160
```

-continued

```
ggttaaaaca gaatccggat tcgactttac cgaacaggaa gcagtggggg aggggatgcg  11220
catcgccaac aacgccatca agtgcaaaaa cgtcatctat gaagcaggaa tcgactcgtg  11280
gagtatctcg tgcggggact acgtgaaaga ggtgtacgga aagaaccgca ttcacatcct  11340
ggctggcaag taagagggga ggggctggaa acgccccttt cttttcgtcc accagttgcc  11400
gcagggaaac ttcagaaacg gccagagagc tgtccgggga accgaaggga aacggccagg  11460
gaattttcgg gaaacggcgg ggtttgcctt tatgtagaaa acagagcggg agaagccaaa  11520
aatcgctcca gaaattgcgt agcggcgctg gggtagttgc cggtggagtt tcagctcctg  11580
agccacccag atagctttcg ccatgtgatt atgtgaatcc gtgggaaagc cactgcaagc  11640
gcgtacacgt cgcgtcaacg tgccaatgat acgcgagcgc ccacggatca tgccaatatt  11700
gccgacacgt cccgaaggat agcgcggatc acgtcgccag atatcgccag acgatcacgc  11760
ccacgacacg acaaaataag ccacgcgcta aaacgcgcta taacgtgttt tttattgtgg  11820
gtaatgagta tgtaccacca cacataaaaa cgcgttaaat tggcgcgttt atggcgctta  11880
tttttggtct gttttggctg acttcagaca ataaaaaacg cgccaacaat ggcgcgttat  11940
ggtgtgcgga tcttgaaacg aaaaaagcgc ccatagtggg cgctattgtt tttatttttc  12000
taagtgaatt ttaaagccag cgtttaaaaa ttcttgaatc attaaaagaa catcggattc  12060
tttgattcct gcgcgcttcc tatgctccgc gctattcaga tctattttaa acgtggtttc  12120
gtcgactact tcagagctga gagcgtatcc agctaaacca gcgatatcat aaacaagagt  12180
atgattatgg atgttaacgc cagcgataaa aataaccata aaaacgctcc ttaaaaaata  12240
aaattgaata cagacttaag atctttttgaa taagcgccca tagtgggcgc tatattcaat  12300
taattacgct ttgaaagcgt cagccagata gttataaaaa tcatttttga taaagcgata  12360
ttgctgcgat ccgtttttag cagcgcccat tcctttgatc ttctcgacca gtccgagacg  12420
ttcacaaaga ttgattagtt ggttggcttg agtgtagcca gcgtccaatt taatttcgtt  12480
ggcttttttc gcttcattca tcaaatcgaa aacagcgcca ttagtgaatg tttccaattc  12540
atcattaatc atttcgatta atgcgaatac gcgagatccg gacatatcag cgacggaata  12600
aacgcattta ccagacttga tagatttaac cagataaacc agtttttcga gtgaatagct  12660
attggtcata gcttcacgga aaaacgcttc aggtgcttgt ttgcttgctt taatcgcgta  12720
gtaaaagaca ccagctaatt tctcatcatt aacagcgttt aaaacgttgt tggtaaagta  12780
tgcaagtttg gtagtcgctg caagcatgtt agctttatct gctttggtgt gcgtaccatt  12840
ctgataatga ttgttataag tctgagtcgc attgttggct gcaacttgca attcattagc  12900
gataactaca gcagcgtcga tgatagattt tttagagata gcaacgttag acatgatatt  12960
aatccttatg taatattgat aacttaattt gttatttatt tatcgttagc gtgttcgctt  13020
tcgatgtgac taattatcga tatacaaaaa ttaaaatcaa gagttttttg cgcgggaatg  13080
aaaaaaaatt ttcttcaata aaaatcaaag tcttagaaat aaaacgcgtt ttctcgaagg  13140
tgttgcctaa ataaattccc tattcggtca atcaccctta tatatttaaa acggaaccgg  13200
gattagggga ggtaaatata acgggaagtg acacataaaa taataaccgg acttagccgg  13260
ttattaccct tatagattta aaacggtaaa atccgttcga cccaatcgaa catgacgact  13320
gtcttccgac cgtcccccat gttgagcgtg gcctggcaag cgtctacgcc tgaagacccc  13380
ccctcaattt cacggccatc cgccatgtag acccttatag acttctgcat ctcatgagcc  13440
tggcgacaaa ttttaaagaa atcacggcga gatggccgat tgtccacata gtctgggtgt  13500
```

-continued

```
accgttgtcc gacccgtgaa atcgtgcgca atgccttctg tcacacctga ttcaatcgtg  13560
ctgattcgct caagtgggag ccttatacga ttttctttgt cgaacggggc agggcaaagg  13620
tcgactttgt tgcgcgacga catgagaccc tgaacgtaca tgcagaacac ctgaccatct  13680
tccatcgtga cccttacagg aatgagagac ttacgccaga acatcagcgc tttctccacg  13740
ttggagtaat cgcgcggcca gacttctgca ggaatcccgt aggtgatgtc agttttattc  13800
gtcatatcgt cacagtgtcg ttggtaggat atcgatgtca cctgcgttgc tggtgaatac  13860
ccggaagact ttcgtctcgc cagctttggt gatggtctcg cgttcctgac gagcagggtt  13920
cagtgcgcac agcccggcgc cctcaagtga ggcgccaaca atccactgcc cggcatcaag  13980
atggaacgtc gctttttcgc cggtctccag tttcgcaact gtctctccat taatgaagat  14040
ggatgcgtcg cagcccgcac ctatcatacc tttgtccctc ataaccacca gcgtggttgg  14100
ggcagacgtc tggtatttga aaactcttgc ctgcggagcc ggttttgcat tggctacaga  14160
cactgggcgg gatgaacatg cactcaggag taaaacgggg atggtaatca gtggaagtag  14220
aacgtgtttc atggcttgaa ctaaatcctt atcacttcaa cgaacaaggc gtcttgcgac  14280
gcccttaatg cttaatcgag acgtttgaga atatcggcca gatcttcttt ggtcatgcca  14340
gaggattcgt aaatcttcat gaccttttca cgagcctttg cagaagcctc taatgacgta  14400
gccgccttat caaaatcggc catcgtcatg ttggacagta ccagattgat gacgtctgct  14460
tttgacagct ttatgttgcg ctcacgcagt cgattctgaa aggtttccag cttgtcgtta  14520
gctttttcgg ttaactgaac ctggcagtgt atagcgcgtt tctcgctcat gcttactctc  14580
tattcaaaac agtaaaatcg aatgtgctac ccaccggcaa gactccttcg gcaaaccctg  14640
gcgtcgtgtc gataatgtgc ttccgctcat atgaatgcga catgaggtat ttattgctca  14700
cgtcgatgaa gtcggtaata aagcacacgt tagcctgatt ctttttggct cgaagaccgc  14760
gaccaactcg ttggcgcatc tcaacttcgg ctttgccacc gccacccaga atcaccgcac  14820
ctacgcttgg aacgtcgacg ccaacatcca gaatggttga accaatcaaa acatctatcc  14880
tgcctgccgc cagactgctg agctttgctt gtcgggtagt ctggtttgat tctccgtaga  14940
tgaaatcgac cttcaggccg ctttccttca tcatttccat cagaatctga ccatgacgct  15000
tcaaacgaac cagcgtcata cagtttagac cgtgactttt gtacattaac gcttcgcgca  15060
caatggcctc gttgcggccc agattgtaaa cgatgcctaa ctgataggct ttctggtaag  15120
ccgtactcat cccaacccga aagttaaggt gtttcgaagc aagttcggcc ctgattcgca  15180
cctcgtctgg agtgtacgcg attttatgat atagaaagta gggttttgct aaaatacctc  15240
ggtcgatcaa atatttttcc gtcaccttta tctcaatgcg acctgcaacg gccatgagac  15300
gcatatttgc ttcggttgag tccttcatga acggcgtagc agtcagcgcc agacggtagt  15360
cggcattaat gcacaaccgg gcgatatcgt agaagtttga accagatgat tcgtgtgcct  15420
cttccagaat cagcagagaa acgctggaca ggaagcgctt aaccagttcc cggcgcttca  15480
ggtggtaccg tttttctct ggtgaggcat cgcgcggcgg ctcttcgaga aaactggcca  15540
gggtctgcac cgtggcaacg ttgatatggc gcgagacctg gaactcacca gatccaatca  15600
ccccaacttt ctgacctttc agccacggct cgccattctc cgcgcggtag tcgattgatt  15660
tctggaagtt ctctgccatc tggaacatca gaaccgagcg cgtggttaaa aacagcgtca  15720
tacgaccaat gcgagcagct gccttacacg ctacgttcga tttaccgcca cccgtcgcaa  15780
tctgggcaat catcatccct tcgcgcacca gtgtttccac agtctgatcc tgatacgcat  15840
agtccgggtt atacgggaat gggttaacta ccgggttcgg cttgcccagc gcgggggctt  15900
```

-continued

```
tttccttgcg cacatgcacg catttgatgc cagctttcag aaggttggcc gctactggct  15960
tcgcaaaccc agccgggaac gcgtttttgc tccagttgaa catcgtgctg gtccctttcc  16020
agtcaccagc ctccacttca tagctcaaca tctcctgaac gagccgcttc acgttgtcat  16080
cagcgccaga aatcagcgca ttgactgcat tcgatacaat ccgaactgtc ataaacctct  16140
ttccttcgtg ccttttgtat ggtaattggc tattatagta agtaagtact tatataatgg  16200
attgtatcag aattatggat gtgaaaatta cgattctgca ggtggaagtc gcgaacctgc  16260
gtccgaatcc ctggaatacc aactccgttg gggcgcaaaa cttcgaaaaa ctgaaaggct  16320
ctatcgaaaa attgggcttt tttaagccaa ttctggcgcg ggagctggac gggggcattt  16380
ttgagatcct cggtggcgaa caccgctggc gtgccgcgat ggagcagggc atttcaacgg  16440
ttcccgtcat ctccgtgggc aaaattaacg acctggtggc caaacagatg tccctcgtcg  16500
ataacgagcg ctacggcgaa gacgatcagg ttgctttgca gcgcttaatc gaagaaatcc  16560
agtctgaaat cgactaccgg ttgtccgata tcgccccgta tgacgacgaa atggcggcaa  16620
cactcgccaa agcgtccgtt atcgatcttg aagcgctgga agcgctctcc cgtggagatg  16680
acgagccgat cgaagaggac aaacgcgaga aaaccgagcg agtcggtgct gaacaccaga  16740
cgatgcgctt caaggtgaca tttgatgcat cagatcgcgt cgccgacacc atcaaaacca  16800
tcatcaaaga gcagggaatc aataccggta acgaaatgga gaacgccggg gaagccctgg  16860
tgtggctggt cgactactac aaggagcgta tgtaatgacc aaaaactttg aaatcgtcta  16920
tcgaaacccg gcagaactca tcccgtatga gatgaacgcc aaaaaacatg acgaacagca  16980
gatccgcgac ctggctgccg ccatcaaaaa gcgcggtttt gaccagccga tcacggtcga  17040
caagcacgac gtcatcatta ctggccacgg tcgtcgcgag gcggcacttc tggctggtct  17100
ggagcgtgtg ccggtcatcg ttcgcgacga cctgagcgaa gaagaagtga aggcaaaacg  17160
cctggaagac aaccgcctgg ccagtattga ctacgacgcc atcaaattgc agcaggaact  17220
tgaatccctg gtgctgggcg acgttgaggt cttcggtttt gaagagcgcg agctgaacgt  17280
gcttgtcggc agcatgaccg aagagatgga aaccggcgct ctggtgctcg atctgggcga  17340
agagacggaa cgccagaaag aagagcacac cgagatcagt cgcgaagtgg ccgctgaaga  17400
agtccgcgtc atcgacgtat tgggctttaa aacgctccct gctggctctg ccattgtggt  17460
tggggatttg cttgcccaca tggaggaaat cacgggagag tgcggggtag acgctttcgt  17520
ggcgtatgcg gagaaagttt cttctgggga gctggctgca tgagcaaata caccatcaac  17580
gtatcgtttc agacccgcgt gaataaaacc atgcgcacgc tggagattgc cgaatcgttc  17640
ggtcttggcc tggacgaaaa agagtggacg ctttacgaca atctggagct ggaagtgaag  17700
cagggcgatg tggtgtacat caccggtcag tccggttccg gcaaatccgt tgtgctgcgc  17760
gagctgcaac gccagatgaa ggatgaaggg ctttctgtag cctccatcga tgactttacc  17820
ttcaacaatg aggttaacgt catcgaccag ttgggcaaaa ccaccagcga tgcgctgggg  17880
ctgctgtcta tggccggatt gaatgacgct tatctctttg tgcgcaaacc atccgaaatg  17940
tccgacggcc agaaataccg cctcaagatc gccaagctga ttgagtccgg cgccaaagtc  18000
tgggccgccg acgaatttgg tgctgttctc gaccgtgtaa cagctcaggt tgtggcgtcg  18060
aacctccagc gtgccgcccg caaggttggt gcgacggtaa tggtggcgac gacccacgaa  18120
gacctgaaga acgcgctgcg cccggatatg cagatcacca agcactacaa agaacgcgtg  18180
aaggtggaat atgcctgatt tgaagatcgt tgagctgaag ccatcgaaag aggctgacaa  18240
```

-continued

```
caacaacgtt gaagtcatcc gcctgctgga agaagcactc cagcacgcca gagaaggtaa  18300
aagccagagt ctggcgttgc tgatgatcaa caacgacggc agtgttctgg attgctggca  18360
taacggtggg cgtccatacg tcatggttgg ggcgatggaa tcgcttcgcc tggacttcat  18420
caatgccaat atcgagcgca ggtgatcgac atgacagaca tcatcatcaa acgctaccgc  18480
ccggaagagt tcccgcgtca tctggacttt ctggagcgta tgaccgttac caaaggcacg  18540
gttgaagact ggcacgcgct gaagtcgctg cactataaga cggatggtaa gccgttcgcg  18600
ccaacgtatt atcgctgcga actggacgac cggctggtgg gcgtcgtggt tatggcttac  18660
ccgaaactgc tgctggcgcc tcgccatcgc atgtttccta agctgaagcc aaccaccaat  18720
accaccgtgg ccaaccagta ttgggggcgg tacgtgaaca acaactttgc ggtgattagc  18780
cgttccgttg tggacactca gtaccgcggc gtcggcgtct cctatcgaat gattaacctg  18840
gttagcagga tgcacgaccg gccaatcatc gagatccagt cgtcgatgag caaatacaac  18900
ccgtttgcca tgaaagcagg gttccagttc atccgtccgg agcgtccgaa gagctatgag  18960
agtgcgttgc gcgtcttcca gcgtcatttc cgttccgacc ctggcgacaa cgaagcgatc  19020
gtcaaagagc tgttcgccat gagtgagtct cgccgtcgtc gtgcgctgcg tgatctggtc  19080
gctgactacc acaagaacag ttccctggcc aaagccgggc gtaatcgtgg cacgacgatt  19140
caggacattg ccgacagcct ggtggacgag gccagcattg tgaagctgct caaggatatt  19200
cacaacctga gcttcacgtc tccgctgtat ggcgtgtacc gaaacccgga ctttggccgt  19260
cagttgcctg acacgctgcc actgctggca ttcgacaaac agcctttgaa caaacctctt  19320
gaaattgcat taccggcata aggatttgcc atgacgttga ccgacaaaca aaaagacatc  19380
atcaaaacca tcaatttagg ccatgagcgt gggcatctgc tcgatctgga cgagctgctt  19440
gaagtgctgc cgtacaaaac gaccaaacag agtatgcagt tctctatccg cgcactggtg  19500
aaaaaggggc tggtggagaa aggaatgtgc cgccagcgcg gtgattctgg ctaccaccgt  19560
cgcacgctgg ggctgaccac gttaggtcgt gccagagcca aattactggt gatgtaagtc  19620
ggtctgggag ccagtttgag agcctgcttc cgtatatata aatactaagt gacttattaa  19680
atatatacgg aagcaggttc tgaatactcc ccagcccggt tttaaacacc cagaaaacaa  19740
attggttagg catagaatta aacaagttgt ttaggagcgc aaggatgcgc tctgagtgtt  19800
ttagagggat ctatgactgt agaaaaagac gagagcaaaa ctcgcctgac gccagctgag  19860
tgggcagaag ccgaagcgaa gtggacttcc ggtgaataca cactctccaa gctggaggaa  19920
gagtacggca ttcgtcgtga aacgctctcc agacatttca aaaagcgtgg attagagaaa  19980
ggcgcggact ccgtggggaa gatggtgcgc gagtcgctca aatccgacgc agagctgcgt  20040
gcgaaggcgc gtgcagagaa aatcgaagag cgccggactc gttacgacga ttgggcgttc  20100
gcactcggtc ggatggtgat gcatgaggtg gccacagcca agaaggacgg caagccactc  20160
gcaaccatcg aagatgacct gaagagtctc cagcgtgcca gcggcacact cgctaagtgc  20220
ttcgaagtat cgtcgaaagc gctcggtatg gatcgcgccg aaaacgagga cgacgaaatc  20280
ccgaatctgg tatttggcga acttacgcct tcccaggtgg cgcagctgcg taaggaagat  20340
gatgagccgg atctgattga tgacgatctg cttgagtcac tcgaagagga agcactgagc  20400
gaagctgagg gcgattctga cgcgtctggt gatgaaagtg atgggagcgt ctaactatgg  20460
ccatcccgtc gtctctgagt ctcgtacagc tgcattctgg gcagatgcaa gtcttccagt  20520
cgccacatcg tttcaaagta gtgtgtgcgg gtcgacgctg ggtaaatcc cggttgtcga  20580
tttccaccat cattcgcgcg gcagccaaag agaagaagca acgtgtctgg tacgtcgcac  20640
```

-continued

```
cgacgtacca gatggctcgc cagatcttgt gggatgacct gcaggaagtt ctgccgcgta  20700
aatgggttcg taagaaaaac gacaccacga tgaccatcgt gctgaagaac ggctctgaaa  20760
tcgcgctgaa aggtgcggat aagcccgata cgcttcgtgg tgtggcactg cactttgtgg  20820
tgctcgatga atttcaggat atgaagccgg atacctggta caaggtactt cgtccgacac  20880
tgtcctcaac ccgtggcggt gcgctgatca tcggtacgcc aaaaggcttc tccgagttcc  20940
acaagctgtg gactatcggt cagaacaaag atttgcaacg caaagggcag tggaagagct  21000
ggcagttcgt tacggccgat tctccgttcg taccgagcgc ggaaatcgaa gcggcgaaga  21060
acgatatgga ccctaaatcg ttcgcacagg aatacctggc cagcttcgaa aacatgtccg  21120
gacgcgttta ctacccgttc gaccgcaatg tgcatgtgaa gccactccag ttcaatccga  21180
aactgccgat ctgggttggt caggacttca acatcgaccc tatgtcatcg gtcatcctgc  21240
agccgcagcc aaatggtgag ttgtgggccg tggacgaggt tgtgctgttc tcttccaaca  21300
cggctgaagt gtgtgatgag ctggagcgcc gtttctggcg ctggaagtct caggtcacta  21360
tcttccctga cccggctggt gcgtatcgcc agcacgcacg cggcgaatct gacgtcgata  21420
tattcaagga aaaaggtttc ctccgagtcg attatccgaa gaagcacccg cctatcgcag  21480
accgtgtgaa cgccgtgaac cggatgttga tgagtgcctc gggcgaaacc cggttgtaca  21540
tcgatccgaa gtgcaaacat ctcatcgact cgctggagaa ggtgatctac aagccaggct  21600
cacgcgatat ggataagact ggcggcatcg aacacagtgc ggatgcgttg ggttatccgg  21660
ttcatcgtag gtatccggtg aaaaatcgtg ttattcttgg tggatctaga taagtaagtg  21720
cctacctaaa tatggaaaag aaacaaatgg aattgactga taagcaaatc aaggaccttg  21780
tggcacgacg ccacccggaa tatgagaaga aaaaagaaca ttgggatttc ctcgccagca  21840
cctacgctgg cgggcgtgcc tggttcaacg acaatatctt tcgttacttc aaagagggcg  21900
atcaggagtt caaagagcgt ctggaacgtg cctatcgctt caaccacact cgtgaagtgg  21960
taaacctcat caacaaatac ctcttcaaag aggtcattca tcgcaacacg gatgaagcac  22020
cggagcagat ccgcaatttc tggaagcgag ccacgcgcca gaacgcctcc atcgatgcgt  22080
ttatggcggc tatcgatctg caatcatcca tctatggtcg catctgggtt gttgtggaca  22140
gcaccatgaa cgtcgatgtt gagtctgttg cagacgagaa gaaaaatgat gcgcgcgcct  22200
acgcttactg gatttcgccg cagcagctgc ttgatgttgc ctgggacgaa gacggcaata  22260
tgttgtgggc gctgattgtt gaaatcgcgc gcgacgacga agatccgttc acgtcaaccg  22320
ggcaggaata ccagcgttac cgtctgtgga cgcaaaacga gtggtatctg ttccgtgaag  22380
aagtgaagaa aggttccgga aatagcggtc gtcgtcaggc caaagtcgtt ctggaggata  22440
gcggcgagca taatctgggc gtggtgccgg tgttcccggt ggattgcatt ggtgaaagcg  22500
agtctccgta tttcagcccg tcgttgattg atgatatcgc ctatcttgac cgcgccgtgg  22560
ccaactacct gtcgaacctt gatgcgatta ttcaggatca gacattcagc cagttggcga  22620
tcccggttca gtcattgctg ccgggcgatg aaaaccacac caaagtgctc gaaatgggga  22680
caaaacgcgt cttcaccttc gactctgaga gcggtaatca gccattctat ctgtctccag  22740
acccgaaaca ggcccagatg atcatcacca cgattaagac ggtgattaac gagatctacc  22800
actccgttgg tgtggcaggt gagcgaacca agcaggataa cgcacagggc atcgataact  22860
cttcgggcgc agcgaagatg tacgacttcc agcgcgttaa cagtctgctg gtgacaaaag  22920
cagaacgcct cgaaagggca gagcgccaga tgatgcaact ggcagcgaaa tggatgggtg  22980
```

-continued

```
tcgaactgga tgaagaccac tctctgatcg cgtacccgga aagttttgac attcgcggtc  23040
tgactgacga gtttgccgtt gctgagaaac tgtcgctgct ccaggcgcct gattctgttc  23100
gtcgtcatca gatggaaatg ctcatcgaga aggtcttccc gaacatttct gaggcgatgc  23160
aaaaggaatt tcaaaaagat ctcttgaaat ttcctccaaa aaatgatctt aacacccttg  23220
aaaataagtc agtacttact tatgatcgag atatatccca agaaagcggg caagatcaac  23280
cccgagggaa tggggactca tctactcaag agaccgagtg ataagtaacg aaaaggaatt  23340
tctatgaatc tgtggcaaat gcttatggcc cgtcgtggcc tgatggatgc agctgaagcg  23400
catgagcgcg gaggcgctgg tggcggtgct cctgctggag acaacgagca gggcaatcaa  23460
gacccaggta aacagggcga gcaaaaagag caaccgaagg gtgacgacga cgagtatgcc  23520
ggtatgactc aggaagagtt gctggcagaa ctgcgtaagt ccaagaaagc tggtgctgac  23580
ctgctgaaag agaacatgaa gcgcaaggag aaagagcgca cattggccga tcagctggct  23640
cagtacggtg atattgaccc ggcgcgtgct cgccagcttc tcgaagctga acaagccgca  23700
gaaaccgcac gccgggaggc ggagcaggct gaactggaac gccgtggtga gttcgatgct  23760
gtgaaaaagc agatgatcga agcgcaccca ccaggctgaa ctggcacagc gcgacgaacg  23820
ctactccgct ctggagagcg agaacgccga actgaaggct caactggtcg aaatgactgt  23880
tggcgcttcc ttcagcggct ctgccttcct gcgtgacaaa gttctgatga ctccggctaa  23940
ggctcgcgtt atctacggct ctcatttcga agtgggtgaa gacggtagtg ttgtgggctt  24000
tgataagcca gccggtcaga aagagcgtgc agttctggtt gacggtgaag gcaaaccgtt  24060
accgttcgaa tccgcgattg aacgcattct gcgtgcagat ccggaagctg acgcactgtt  24120
gcgcagcgaa gccaagcagg gtgctggttc caatagcaaa ccgacccaca aagtaaacca  24180
gccgaagagc aagtcgacta tggataagtt gacctccggt ctggggaaaa tcggactcaa  24240
gtaacatctt aaatcatagg gaaatgaaag atgccattac tgcgtgatga agctgaaaag  24300
ctatctaaca acgaacttga gcagggtgtg atcgagacca tcatcgatcg cgatgacctg  24360
ttcgctgttc tgcctttcat gaagattaac tctaaggcat acctctacaa ccgcgaagct  24420
accctgagcg aagcaacctt cattgatgtg aacgacacca tcaccgaagg cgctgcaacc  24480
ttcaccgaac acgttgcgaa gctgcgtatc ctggcaggcg acgtagacgt cgacaaattc  24540
ctggcgacca ctatgtccga caccaacaac cagctggcaa tccaggttcg tcagaaggtg  24600
aaaggtctgg cccgcgcatt ccgccgcaac ctgattctgg gcgactccac caccaacacc  24660
aaagctttcg acggtattcc gaagctgatg cacgacgatc agaagatcga catcgaaggc  24720
gcttccatga ccttctccat gttcgacgag ctggtcgacg cggtgaaaga tctgggcgca  24780
gactgcatca tgatgcgttc cgagcacctg cgtgcttatc gcgctctgct gcgtaccgtt  24840
agcctcggcc cgtcagaaat catgatggaa aacttcggcc gcccgatgct gtgccacaac  24900
ggtgtaccgt tcatcgtgaa cgacttcatc ccgactgatg ctggcaaagc aagcatctac  24960
tgcctgcacc tgtccgaaga gaacggtgtg accggtctgt atggcggcga aaacgccggt  25020
atcgttgttg agaacatcgg tactgttcag aacaaagacg caacccgtac ccgcgttaag  25080
tggtactgct ctctggcgaa caagcacgat aaggctatcg ccgcgctgac caacgtaaaa  25140
atttgatcag tatcgtaggt aagtaattat ctaccattta agggtgggct atacgcccac  25200
cctttttgta ggagcgagaa atgccagaac aaaagatgaa gatcacggaa gaggcgtttt  25260
cggatttcac ggggcatatg tgccgtgccg gattcaccaa ttccatctcc aacgagcctc  25320
tgagcgagcg ccagcagaat catcttgcgg cttgcttccg ggcaattccg ttcactcagt  25380
```

-continued

```
ctgtcaccat tacaccgact gcgccgtccg tattggtggg caaaaccgtt caacttagtg  25440
caggtatcac catgagcaaa agtgcagatt cattcacctg gacgtcagac aatgaccggg  25500
tcgccacagt cagcggtacg ggtctggtta ctggcgtgac tccgggcaaa gtgaagatca  25560
ccgccaccga taagcagact cagctttctg cctcagtcga agtgatcgtt aagcctgtca  25620
gcgtggagtc cgtaaccgta acgcctgact ctacctccgt tgagaagggg aaatcggtca  25680
agttgcgtgt tgatgtacaa ccgtcaaatg caaccaataa aaaagtcacc tggacttcca  25740
aaaatagcga caaagcgact gttgaccaga acggtaacgt agctggcgta gccgttggta  25800
cggcaactat tgaagtggtt tcgcaggatg gcagccacaa agctactgcg actgtggaag  25860
tgactgcagc accggctgcg taaccaatac atgggcggca tagccgccca ttaagtgaga  25920
agaagaatga aaccagcaaa aattcgttta ttggagcctc aatttttggg gtacacgggc  25980
attctctgcg gtatccagtt tgtcgacggc atctcggttg ccgaactgcg attcatcgat  26040
cagcagcgga tttgtgcctc catgcgtgcc actaccgttg aaggcaaaaa tgtatctcct  26100
tctgccgcgt acagcagccg caatgatttg actgcggacg acattgtcga gacggcggcc  26160
ccggatattg tgccaatgaa acgtggtaca gctgaagtgg aagccaaacc ggtacagcgc  26220
tttactcgtg aagaactgga gtcgattgcg gactgtgaag gtattgcggg tctgcgtcag  26280
atcggcaacc agattggcgt gaaagccaaa ggcatcgttg aaatgatcga aggcatcctg  26340
aaagcacagg gcggtgagta atggcgcaga tcgacacgta ccgtagcggg gaagctgttt  26400
ccctgtcgtt tgcatttaac gttctggata ttgagtcggc cacgtatacc gtcagagatg  26460
gcgctggcgc gatcatcgtc gataacgaac ctctcgatat tactgagggg cagatgtcca  26520
ttccggttgt cgtgtcggcc gaacacaacc tgctttcaga taaagagcgc gatctgcgac  26580
acgtcattgt caaagcggtg gcatccgggc tgacgcatga agagcgcaag atgtacgttt  26640
tgctgaatag cttcgagctg tcaattccag gccagtcatt cgcaacggtc gcagacgccc  26700
agatgcaagc tatcgatatg ctgaacggcg acaccctgtt agctgatggc gaagggctga  26760
tgcgcaaacg tctcattgag gccaccagac gcgtcaaaac gctgccgttc tcaatccgca  26820
aagtcctgcg tatcgacttc gaccggtacg atcgcccgca aaacatgctg aacgtctatg  26880
acattccgtg gggcgctgac ggggcatatc gtcacgatct gatcgattgg gagcagatga  26940
cgccggagaa attcgacgag ttcccggact acttcaaaca ggcattaatg ctggccgtgg  27000
ttaatgaagc ctgcgaaatc gctaacggta atgacgtagc ggcagcccgc gaggacggca  27060
ttctgtctga gtccattggc gaaacgacca atatgtaccg taccggcaaa gcggcaaacg  27120
tgcaggtggc tcgcagtacc tggcgactgc tggtcagtta catcaataac cgcatgattg  27180
ttcgccgtgc gtaacgccag tcgcattatt tacttctggt cgaaaggctc aagacgagca  27240
atcgcgcctt cgcctggtaa tgagtgcggc tgccaaccac agggagagtg catgaacatt  27300
tcatggcaag cagagatagc gatttaccgt ctgggttcga agaacgtcta cggtgaagcg  27360
caattgcagt tcgtcagaaa gacgaacgtc ggcgtcgtta agtttgagca aagtaacgag  27420
aagtcatcgg tacgtgctga cagctccggc agtcgcggta aagcgaatct ggaattgttc  27480
gatgctgttc tggtgatccc acttgaggcc gcagtacagc ttgatgacgt tctcattctg  27540
gaggggcaaa agctgaaggt atccagcgtg catcgtcgct ggggactgcg tgggcgccct  27600
gggcatctgg aagtaggggc aaacatatgg gtctgaagta cgacgcgcat cattttaagc  27660
gtgctggcga caggctcaat aacagccaga aagcctttaa gcgttatctc atccgtgaca  27720
```

-continued

```
tggagaagct ggcgcgtctg gttgagcgtc tggcgcgggc aatggccccg ctggagactg  27780
gctcactcga aagcgcgatc ttcgcgagag ttgtcaaaga aggctatacc gggctgcgta  27840
ttgagttatc ggtatctgga gccaaaccac gcgaaggtca tccgggcgtt gaggttggcg  27900
attatgcgga gtacatggag ttgggcaagt atcgtctcgg ctatctatcc cgcatgaaga  27960
gcgtcaccaa cccgccagtt gctggagtga agccacgagt tgggcctttg ttccttgaga  28020
gagccgtgca gatcagtgag aaacagttca ctcagacgat agcagaagcg gcaaggaaag  28080
caggttttac gagaggttga tgtgtttatt gaagcatttg cgagcctgat gcagaaggcg  28140
aagatcggta cagtcggcac tgacattttc tgtcactaca tgccagccaa tgtgaagtcc  28200
ggtgttctgt tggttactcc caatacgggg atcaccattg accatgagtt aaaaggcttc  28260
tatcacgact ctttcaccgt catcgtgcgt aatgcgacga ttacaaagac ggtggcgaaa  28320
gccaataaga tcatggacat gttcccggtc gaagaaaccg tgtcagatgg cgtttacttc  28380
cggttggttc gaccaatgtc gatgccgatt acttatccca aaaatgaagg ttcgttgatt  28440
gaagcgggta tcccgattga atttgcgggc tatttgttga attaataaaa taggtaagta  28500
tatacttatc attaacacca tgaaggtgct gatttaacgg aaaaaggagt tttccaaaaa  28560
tgtccaatac ccatgtaaaa aacatcaaac ttggcgcctg caaagtgtcg tttggtggcg  28620
ttgatctggg ttacaccaaa ggcggtgttc aggttgaagt tgcgaccgaa actctgaaag  28680
tcaccgtaga ccagctgggg cagaccacca tctccgagct ggtacagggt cgtaacatca  28740
ctatcactgc gccgctggcc gagtctgtgt tgcagaatat ggtcgatctg atgccgggtt  28800
ctaccctgag cgaagaagag aactctgtga ccatcacttc cgcacagggc gtcaacctga  28860
tcgacgtagc caaagagctg gttctgaccc cgcaagatac caccgactat gtcctgacca  28920
tcccgaaagc tgcaaccgca ggtaacttca ccatgaccta ccagtctgat gatgttcgcg  28980
tgttctccgt tcagttcacc gcttacccgg atgacgacgg cgtgctgggg aaaatgagcg  29040
gcccaaagcc ggttaaaacc gtctctatct ctccggaatc tccggaagtt aaagccggtg  29100
agaccgtgca actgactgcc cagatcaccc ctgcagatgc cggcgacaaa accggtgtgt  29160
gggaatccga caatcaggag aaagcaaccg ttgaccagac tggtctggtt cgcggagtag  29220
ctgaaggttc ggcaaatatc tcctttacca gcaatagcgg cggcaagaaa gcgaccaaag  29280
cagtaacggt taattctgcc caataatcgc gacgtaatta agcagaggct caggaagagc  29340
ctctctttta aaggacttt aaccaatgac caaattactc gatctcgact ccattctgcc  29400
tccgaagaaa agcatcaagt tcggcggtca ggaatatccc atcgttgaaa tgactgttgg  29460
cctgttcgtc tctatcaagc agatggaagg caaagacctc cagaatatgt cgcctgttga  29520
gcaggttact gcttacgccg acctggttcg caaggtcatc ccatccgtgc cggacgctgt  29580
actggaaaaa ctgactgttc cgcagctcca gcagatcttc accttcgcta tggaagtgat  29640
tgatgaagag aacgaaaaag cggctggtga aggggcaaag taatttcccg cgatgaatcc  29700
ggggtaaaga ccgtatcgat agatctcgga ttctatttca gtcgtgtagt tgctcactac  29760
gccgtgtcgc cattagagct gctgggcgtc cctctaacga tgttctggat gctcagtcgc  29820
aacatcgacc gtctgcgtgc ggaagaggat gtccgcaacc tgcaagtcgc tcgcgctgcc  29880
caggcagatg gcgagggcgt aaaggcgttc atggagggtt tgcaactcag gattggaaga  29940
ccagtcgtaa ccgataaagt ctacgatcca cgcaaggata aggcagaccc tgacgccaaa  30000
gagcaactga tgcaaatttt tggcagagga tgacaaggga atgtcacaaa acgtagagtt  30060
tatcctgtcg ctggaagaca agcagtttac agcgtcaatc gaccgggcgg gtaagctact  30120
```

-continued taccagattc ggggagcagg ccacaaagcc agctcagaaa attaacaatc tggaacgctc 30180
gttgggttcg gtctcccgca tcatcggcgt tctggagtcc aagctcgatg tcacggcaga 30240
aaaactacag gatgtagctg ccggcttcga gcttgtgtct gatgtttcgc gcaagacgcg 30300
aggcagcatt accagcctca actcaggtct caaaaccctg attgagcgcg tcgacacaac 30360
cacctcatcc gttaataagc tcaccacatc gctgcgcaag gttcagtctg aactcaatga 30420
gttttccgat tgggcaacgt tcgctggcaa gagcgccagc cgcttcggta cggaggtaaa 30480
agaagcctct gcatccgtga gcggcatgaa tacgcgtctt aacaccacga caaagcgtct 30540
cagtaattgg ggtgtcacaa cgagccaggc tgctgagggg ctgaagaaag tccgcgatca 30600
gatggatgcg gtgattggcc gccagcaact gatcagcaag ccggtacgtg tacgcaccag 30660
tagctacggt gatggcggtg gtaatggcgg tggaggtcga cacagcggtt cctatggcca 30720
cggtgggcgt agtgctgaaa gtggtgtgtt ctctggtctg cgcggcaaca ttttcttgct 30780
tggcgagatt ggtgatgcgg caagaacggt aactgacatc ctgttcggct ggcagaagcc 30840
aatcatcgaa gccgcctccg aaatggagcg tatgcgtgtc atgttgcgcg ggctgaacaa 30900
ggataaggcc aaccctggaa aagccgccgc agaggatatg cagtacatcg tggatatggc 30960
gcaaaacgcc ccgtttgcga tgcaggcgct gaccgattcc ttcgttaaat ttcgctcggc 31020
aggtctcgat cctactgacg gatcgctgaa agcactggtg gactccgttg cacgcttcgg 31080
cggcgatagc gaactgctta aacgtgctgc cgtggctgtc cagcagatgt ccggtaaggg 31140
cgtcgtgtcg atggaagaac tgcgtcagca attaggtgaa gccgttccta acgcgatgaa 31200
ggcgatggca gacgctgccg gtatcactat gggggaactg accaaagcag tctccaccgg 31260
tactgtggaa gcgaaacagg cgctatcgct gatgttcgtt ggtctgcgtg cggagaacga 31320
aaacgccgcc aaagacatga tgcaaaccta caccggtgcg ctggcgcaac tgcaaacctc 31380
ctttacgctg tttgccgatc gtgtcggtca ggcgggctat ctggattctc tcacaaaggg 31440
gatgaaagag cttgcttcca tcatgaacag cgctgaaggc atttcgttcg ctaactcgct 31500
gggttccgga ctctccacgg cgatcgacgg cttacgcgag ctggcgcagt ggctggctaa 31560
aaaccaggag ctggttatca gcctgggcaa agtcgttgcc gcaatggtgg cgttcaagct 31620
gatgcgtgcc gggattgcag gcgtgattgg cactgccggg caaatggtta acacatttac 31680
caagatgtcg accgttctcc aggctccgtt caatctgggc gcgacagctg tcacccgctt 31740
taatcgtgcg gctcgtatgg ggctggcccc aatcccatcg ctgatcttcg ctatccgtgg 31800
cgcgattacg gggcttcagg gcgcgtttgc tgggctaact gcgttcattg cagcaaaccc 31860
aattggtgca gcgttcaccg tagctaccgt ggctgtggcc ggtcttatca cgtatatgac 31920
catgctccgc agcgaaacgt ccaaagtcgt ggacgagatc cgcaaaatcc cggaggcgat 31980
gacggcggcc aagcgtgcgc agatggcagc gcgtgcagcc gagcttgaaa agcagatcca 32040
gcgagaccag caggcgctta aaactggcga aagcgtgaac tactactcca cagcggctgg 32100
ccctgtcgcc gtgaaggagt ccaaagaggt tgttgaggct cgcctgaaga aaaatcagga 32160
agagtacgaa agaacaaccg gcacgatggc gctgggtgat ggcgcagtgg ccaaacgcct 32220
ggcaaaagaa gctgccgaat cccagattga gaaaatccgg gcagataacc aggtcttctc 32280
tgcgacgttt gtgaaagccc gtcaggaggc tctggataag atccagaaaa tcaacgacga 32340
caaatcgctt tcggacgacg agaagaacaa gctgcttgca ccgcttcgcg agaaggtgaa 32400
caagtcctat ctggaaccgg cacagaagct ggtctacgac ctgtcttctc gtaaaaacgc 32460

-continued

```
caccgagaag caaattgccc acttcagcga catgctggag aaagcgaaga aagaggggaa  32520
caccgagcag gttcagaagc tgcagggcag catccgcggg tatcaggagc atcttgaagc  32580
tgtagctcag gagctgactc aggcggagtt cgagcgtgat agcgcggcga aaaccggtaa  32640
gggcgtaatg tccaaccagg gcaccgttct ggggttgggg acgaccgata aggcggctca  32700
gaaagcactg gcgcagtata tgcggaacca gatggactcc gcgacctacc agcgcacact  32760
gccagacggt acggcgatgc tggacttcga aggcaagccg atcatcgggc cgaaacagct  32820
caaaacccag ctgaacctgc agaaagcctc cagcgccagc tctctggaga aaatgagcga  32880
cgaggaacgt gctgccgcga tcgccgcact gaccaaagcg cgtgagcagg acgcagcagc  32940
agcggaaaaa gccgggcagc gtactgccaa tgcttctcag cgtgccgcga ggaaggaaga  33000
aaatgcgcag cgtaagctgg cggccggcta ccagaaagcc ctggataaag ccgatcagct  33060
tatggggcag atgggggaaa gctcaaaagc gaccgtgtcg tttgaccagt ctctccgcga  33120
taccaccaaa tcgctgaccg aactggccaa cgccgtaccg aatgagttca tcactcagga  33180
gatgatcgac aaagccaagt cacgcctcgc tgacctggcg aacgcgagcg acgactatcg  33240
cgagatgttc aaccgccgca acgtcgagca gatgatctcc acctgggcgc cggaatccga  33300
ttccatcatc agcgcgggtt acaagccgtc tcgtgaagag aaggtggccg atttcaacga  33360
cacctacaac cgtaatctga aagcgttgat ggatttgcgt gaccaggctt ctgatccgaa  33420
aatcgtggcg ctctacacca agcagattaa ccagctggtg gcggcaggca acaccgcgct  33480
catcaaagag acgggtacgg cgacacagaa gctggcgctt gagtacgaga atctggccga  33540
acagctggaa aacagctgga gcaacctgtt cagcaacatg acggatacgc tgaccgactt  33600
cgtcatgaag gggaaactgg acttctccag cctggcagag tccattctcc gcgacatcac  33660
caacatggtt gtgaagacgc agatcactct acctctcatg aacatgctgg ggatggggac  33720
gacggcagcg ggcagctctc agagtggcaa tctgctttct ggtgtcgcgt ctgcggttgc  33780
caaccagggc gtccggatga atgcggtcaa cggcgataag agcgtgggtg aggcgacgaa  33840
agagacctcc agctcggtct ccggtctggg gcagaccact cagcagacga ccagcgcgat  33900
tggttctgca accaacgcga tcggcaactg ggtaaatgga ctgttcacca gtactgaagc  33960
caaagacgcg gaaaccaaag cggtgaagac gtccatcttc tccatgcaga accttagctc  34020
tgtcacgggg gcgctttctg ccgcgtttgc tatgctgggc gcaaacatgt ccggctctgg  34080
caataagtgg ttgagtttcg gcgctaccat tgcctccggg ctggtgtctg cctgggctgg  34140
tggtggcttc gataacatcg gatctggttc ctccggctct aactccggat tcaacaatct  34200
caccggatcg gcatctgatg gtactggcgg cattccggca atcccgaagt tcgccaaagg  34260
cggcattttc gggaaagacg gcgtggttcc gctgcgtgct taccagaaag gtggcatcgc  34320
tgactctcca cagctggcgt tatttggcga aggggatatg aacgaagcct acgttcctct  34380
tccggatggg cgttccatcc cggtcacgct caacgcagag ggtgttaaag gcggcggcgt  34440
tttctcacct gtcagcattg aaatcaacgt caacagcgac ggcagtgtct cggagaacag  34500
caattccgaa ggcgcatgga gtcaggctgc gcagcgcatg aaggcgatcg cgcttgaaac  34560
catcgctcag gagaagcggc caggcggttc gctcaaccct aactctcaac gtaactaacc  34620
acggctgccc cggaaggggc ggtctcacaa ggatgtgaga tggaaagact gacttttaac  34680
tggtatcccg actacgagtc ggaaaagacc gtgaagccta acgtgacggt gctgaatttc  34740
ggtgacgatt acgaacagcg tcaggcaaaa gggcttaatc gcattaaaga agagtggagc  34800
cttactttta cgcgttctta tgacgtcatc aatgccgtcg atgactttct gacggcacgc  34860
```

-continued

```
gcggccgttg agtcgttcta ctggacgaac cctcgaggca aaaagatggt tgtggtgtgc  34920
gacagccata ctgtgaagcg ttatcagggc tatctcgttc tcactgcgac cttccgacaa  34980
atttatgaag gataatttaa cccactagat aagtaggtgc ttatttacta ttatctatag  35040
gcgctgacag gatgttggcg cctctttatt tcaaggaaga aacgatgggt attaaagctg  35100
atattcagag cttgtcgccc tccgcgctca ttgagctgtt cgaacttgat atgtcgaaca  35160
ccacctctgg gggcaagctg tttttccacg ccggtacaaa cgaactgatg gagccagtcg  35220
tttggcaagg tgtgtcctac gaaccgtggc caatcaaggc gtcaggcttt gataagactg  35280
gtcagggtac tttgccgcgt ccaaaaatcc aggtctccaa ctttgccgga accgtctccg  35340
ctgaagtcca ggcaaatgac tatctggtgg gttgtcgcat catccgcaag atgacgctgg  35400
cgcgttttct cgacgcggcc aacttcaaag acggaaatcc gaccgcagat ccgaatcagc  35460
atttcccga tgagatgtgg ttcgtcgagc agaagactct tgaaacccat gaggttgtcg  35520
agtttgagct gtcgagcgtg ttcgatctga tgggcgtgca actgccgtac cgccagatca  35580
tcaaaaacac ctgcccgtgg aaataccgcg gcccagagtg cggctatacc ggcccctatt  35640
tcgacaaaaa caaccagcaa accaccatgt caggcgcgga ttactgcacg aaacgctacg  35700
actcatgcaa cgcacgccgt aactactttg ccaatggcgt aatccacttt ggcggattca  35760
ttggagcaac acgttatggg taatagagct ttccctgagc ttgggtcgga cattatgcag  35820
gaaatctatc tgacagccat caaacgctac ccgaacgaag cgtgtggctt tctggtgcgt  35880
actactggcg agaaatatcg cttcatggaa gcccggaacg tgtcggagaa cccggaaaac  35940
acgtttgtga tgcacgctga cgacattatc gcagcggaag atgcgggaga cgtggttgcc  36000
atctggcact cccacactga cgaatcagct gatgcgtcag atgccgaccg cgccggatgc  36060
gaggcaacgg aagttccgtg gctgattctg gctgttcgga agaacgtcga gggcgatgcg  36120
ccatttcact tcagtgagat gaatgtgatc accccagacg gctttgagat gccttatctg  36180
ggtcgaccct atgtgttcgg tgtcttcgac tgctggatgc tgtgccgcga ctacctgaag  36240
cgtgagttca acgtcgagct gaatccgaac ccgcacctgc atattccatc gtggtacacg  36300
ggcgataccg acattctcga tcagaactac cgcaatgaag ggcttgttcg tctggcgccg  36360
gggacggaac cccagcgtgg tgacgtcttc ttcattcagt acggaaagat gcctgaccac  36420
tgcgcggtgt acataggaga cggaatgatc ctgcaccacc agatcgaccg tctgagctgt  36480
cgcgcttatt acggtggcat gtaccagaaa cacacgacgc accacctgcg tcacagagac  36540
ttactcaagg gagatgagac gtgtctgagt tagttcatgt gcaacttggt ggcccgatgg  36600
ccagacattt cggccgccac tggcatttaa aagtgcgcaa caccaaacag gcgttggatc  36660
tggtcgaagc caatcgtccg ggcttaaaag cctggatgaa gcgcaacatg aagacctacg  36720
acaagtatca catccagatc accaataagc aggggcataa gtggtcggtt gatgagagcg  36780
agtttcaaat gatggggcag tccgacaaca tcgcgaagat ccgcatcacg ccggttcctc  36840
gcggtagcgg cggtaaggct tttggttggt ttcagacagt cgtaggggca ctcgtcatgg  36900
ttgcctcatt ctggtttccc gcgctggccc cgctcggctt gtcgctaatg atggggggta  36960
tttcgcagtt aatttcgccc caggcgacca atgacagtgt aaggcaggca gataactcga  37020
actcgtttta tttcgacgga ccacaaaaca ccactaacca gggcaacccg gttcagctca  37080
tttatggtga ggaaattctg gtcggctcac aggtagtaag ttcttcgatc accatcgacc  37140
agctttagta agaagggaaa tttttgaaca tggaacagtt caagaagaag agactgcctc  37200
```

-continued

```
tcctgattgc aggtgctggc ggtaagaaaa gcagtggctc cagccgcaca ccggttgaag  37260
ccgacgatac cgtaaactcg cgtgctatgg cgtccatcct cgacctgctc ggggaaggtg  37320
tcattggcgg gctggtggat ggtgcaaagt cgatcttcgt tgatgatctg ccaatcctta  37380
acgaagacgg gtcttcaaac tttagcggta tcacctggga cttccgcgat ggttcacaag  37440
accagacgcc gatggctggg ttcgatttcg ttgaaacgcc gaagtcagtc aacatccagt  37500
tgaaaagaat gcacgacgtt acgattgcca tcgataacga tgaggcagac cgtgtccgcg  37560
tcattctgaa gttcccgtct ctgcgtagca tcgacaaaaa gaccggtgat accaacggta  37620
cgaccgtgaa gtacaaattc cagattgcca atggcgataa tgccttcaag gacgccatcg  37680
cagaagggga gagtgcttcc gaaattgcgc tgacggcaaa aaagacaggc gtctactacc  37740
gcagctatga gctaaaactg cccaagccag gtcgtgccta caaggttcgc gtgctgcgtc  37800
tgaccgatga cagcaatact cagtacatct ttaacgatac gtgggtggac tctatcggtg  37860
agatcgtcga tacgccgatg aactatccga actccgcgct ggttggcctc aaggtcaact  37920
cagagcagtt cggcagctcg atgccgtctc gttcgtatct ggtgcgtggc ctgaagatcc  37980
gcgtaccgtc caactacgat gaacacacaa acacctatat cggcgtatgg gatggcacat  38040
tcaagctgtt gtcatcttcc aaccctgcct ggattctctt cgacctgctt accaacgctc  38100
gttatggcct ggggcagtac gtttctgagt ccatgattga cctcgggcag atctaccaga  38160
ttggtcgcta ctgtgacgaa gaaattgaca atggattcgg gggcaaagag aagcgcttcg  38220
ctatcaacac ccagatcact agccgtcagg acgcgtaccg actgattcag gatatcgctg  38280
gcgccttccg cggtatggtc ttctgggctg gtggcatggt taacgtcatg caggatagtc  38340
cgtcagatcc ggtcatgatg ttcaccaacg cgaacgtcaa agacggcatg ttcagctaca  38400
agggatctgc gcgtaaagac cgtccgtcag tagctcttgt gacctacaac aacaaggaag  38460
acggctacaa gcagaacatc gagtacgtcg aagaccagga ggcgatgcgt cgttatggcg  38520
agcgtaaaac cgaagtggtt gcgttcggct gtacaagccg tggccaggcg catcgtgtcg  38580
gtctgtggct gctgtatacc gcacgcatgg agtcggacgt tatcagcttt acggcagggc  38640
ttgatgcttc cttccttatg ccgggtgaaa cggtgctgat tcagaacaaa taccgtgctg  38700
gtaaacgcaa ctctggccgc attgtggcgt tcacaaagaa cagcatcact ctcgacgcac  38760
cggttacgct gaataaagcc ggtagctaca tccggatctt gaatcaggaa ggcgaaatcg  38820
ttgagcgcga tattcttgag accggggaag acattaccaa agtgaccttc tccaaagcgc  38880
tcaattccgg tgatatgccg gtgatgaatg gcgtctggac gattaccgag ccagatctgg  38940
agccaatgcg cgtgcgtgtt atcaacgttg cccagggcga ggctcagggg acgtttaacg  39000
ttacggttgt ccagaataat gcatcgaagt acgaagccat cgacaacggt gcgacgctga  39060
tccccgagaa caacacagtt ctcgacccga cttattcgaa gccgactaac ctgcaggtga  39120
cggaagggac gtatatctcc agtccgggta acctctcaat caagctcgta gccacctggg  39180
agggtaagtc tgcggaatat tggatcagct ggcgtcgttc cgatgaaaac aacgtttcta  39240
actggcagtc cgcacgcgtt accgaagagc agttcgagat cctcaatatt gctgagaatg  39300
gtcaatacga cattcagctc tatgcggttt cgttcagcgg caagaaaacg gacatcatca  39360
gcaccgttta tcaggtgaaa ggtacgatga cgccgccagg ctctcctacc tctctgacgg  39420
ccgttggtga ctaccgcaac gtgattctga attgggtcaa cccggactca atcgaccttg  39480
atcacatcaa cgtgtatgcc tcccagacca acgatctgga aacggcgaag ttggttgcag  39540
aggccgccag caccacgttc actcatgccg gtctgggaga tagtgagacc tggtactatt  39600
```

-continued

```
gggttcgcgc ggtgaacaag cgtggcatgt taagtccgcc gaactccaat ctgggtacgg  39660
aagcgatgac gcgagacgtc ctctcgttcc ttaccgggaa gatcacctct tccgagctgg  39720
ggcaggagct gctggaggaa atcgacgcta aagcctctca ggatgcggtc gacgccatca  39780
acaaacagat ggaagagagt ctgaaagagc ttgatcagtc cgttgccgat ctggacagca  39840
aactggaaga caccagcggt cggcttgagc aggtgcagaa cgacctcaaa aatgaagtct  39900
ctggcacgct ggacaaggtc aacgacgcgc tgcaacaagt tgaggactct aatgcggctc  39960
tggtcgagtt gcaggaaacc gtttccgagc agggcaaagc catagctggc gctgtggaag  40020
cggcgcacgc tgcgctcgac aacgcctccg cgctgattgc tgaagagcgt gaagcccgtg  40080
tcgaaggtga taaggcaaat gccaaacaga ttgaggcaat gaaatcctcc gtcgatgaca  40140
gtgttgccgc cgtcgaagag atgaaaaaga ccgttgccga agtcgaacgc gccagcgcgg  40200
aagcgtcgac caatatcgag gctctggcca aaaccaatat tgacctcgct ctgcgtcagg  40260
atgaagacca gcacaagcag atggtcaata atgcgaagat cgcaaccact cagaagacgt  40320
ttgccgacga tatgtctgca atggcctcaa aagtggaaga aatccgcgca gaaattggtg  40380
aggacatccg ggcgtcgatt ctggaagaga caacggctcg cgtagaggct gacaagacaa  40440
ttgcgacgca tatctccaag ctggaagccc agctcaacga cgatatttca gcggcaatcg  40500
tttccgagca agaggcgcgt gcgactgcgg atgaaacgct ttctcgtcag atcaccacgt  40560
tgcaggcgaa agttgaaggt gatatcagcg ctgcacttac tgaagagcag attgcccgag  40620
ccacagcgga tgaggcgcta tcgaagcaaa ttacccaact gaaggcacag aatggtgagg  40680
atatcaaagc cgccgttgca gaagagaccc aggctcgaac cgatgcagat ggtgctctgg  40740
cttcgcagat cagctcgctg aaggctcaga cggcagagga catcaaggcc gctgtcgaca  40800
cagagacgaa agcgcgtacc gatgccgact ctgctctggc cgggcagatc accaatctcc  40860
aggctcagac cggcaaagat atcaacgctg ctatcacatc cgaagccacc gcgcgtgcaa  40920
acgctgacgg tgctctcggt aagagaattg atacggttaa ggctgaagtt gatggcaact  40980
cggctctcat tcagcagcaa gcgaaggcga ttgccgatac cgataagaag gtttctgctg  41040
cctggacgct gaagatggaa acatctacca gcggcgggca gaagtacgtt gcaggtatcg  41100
cgctgggtat cgacagtacc ggtttatcac aatttttggt gcaggcagac cgttttggcc  41160
tggtcaactc cgtaaacggg aagatcacta cgccatttgt catcgaaaac agcgtggcgt  41220
atatgaacgg cgcttatatc aaagacggca caattacgaa cgccaaaatt ggtaatgtca  41280
ttcagtcgaa cgattacgcc gcaggcagta gaggctggat tatccccaaa gatggtagcc  41340
ctgagttcaa caacggtacg ttcaggggaa atattgctgc aaactccggc acgctgaata  41400
acgtcaccat cgcgcagaac tgccagattc tggggaaact gcacgcgaac cagattgatg  41460
gcgatattgt taaagcctac atggttaatg gcagcagtat ttatattgca cctcaaacat  41520
tcgccagaat tatctatgtg gtaaatggtt actactataa caagccatcg gaggatatta  41580
acacctactc atggtcaaga attaccgagt atacggtaaa tggagtgaag cagcagatat  41640
atggaatgag agaaggctct aaaaatcaat ctggcttgtt tggttattac aatttgccgg  41700
caggtcagtc tgcgactgtt gatgtttata cctggcatag acagcgtaaa tacgatcacc  41760
gcgtgaatga accttatctc attctggtgt ttaaggctta aaaatggaga aggatattat  41820
ggacgaaacc cctgtcatct ctgctgtaag gaacgcagtg cgcagtctta gtggcggtat  41880
ctcttgtgag attcaatttg atggccttgt tatggacgat ggtgtaaccc ctttgttttt  41940
```

-continued

```
gccatacacg ttgtcggaaa gtgacacatc acctttggcc aagaaaatac tggaggctct  42000
ggagtcggaa tccagtggtg gtatcgctcc gtaccccgaa caaggcgagt acatcgaaag  42060
attgaaagtt gagaaactgg cagtaattaa tgactggcgt cttcgtcagg agtgtcgcac  42120
cgtttatttc gaatggaacg gccaccgctg ggacgcgaat gacatttcca aagaacgttt  42180
ggatatctcg cttaaagcag cggaaagcgg tctccctgac aatttcttct ggaccgatgc  42240
ggataataac gatgttccgg taacgcagga gcaactgaag gaattaggga tgagaatgac  42300
ccagacgttg ttcgaccgca agttcggcgc ccacgaacga cagagggtga tgaaaaaaga  42360
cattctggag atgtgtgatc ctgagctaat caaaaattat caggtcgggt gggggatgg  42420
ctctgctcgg cggtagacat ctttctttat atcggtaaaa ataagtaagt gattacctat  42480
ggcgagcagg gatgcccgcc tttacaagga gcgaatatgt ggtacaggga aggtactatc  42540
acatttacac agggaagtga cgcactttct ggcactggca cgtactggaa tgtgaccgcc  42600
aacggcgttc tgccgggcat gatcgtcatc ggccctgaca acaagttgta cgaaattaag  42660
cgcgtaatta gcgacacaag tctgattctc gcagagccgt acacagggga gacccagaag  42720
gaagttccgt gccgcatcat cacaacctat gagggcgact taacgcagtt cagcgcacgt  42780
tttaccgcgc ttatgacccg tatgtcagcc gactcgaaga cgatgcgcag ctggttgacg  42840
gcagttgatg aggtaacgct tgagcgtgaa gacggtacgg aagtgaccgt gaagtcgctg  42900
acgcagatcg tcgatgagca caacgcaaac cagaaatggt atacggataa tgcagacgct  42960
attaatgcgg caggcgagaa ggctcgtgag gccgctgagc gcgcattagc tgcggcgcaa  43020
agctcttcag aagcaagagc aaaagcagat gaagccgctc aaagttcagc ttcagcatct  43080
gagtataaaa ctgcggcaga gctaagtgcc gctgcatcaa aagcatcgga gcacggcgcg  43140
gcagaaagcg cagcttcatc gaaggcaagt gcctctgcgg ctaaaacatc tgaagataat  43200
tctgccgcgt cagagaccaa tgcggctgaa agcaaggctg ctgcggcatt aagtgcgtct  43260
tcttcggcaa atagcgcctc agaagcattg caatacgcgg agtcagccaa gacctctaaa  43320
gaggctgctg ctgcttcaga agcagcggca gccaatagtg aaaatgaagc cagaacctca  43380
aaagataccg ctgtagcggc tgcggcagag gcatcagcta atgccacatc agctgatgcc  43440
tccagacatg atgtcgatac caataaagcc gaagtatcga gaatgaaaga tgaagttttc  43500
gctgctaggg actcaacgat tcagtatagc gaagaggcta aaacagcggc tgatacagcg  43560
gcaagagaag cagccacgaa aacatctgat cagctcctgt cggcggttaa atcagaggcg  43620
gaaaaggcaa acagtgctag cgcaagtgct caaggttttg ccgatgacgc caagcgattt  43680
agagacgaag ctcaggaaat agctgaaggc agcaaggtaa acgatgcaac aacctcacag  43740
caggggggttg ttcagttgag tagtgcaact gatagcgaga gtgaaactct tgcctctaca  43800
ccaaaagctg tgaaaacagt catggatgcc gttgctctaa aggctcctat agatagcccc  43860
gcgctatctg gcgcaccaac agctccaact ccggcaatta ctgctgctgg acgtgagatc  43920
gcgacagccg cgtttgtggc ttcaaaagta gcacaacttg ttggctcagc gcctgaagca  43980
ctggatacgt taaatgagct ggctgctgcg ttaggcaatg atccaaactt tgctacgact  44040
attacgaaca tgttggctag aaagcagcct ttggatggaa cactaactgc gctttctggt  44100
cgttcacctc aaggggtaat tgattatctt ggcttgttga atacggttaa cctggcggct  44160
ggctcaattc agaaatccca gaatggggca gatattcctg acaaaagatt atttgtgaaa  44220
aatataggtg cagttagctc cgccagaatt tcgtttgtta aggaatccgg gtggtataag  44280
ttagcgacag taacaatgcc tcaaggagct tcaaccgctt taattactct tattggaggt  44340
```

-continued gctggataca acgcggggct ttatgaccag gcagcgataa gcgaaatagt gttgcgatca 44400
gggaactgga atcctgttgg catcacagca acattatggc aacgctcacc agcaggtgct 44460
caaggggtgg cgtggataaa tacatcagga gatgtttacg atatttatgt aaacgttgga 44520
cagtactcta ttgatgttat tgctctgagc gattgtacaa ataatgcaag catagtgttg 44580
ttcggcacac cagagtatgt ggcgaccaaa cctgcaagtt ccacgaacgg cgcaaattat 44640
atattgtaca gtagtgttct accaccgcct gagtcatatc cagtaggtgc ccctattccg 44700
tggccgaacg atgtggcccc gtctggtttc gccatcatgc aagggcagac gtttgacaag 44760
agtgtgtatc cgaagctggc ggccgcatac ccatcaggtg tgttacctga catgcgtgga 44820
tggatgatta agggtaaacc aacttctcgt gcagtgttgt cactggagca agatggaatt 44880
aagtcacatg cgcacaatgc agccgcttcc agtacagatc ttggtacaaa accaaccaca 44940
acatttgatt acgggacaaa aacgtccagt ggcttcgatt atggaacgaa atcgtctaac 45000
agcactggtg ctcatgcaca ctcgctgtct ggctctacat cgagttcagg tgcccatgcg 45060
catacggtaa ctgctcatac tcagtatcca agatctacag attcgaggaa ccagaatgct 45120
gtcggtaagc aatacaacac acagcagact acagccaatg ctttcaatgt ctggacaagt 45180
agtgcaggtg atcatgccca ctcaatctcc ggtactgctg tcagtgccgg tgctcatgcc 45240
cataccgttg gtattggcgc acatgctcac tcattgagta ttggatcaca ctcgcattca 45300
gtggcaattg gggcgcactc acacactatc actattgccg cttgtggtaa tgcggagaac 45360
accgtgaaaa acattgcata taactacata gtgagactcg catgattata ttagtttttt 45420
cggcacctgt tgcagaaatg gctgatgctt gtacatgtga atttggatat agcgaaaatg 45480
tcgagataat ttacaggtcg ctcgaagcga gcgctgagtt tgactgcatt gtcagtgcta 45540
cgaacagttt ggtcaggtgg atgggagcgc gaatgctgaa tatatcgggc aaggttttta 45600
ccaatagttt gtgaggcttt tggttggcgt gcatcacgtc cgagacatca ggggacaatt 45660
ctaatgcgca ttcttttaaa tctgtatcgt taaaggagtt gacgaaatga ctttcaaaat 45720
gactgataaa gcgagaactc tcaaagtgta caatctgctg gaggggacaa atgaatatat 45780
cggagttgga gatgcctata tcccaccgtt tactgggtta ccggccaact gcactgagat 45840
tgaaccaccg acgactacgg aagggtttgc cgcagttttt gacttcacaa agcaagagtg 45900
gagccttgaa gaagatcatc gtggcaaaac gctttacagc acagaaaccg gtgaaccggt 45960
gttcatcgct gaacttggcc cgttgcccga aaatgtaacc tacatctctc caaacgggga 46020
ataccagaaa tgggatggtt ctgcttgggt taaagacgaa gaagcagaga agactgccct 46080
tgtcggtgaa gccgagcaga ataaatcggt gctgatgaag aacgtcagcc aacaaatttc 46140
cttgcttcaa gatgcgattg atctggatat ggcaactgat gaagaaaagg aaacactggt 46200
tgcgttgaaa aagtaccgtg tcttgcttaa ccgagttgat acttcgttgg ctccagatat 46260
tgactggccg atattgggaa acgaggaaga agattcggca aatttgatta aataaagtag 46320
gtaggtagtt atttatataa tgtgatataa atatgccatc ccgatttgac tattcatcag 46380
ggtgtcaacg acggatgaaa agtgatccac ttatatctcc accaacggcc caatattgat 46440
ccaccgtttt actcaggatt agcttctgct ataaccccgg cctttcgttt ctgtctgagt 46500
cgatagcttt ctcctttgat ttgaacgaca tgtgagtggt gtaagatacg gtccagcatc 46560
gctgaggtca gtgctgcatc accggcgaac gtttgatccc actgcccgaa cggcagattg 46620
gatgtcagga tcattgcgct cttttcgtaa cgtttagcga tgacctggaa gaacagcttt 46680

-continued

```
gcttcttcct gactgaacgg cagatagcct atttcatcaa tgatgagcag gcggggggcc  46740
attactccac gctgaagcgt cgttttataa cggccctgac gttgtgccgt agataactga  46800
agtaacagat ctgctgctgt tgtgaagcga actttgatac ctgcacggac tgcttcatag  46860
cccatcgcta ttgccagatg ggttttcccc acacctgatg gccccagtaa tacgatattt  46920
tcattacgtt ctatgaagct gagtgagcgt aacgactgga gttgcttctg cggtgctccg  46980
gtggcgaatg tgaagtcata ctcttcgaac gttttcaccg ccgggaaggc tgccattcgg  47040
gtatacatcg cctgtttacg ttgatgacgt gccagttttt cttcatgaag cagatgctcc  47100
aggaagtcca tataactcca ttcctggtct actgcctgtt gtgacagcgc aggcgctgcg  47160
cttataaggc tttccagttg caactgcccg gcgagcgcca tcagtcgttg atgttgcagt  47220
tccatcatca cgccactcct ctgcagaatg agtcgtagat ggagagtgga tgatgcaggg  47280
ggtgtttgtc gaagttcacc agattttcat caagatgcac gtcatactct tttttctccg  47340
gaggcagtgc cagcatggac tgctgctctt cgagccagcg atcgcaggga cgggcctgga  47400
ttgtttcatg ctttcgttgg ttagcgacat cgtgcagcca gcgcagaccg tggcggttgg  47460
ctgtttcaac atcgacagtg atccccatcg ggcgcaggcg agtcattagt gggatgtaaa  47520
aactgttacg ggtgtactgc accatccgtt ccaccttacc tttagtctgt gccctgaagg  47580
ggcgacacag tcggggagag aagcccatct ccttgccgaa ctgccacagc gaaggatgga  47640
accggtgctg accggtctga tatgcgtcac gttgcagaac cacagttttc atattgtcat  47700
acaacacttc gcgcggcaca ccaccaaaga agcggaacgc attacgatgg caggtctcca  47760
gcgtgtcata acgcatattg tcagtgaatt cgatgtacag cattcggctg tatccgagaa  47820
cagcaacgaa cacgtgaagc ggtgagcgac cattacgcat agtgccccag tcaacctgca  47880
tctgtcgtcc gggttcagtt tcgaaccgaa cggcaggctc ctgctcctga ggaaccgaga  47940
gagaacgaat gaatgccctg agaatggtca ttccgccacg atatccctgg tctctgatct  48000
cgcgagcgat taccgttgcc gggattttgt aaggatgagc atcggcgatg cgttgacgaa  48060
tataatcccg gtattcatcc aggagtgaag caacagcagg tcgcggcgta tattttggcg  48120
gctcagattt tgcctgcaaa taacgtttaa cggtattgcg ggagatcccc agttctctgg  48180
caatcgcccg gctactcatt ccctgcttgt gcaggatttt aatttccata actgtctcaa  48240
aagtgaccat aaactctcct gaatcaggag agcagactac cccctggatc tgatttcagg  48300
cgttgggtgt ggatcactat tgcaccgttc gttacagcaa cgagtgattc gacagcagta  48360
acggccgcgt tcccggtcag ttcgcgcgcc gccagcttct ccagcagctc tactaccttc  48420
tggtcgctgg gtacggacgt atcgagtggc tcggccactt tgtacttctt cacaccgaat  48480
cgaatgaatg ggttgagcat tagcgagacc atgctctgct caaattcatc aaggttggcc  48540
agcgcctctt tcttggcgtt ggttcccatc gtttttatgg catccagctt gtgctttagg  48600
gcgatcagtt tttccattag tgtttaacct ccatcggtcg ctcgggagtt ttcatgtgtt  48660
ttctttggtt gcttcttcaa tgagtgccgc gtacacgtca gtgacgggcg ccagtgaatc  48720
ggtggacgtg gttttgggtt tggctggttc tgttttcttc gtgcgtttaa ccagactgtt  48780
aatcgtcatg gtgttgcgct tccgggtgag cattctggca tggtcgtttt gctcttccac  48840
ttctttgata agcgcagtca tatcgatgaa gtagagctgt tcgcctttgc ggatctcttc  48900
gaccatcatc ttcagcgcct ggcatttgcc agcagcaatg gccgcagcgc aggacaggaa  48960
cgatgtagct gggagacgct tctctttgta ggcgaggatg gtgtgctggc agactgtata  49020
gctgcaatgg gcctcatggc cgttgatctt cacttccgga cagcacagcg aataaccgtt  49080
```

-continued

```
gtttccggag atagacggga ttttcgacaa atctgttctt gtggacatgc ttctaaccgt  49140
agtcgtgtac ttacttattg agcgcagttt aaaaaagccc caccaggggg ctaaatggtt  49200
tatcgaggct taccaggtcg cccagccagt cattttgtcc tgggcggctt cgaaccggta  49260
tggctccagt aaatcgttgg catggtggac ggcgtaggat tttgcctcct gtttaatcat  49320
cggcagctcg ttggccaggc gtgccacttg ccctgcaaaa ccggctagca caccgtcaca  49380
tgcctgaccc gcatcgacaa tgatacgcac caggtctaag tcgctgcggc acatatcgca  49440
gatgatgccg tattccacct cacgaatgcg ctcaacggct tttttggtgt cgccactgac  49500
caccaattcc agcaaaccag gtggggttgt cagatctgta acgcgctcgg taacttcagg  49560
cagttcgaca atgctcagga acgccgcgat tgacgggtca tcctctacac cagccctgcc  49620
tttgatcgcg cgaagagtcg cgtcgacaat atcctcaaac cgttcacctt catcgcacac  49680
cgcctgattg gtgtagacaa cgcggccgtc gtaccatgct ccagcacgta cttctaccgt  49740
tgcatccttc atctcgcgag tgaacgtcac aagtgccgcg cgtttctgtt taacaccagg  49800
cagctccgga gactctccaa aacgaaccca gacccgcatg tatttcgacc cttccgaaag  49860
aggtgcggtg ctcacagacg tggcgatgtg tttcagcgca gtctggatcg cctcaccgat  49920
aatcttctgg cgctcttctg tatcaatttc tacgcctgat ttgtcgatga tttcggtaac  49980
ggacttctga atatctgctt tcataaaggt tcctcaattc cttcgtcgcg catattctta  50040
cagaaaatta agtaagtatc tacttatcga tttaggttca ggaaaatcca tagtccattg  50100
cattacaagt tcaaatattg accaaccctg attcgacaag tgctacctta tcggtttata  50160
tgctatgggg cattgttacg cgtaaatgag tagcctgagc catgtctttt tctataaact  50220
ccatgataga aaccatctta ccttgctgga ttatgtatgc ctgagaaaat ctttaaagcg  50280
ccttgcccta catgtagagg gacatgcaat acgttagttc atggtgaaat acaaaaagag  50340
tggagtaatg cggtagacag ttttaattta tcatatgggc aagatagtca taagcttctg  50400
gaatgttgcg ggtgtggcac tgttttttac tataaggact catggggtag tgagcatggt  50460
gataatgata tttacggaaa attcacccct acacatttta ttgaaacagt ccctgcgcca  50520
gagcaaccaa aactaaagcc agactggttg tttgaaattt acaaaaaaga tcaaatccta  50580
ttttttattc ttgatgaagt atatacagca tatgaacacg gatcgttcat actcgcctct  50640
acagggctac gcacggcatt tgatcactca tgcgctcata ttggcatacc taatgcctac  50700
acaatggaac aaaaagtcaa agatgttttt gtgaaaggtt atgtgagcga aaccgaacga  50760
gatcaactca gaattgttat agaagctggt aacgctgccg cacatagggg atggagacct  50820
gacaaatctg cttttgagtc actattacat gttgctgaaa aattcattca gcaagttata  50880
ctaagagacc ttgagataga aaaaatcggc gaaaagatac caaagaagca aaagaaaaaa  50940
ggagactgta aacaatattg tgtaattgcc tgtttttgat atcttcactc caacaacgga  51000
gacaggcaaa ttatggacga aaagaaactt aaagcacttg cggctgaact ggctaaaggt  51060
cttaaaaccg aagccgacct taatgcattt tctcgtatgc taacaaagct taccgtcgaa  51120
acagcgttaa atgcagagct taccgaacac ctcgggcacg agaaaaatac ccctaaatca  51180
ggctcgaata cccgcaacgg ctattcgtcc aaaacactgc tatgcgacga cggcgaaatc  51240
gagctgaata cgccacgcga ccgcgaaaac acctttgaac cgcagctgat aaagaaaaat  51300
cagacgcgta tcacacagat ggacagccag attttgtccc tgtacgccaa aggcatgacc  51360
acccgcgaaa tcgtcgccac cttcaaagag atgtatgacg ccgatgtgtc tcccacgctg  51420
```

-continued

```
atatctaaag tcaccgatgc cgtaaaagag caggttgctg aatggcaaaa ccgccaactg  51480
gatgctctgt atcccattgt ttatatggac tgcattgtcg taaaagtccg ccagaacggt  51540
agcgtgataa acaaagcagt gttcctagcg ctgggcatca acactgaagg tcagaaagag  51600
ctgctgggca tgtggctggc agaaaatgaa ggtgcgaagt tctggctaag tgtgctgaca  51660
gagctgaaaa atcgcggtct tcaggacatt ctgattgcct gcgtggatgg cctgaagggg  51720
ttcccggatg cgataaacag tgtttatccg cagactcaca tccagctgtg catcatccat  51780
atggtacgca acagcctgaa atatgtgtca tggaaggact ataaagccgt caccagcggt  51840
ttgaaaatgg tgtatcaggc tccgacagaa gaggcggcgc tgatggcgct ggataagttt  51900
gcggaggcct gggacgacaa atacccgcaa attagcaaaa gttggcgtac gcactgggaa  51960
aatctcaata cattcttcgg ctatccgccc gatatccgca aggctatcta caccacgaat  52020
gccatcgaat cggtgaacag cgtgatccgt gcagccatta aaaagcgcaa agtgttcccg  52080
acagacgact cagtgcggaa ggttgtttat ttggcgatca aggatgcatc aaaaaaatgg  52140
agtatgccga tccagaactg gcggttagcg atgagccgtt ttattatcga gttcggtgac  52200
cgcctgagcg atcaccttta atacggtggc agttacacag aattatggac aggctctgtt  52260
ttttgccaca cgtaaacgtg aaattgaaaa ctatctttgc ccagatctaa taagagatga  52320
gacaggggtt caggtttttt tcacagacac atgcgacgca aaaaaaccat aggaagggca  52380
accagcacga aacctaacga cgtactggac aggttctggc ccttaatgac tgccgaaaaa  52440
atcataaaat gctctactta tagagatgat aataatgaca aaattgagct tatagacatt  52500
cttgaaggca ttgtttcatt agtcgattga tcgtgaccta cgttgcatag cggtgtgtca  52560
gttaagcctc tgtgtaacgt tattgtgctc aaaaaatgag cttaacgaat ggaagggact  52620
tcccctgatt atgaacctga ttaactcttg tgcaatcatg ggataaatat cactccggag  52680
ggattcgtta tgaccatcac tactgtcggt atcgatcttg ctaaaaacgt gttcgctgtt  52740
cactgcgttg atcagaatgg taaaacggtt ctggttaagc ccaaagtatc gcgtgctgca  52800
cttcctgagc tgattgcagg tttacctccc tgtgttatcg ggatggaggc atgctccggg  52860
gcgcactact gggcgaggct gtttcgagag tatggtcatg aaccgcgcct gatggctgca  52920
aagtttgtat cgccttacca catggccggt aaatcaggaa agaatgatgc tgccgatgct  52980
caggctatct gtgaggctgt ccgtcgtccg catatgcggt ttgtgccagt gaaggacgaa  53040
agccagcagg ctatgcagtg tttacatcgt acccgacagg gttttatcga agagaaaaca  53100
gcaacgtata atcgcctgag aggattgatc tctgaatttg gcgtcatcgc cccgcagagt  53160
actgatgcct tacgccgcat ggtttctgag cagaagaatt ctttaccgtt ccaggttcag  53220
caatgtattg atgatttgct ggagcacgtt gatcgcattg aagccaacat tgctgactat  53280
gaccgaattt tgtcccgcat ggccaaaaca gatcaccgca gtcagcgact gatggagctg  53340
aagggagttg gccccacaac ggcctgtgcg ctggtcgcca gtatcggtaa tgcacatgat  53400
tttaagaatg ggcgtcaact ggccgcctgg ctggggctca cgccttcaca gtacagcagc  53460
ggcggaaaat caaagcttgg caggataacg aaagctggcg attcgtatct gcgaacactg  53520
ctggttcagg gggcccgttc agttctgatt ggcgctgata aaaggactga ttctttcagt  53580
cgttgggttt gtacgctggt tgaacgcaga ggatactggc gtgctgttgt tgccatcgcc  53640
gccaaaaacg caaggctgtg ctgggcatca ttgcattacg gtgatgattt ccggctgtac  53700
tcagccagct aaagcactaa gtagtataac catctgacct gcaactcgtt gatgataaag  53760
ggttagaccc cgtgaggcct atctggctat tgtacaggat atacgtatcc gcttaacgaa  53820
```

-continued

```
caagaacctc acgcgcgtct ttcatcaggg cccgaatcga tgacgattca tcatggccgt  53880
ttatagtacc gcagtctctc ccctttattt ttactgaaga gcagacagaa accttgaata  53940
ccgacgttga catgccgggg aagcccttat agtacaataa ttttcgatat ccaaactgac  54000
cccaacttca agtttgcctt tctgttcacc gagttgaatt cctttctcga tgcccttctc  54060
gatacctttc tgttcaagct gttgtgcgat ggtcatgagt gcgtctccat gctgcggcac  54120
acgctgtgcc agttcgcgaa caaaggcttc ggagtcagca gactcgccgg cctgtaataa  54180
atagtgtatc agcgccatta cctgcggtga agacagataa tctgccatca gcaacgtagc  54240
cagtctgtcc gtcagggtgg ctatatcacg ttaagaaggt ttgctctgcc gccagcggca  54300
ggcctatagg gtcaccacca aagcacgcca gagtgctgaa gtatcgccta acctattgaa  54360
tcagaatttt aatccactgg gaattaacca ggtgtgggtg agcgatatca cctatcgtgt  54420
gcccggagtt cagggcgagc atggacgctc aaatgaacca cgagtctgtc tggaatattg  54480
aaccggtaac tcacgatgag aaacccaaca atcctaccgg gtgtgacggt ggagaacctg  54540
agcggcagtg acctgcggca tgcccgcagg gtgatgtaac ccgctgacaa cggggattga  54600
ggcgagatca ctaagccgag atgatcctca aggttaagtg ctgaaaggct gaagaacatg  54660
aacccgttaa tccgcctctg tgggttgaaa atgtcaccac ggcctatgtg atctgacagg  54720
ccgtgcagaa ggcaccgaca ttgatagata tgcagtgttg gtcgaaagtg ttttgacatg  54780
taagcagaac accgggacag caacgtctat cacgctcgcg ttgctgactt ctgccaactt  54840
gcggcaagca aggacaaaga gtgcgacggg cagcctcctc agtatgtctg agtccaggca  54900
ggtgaaccgg ggaaggtcag cgacggatgt taagggggca tggctccgat gacgcgctgg  54960
ctggcggagc ttccatagta gtccgcgatg ggaaagccc attacatggc gaagggaagc  55020
agtttaaatg tgtttgcgac gtgaattaac tgacctaatg aggtgaagac ctttgataat  55080
cagcgaaatg caacgcaagc ttgccacatg ggcagccacc gacccgcccc gacgggttga  55140
acggctgctg cgtctgataa cacaaccaga atggctggct gaagcggcgc ggatcacact  55200
tgcatcaaag ggggcgcata cccccggcgt tgatggtgtg aacaaaaacaa cgctacaggc  55260
cagactggct gctgagctac aaatactcag ggatgaactt ctctctggtt gttaccaacc  55320
tctgccagcc agacgggttt atatccccaa aagcaacggc aaacagcgac cgctgggtat  55380
ccccacgctg cgggatcgta ttgttcagcg ggccatgctg atggcgatgg agcctatatg  55440
ggagagtgat tttcatactc tgtcatatgg cttccggcct gaacgcagcg tccatcatgc  55500
gatcagctca ccgattgtgg ggaaacacga gggcgctggg taattgaagg cgacctgtcg  55560
tttaacttga ccagaacagt ccagtatggt cgttattaga aagtccactt cgctaagaag  55620
acttggggcg catggcacat gcgtaaaata tctcggacgc tacctaaaac gaccaccgat  55680
gtcggcgtca aaactgcgac gaaacagaga tgataaccat catgattatt agcatgatgg  55740
tttatgtgat ttatgactga ttattactta ctagtgtatt ctagtcatca atttgggctt  55800
aattttggaa atgcatgtgg gctagaatat ttccacaatg gttcccagta agatttcatt  55860
aattcattaa ctgcatcttt tccttcgact aaatagtcaa actctgacag ataaccggga  55920
taaagattat ctgatccaac aacgtacaac tcatcgtcaa taatcattaa tttggcgtga  55980
ttaccaggtg caacagggac tttaggatag aaaagtccac tacctttaat tgctgacatt  56040
agtgcactac caataatacc ttgatgcggg ggtttttccg aaagtggttt ttgcttaagt  56100
gttgcagtat aagcgctttg ttctaaatca ggccacttgt aggtttcgcc ttcaattgta  56160
```

-continued

```
ttttcatcag gtactttatc tgtaaagaag aatggtgcaa tcaatattct ttttaaggca  56220
tcagcacggc taccatcagg atcgtctaat acttcatcgg tatcaatatc atgggttagg  56280
taatacttaa ataattcata ggtccgttct gctccagaac caaatgagta ctgatcacca  56340
gcagctccag ctgctgcatc tagagcagag actacaacat gaatatgaag atctttattt  56400
tctaacaaag cctcaataat ccaattacac gtaaagtggt ctttccattt tttttccaa  56460
gcactcacga gatcttgctg tgaaattcta attatgcgct tagcattttt tatcagttgc  56520
tctttcatta tttcagaccc tctttggtag tcatgctcca tattaggtcc tgtccaatat  56580
ttacctactg ataaaactct gtctgctttt ttatactctt ccatgttttc gtattcacta  56640
atacgagtcg ctaccttctg attaaagttt tcatgcaagt tgagtaggtc ctcttgccgt  56700
tgcttcatat aattcatagc aactgagctt ttaagcggat cttcaggctt atcatagaac  56760
tttgttccga ccgcccacat catgctttca taatcaaaat attctttttt tagtaaatct  56820
gaattacatg accatagttc gttaagatat agctgggagc cataagcaga agaaccatga  56880
gtgataattg atacatcatg aacaggtgga taatttctaa atagatccat gttcatgtta  56940
tgtccaccaa caagagcttc agtaccatct gaggccatta tttttgtgtg attccatgtc  57000
attcttgtat cgttgattgg tgggaaatca ggatacacgt ttctcataaa tgatgtagcc  57060
aacccttctt ctattctaaa gaaacggcct agccaaattt caggcatttt ttcccaatat  57120
tgtcctcgct ccttaattag ctgaattaac tctgatttaa aagcaacaaa gtcaggggag  57180
ccatttgttg cagcagataa cccattcata aatactgttg gagattggcc gaaaagaaac  57240
ctatactgag ttggctgagt tcgccccatt tttttcgata aggattcatc aatggcctta  57300
aaaatcactt ttcgccactc tgcatcgggg ctattaagtg atgatatatc acagcgataa  57360
cgcgaattcc gcagtacttc agtcattgcc cctgcaaact cctcttgccg taagtaagat  57420
tgctgcatga tttctttacc aaatggggct ccccaagcat gggggtatc cagaagtcgt  57480
atataattaa tgttacttag atgatgaaag tagtttccaa tattattaat gacattatct  57540
atttgaagca tattttatcc tttgtttatc gatgtgttaa taaatatcgc cgttgcagca  57600
attaatagcg gggagatagc ggggtacttt acgcccatag tcggttaaac tcaacctgat  57660
attttcccgc tatttcaggc gcaccacgta tgacgagaac attttctgca ttgtgagtat  57720
cgccattggt ggtgtaattc attgaccctg tttgtatcgt gtcaccatca gctatcatca  57780
ccttgttatg atgaattgaa tagttgttat ttaaccttac cggaacatgt tgttgtgcca  57840
gatagtgaat ggctgaatag ttcagacggt tagctttggc atcagcaaca actcggacgt  57900
taacccctcg cttttgagcc gagacaatgg ctgtcgagat ctgcttactt gtaaaagtat  57960
aggcttcaac atcgagcgag gattgagcat tattgaccac gcttaataca ttctctaatg  58020
cagtgtgaga aggagagaat ccaacattaa aggacggggt tgcgagcgcc gaagcgctga  58080
ccagtacaaa aatgatgact gagagtttaa atctcatgag ttatgtccaa agtttgtagt  58140
tcatccatta tgtaaaaccg aaaaaaaacg cctatgtttg gcttgctgta tcgagctttg  58200
gcttttatgc ttcgctcggt ttccattgtg gcgatccgtc ggccgttcgg taaggtaatc  58260
agcccatcag gacggtgctt gaccttaaac tgatttaaaa agtattacgg tcacttttaa  58320
tctaattttt agccccttct tgggcgaata tcaagtgaaa acgctgttgc gataaggtct  58380
gctaaaaaac aggcttaccg tacatttttt gaatattaaa cataatgtag gctgcatcac  58440
catataagtc cacatacata gtaatggtat gcgatgccta cattttgtga ctaactttgc  58500
ataatcatat aagttttata taaaagggtt tgaggttcag tagaacggtt ttacatctta  58560
```

-continued atattttgta tgataaatca tagtgttata gataacaaaa aacaggtgca taggggcgtt 58620
tttttagggg tctgaagcta agtcaaacga aaactcacgt taggcgagaa aggtcgtctg 58680
aaaaatcgat taatggacag cgatgtccgt taaatgctat ttaccgatta aaaagacacc 58740
gttttaggcg catttttcac tgtctataat gttttgattt atcggacaaa aagcccttaa 58800
cgtgtgaaac cgttccgttg agcgtcaaac ccctattaac gtggaggacg tatcaatgtc 58860
gcgtcgtggt ttacgtttat cacagctgcc accggtacgt tcggaaaagc caaaaccggc 58920
caaaacgtcc gcgcagctca tggcggaaga tacgctgcgt gagttaattg ccgcccgctt 58980
tgccgtggga aaaccggtta tccacattca tgcaaactgg aatgatgcgc tactactgcg 59040
ggtattgaaa gaagcgatac accaagctaa aggcccgccg tttgtggtgg taccaccgca 59100
tctaaatgaa catgagaaag agaacgacta gcgagcgcta gtcgtttaaa tgattagtgg 59160
cggatttgcg ccaaatcgtc ttcagaaagg ccggttgctt cttggaccga ctcaatcggc 59220
atgcccattt ttaacaaact gcgtgccact tcgagtttgc ctttctctat gccacgttgt 59280
tcaccgagtt gaattccttc agtacggcct tccatacgac ctttttctat gcccttctgt 59340
tcaagctgtt gtgcgatggt cataagtgcg tctccgtgtt gcggcacacg ctgtgccagt 59400
tcgcgaacaa aggcttccga gtcggctgac tcgcctgcct gtaataaata gtgtatcagc 59460
gccatcacct gcggtgaaga gagataatct gccatcagca acgtcgccag tctgtccgtc 59520
agggtagcaa tatcacgttg atgaatatgc ttttgcagca gcgtcagtgc cgccatgctg 59580
cggtgctcca taatatcatc gtctggaata accgtcacat caaccagtgg aaatgcaccg 59640
ctatagagtt tatgtgccaa ctcagggtcg tcaaactcat ctaaccaccg cgtggagtac 59700
ggataaggac tgcgtttacc cacgtaaaag agcaccggta tcaccagcgg cagcttagca 59760
tggcccgctt caaggtggcg ttgcatggca gcgatcgcgt aacgaattaa gcgaaaagcc 59820
atatgcttat cgggtgagct ttgatgctcg atcaacacat ggacgtagcc ctcgccttcc 59880
acggtatcga ggctgtaaag cacatcgctg aagtactgac gcaaatcatc ttcaacaaag 59940
gagcctgact ccagctttag cgtgctgagg tcgcagatag cgcgtagctc agcgggtaga 60000
tgcaactcca taaagtcacg tgcaatctcg ggctgggtga gaaactgcct aaatgtggca 60060
tcatggggtg tgggggtact gtttttcttc ttcatcagct cagactctga aaaatgatga 60120
gtgaatgcta tcacaatcaa agcaatacaa gatgttaagt ttacccctca gcttgctggc 60180
agacgcggat caccgtcatt ttggataccc ctgcgagacg ggctgtttca cgcaatgact 60240
taccatgcaa taggcgtagc gttcggatga gctcgtgttt ttgtgcatca gccaccctgc 60300
cccgatattt accttccgct ttcgctttgc tgatcccttc cgcctgacgg cgacgtcgat 60360
cctcataatc ttttctggat atagccgcga gcatatccag catcatgcca ttaacagctt 60420
tgagcatgct gcgagtgaat tcatcgctaa cggcgttatt gagcgccaaa tgactggttg 60480
gtaaatcaag actcacgata gacagctgct tatccgttat ctgctttctt agcgcttccc 60540
atcctacgtc gtccaatcga gaaagcctat ccacttgctc aatgagaata atatccccag 60600
gctcagcctc ttccaaaagt tgcacgagtt ttggacgtgt catcgttgcg ccagagatat 60660
tgtcgacata ccagcctgca attcggtggc catgtaggcg agcaaaattc ttcagtgcat 60720
tttttgcgcg agtggcatct tgttcagagg ttgatgctcg cagataacca aaaatgagca 60780
ttttttagcc ttgaggtaac gtttaagtag tcattttgtt aatggtatca cttatgtggt 60840
cacattgata tggaatacca tgttttaatg cggtatctca gaagtatacc cgaatgtgac 60900

-continued

```
aggctgacgc gcccgtaggg cttatccaac ccttcgcctc agatgcaagc tctgaacaga  60960
ctcacggttt tcgtttctgg tcaaattcta attaggcgtt taaagagaag gttttgtata  61020
tcctgcctgt gggatagtat tgcgtgtgct gttattacat tatcctccac tgagtacaat  61080
actctgtagc cgtcaggggt gttgcactca cgatatttag cacaacctat cttgagtaac  61140
tccgggcaga cctgacaccc aagtggaaaa tcactgactc gtttttcgaa gtgctcaatg  61200
atgccgctga tcacttcctt tggttctgac tcgatatgac gtaagtggct cgcaatatca  61260
tcaatgcagg ttttgacagt tctggtgtac tgaataacaa tcgccattac agacccgcca  61320
gtagttgttc tttactgaaa atattgccgt ctgccttatc ttgctctgaa agcgtcagca  61380
acttcagtag tgcaatcgcg ttctgtcgct cctgttgcgc gtcgtatgac tcaataacat  61440
atgccggaac cccattttga gtaacaagaa ttggttcttc cagatcgagt gacgctgcgt  61500
tttttttcac atagctaatg gtttcaattt tcataacaac ctcacataac aaagaggttt  61560
aaatatagtc tatatttggt cttgttgcaa caatttctgg acagaatgac ctgaatgtcc  61620
tagctgtgta gtgattactt gttaccacca taccctccac cccctcgcct gctcagaaac  61680
gatgtctaac tgcgcggttt gatgtgaatg atggttggat acgtacaata atttaatgac  61740
aatacaaaat atgttgtaca ttttttgtgt gtatgtacaa tgtgattgaa ctttataggc  61800
aatatatggg cagggaatct atctcagggg aaactatgaa acgagattac ggtagtgtcg  61860
gtaccatagc gctcagagca agtgctctac ttcaggcaat gagtcgggat attgaggaac  61920
aaagaaaaga attcaatctg acagaatatc atcaaacata tactcgtaat gcggtcgcaa  61980
aattgcctaa gctgagccga cgcatcgtag agctggccgt taaagaaatg gaagaaagcg  62040
gctatgaatt taataaaaag caggttggca acgtcgagca atatgcacta acaattcaga  62100
acgttattga tatatatgct caccgacaga tacctaagta ccgtgatatt cataaagcac  62160
cttacgtaat ttttgtcgtc aacctaaaag gtggggtatc aaaaacagtc agtacagtaa  62220
cgctggcaca tgcattacgt gtacatcagg atttgcttcg ccatgatctt cgtattttgg  62280
ttatagacct cgacccgcag gcatccagca ccatgtttct ggatcacacc cacagcatcg  62340
gcacagtcct tgaaaccgcc gctcaggcaa tgctgaatga tctggatgct gaaacgttgc  62400
gagaagcggt tatacggccg actattattc caggtgttga tgttatacct gcttctattg  62460
atgatggttt cgtggcgagc cagtgggagt ctctggtagc agaacattta cctggtctta  62520
aaccttctga agttctcaga aaaacaatca ttgaccgtat cgctggtgat tatgattttg  62580
tctttattga tactggccct catcttgatc cattccttct gaatggctta gctgcgagtg  62640
atttgctttt gacccctacc cctccggcac aggttgattt ccattcaacc cttaagtatc  62700
tgactcgttt gccagaaatg cttgagcgtc ttgaagaaga aggtgtagag ccacgcctga  62760
gtgcaagtat tggatttatg tcaaaaatga ccagtaagcg cgatcacgaa acgtcccata  62820
gtctggctcg tgaggtgtat gcgagtaaca tcctagactc atcgctcccg aggttggacg  62880
gattcgaacg atgtggtgag tcttttgaca ccatcattag tgctaaccct gtttcgtacc  62940
cgggaagtgc agaggcattg aaaaaggcac gtactgaagc tgaacggttt actaaggccg  63000
tatttgaccg aattgaatat atcaggggag cgtcaaaatg aaacaggtta tagctcgtgg  63060
tcgggttctg ggaaatagta attcagagtt cgctagaatg ctcgaaggcg acggtgatgt  63120
taaaacattt acccttaaat caggcgtgca ggctaggttt gtcaaaacag ttgtgttaag  63180
cggagaagtt gaatcaaaaa cgttcgttga tgcttcggtt aatggacgtg atcagacaat  63240
gcttacgcgc gagtccgtca gtgatatttc ccggacgata aagctgcagc agttctttcc  63300
```

-continued

```
ggctattggt cgggaggtta atggactaat tgagatatta gatggaaccc gacgtcgtgc  63360
tgcctgcatc tttaataacg ttaaattcga aattctggta acaaaagatg atatctcact  63420
cgccgatgca cggcagttgg cgaaagatat ccagactgcc agagaacata gtcttcgcga  63480
gctggggaag cgactcgaag ttacctacgg aaccagcatg acgaaagaag atattgcgtt  63540
gaaagaaaat ctctctccgg cgaaagtgac acgtgcgttt caggccgcag cagtgccaga  63600
cgaaatggtt gcagtgttcc cggtgataaa tgatatttcg ttgtcagatt atcagttttt  63660
actgaaactg gccgaagaag caaacaacaa gcaaacatcg gtaacagagc tgatggaaaa  63720
agttcagcat cggttgaaga ccatgccaga ttatccggca attgataaaa gcaaaattct  63780
tgcggttatc cggtcggaga gcaaattgct gacagccctc ccaactagaa cggttcaaac  63840
agagaagctg agagaatttt cagatcgtaa tcagtttgcc agaaagaaaa ctgatccaaa  63900
gaagcgactt gttgtttatg agttttcccg tatttccgct gaggcacagt cggagattga  63960
taaggcaata aaacgtattc tggaaagact tccagaatca ggtgagtaag ggataaggat  64020
gccgaagagc atcctttttt gtatgttttt caccacgcca atttcatggt tatttgtttg  64080
attataaagg aaaattgaaa attctttcac actgaaatca ccacgctttt caacctcttc  64140
gtgactcata atttcgctat tggcagttca gaccagcgag ttgtataggc aggcgaaagc  64200
atctcccgtt ttatatgcca ttcagacgct accccttcca gcaaaccaca cttttcccag  64260
acatgaatat ccatgtatct catctgttcc aacttatgta atttactttc tccatttaca  64320
ctgcgttgcc atgcactcgc tttcaggaaa tcagtataat agcccctaaa tcatcttctc  64380
ggagtgaatg gacatggcta ttgcaggttg cgatttacca acttttgcca cccggctcaa  64440
tgaagtgctt actctcagtg tgccagtgcg tacacctgaa aagctttttg ggcgggataa  64500
gcagttggag acgatacaac tggcacttca ttcaccgggc cgacatgtgt tcatttatgg  64560
cgatcgcgga gtaggtaaaa cctccctcgc ccacacagcc gcttcgctta tccagtcttc  64620
ggataaccgt cctattaccg tcagttgtga ccatgactcg accctggaaa cagtcatcga  64680
atcggttatt agccaaggaa tgatgcgcat gccggtagac cggtacaaaa cgtctgcaac  64740
ttttggtctc aatattcctg ttttaaaagc cgaagcccgt gttgaagagc gtgaaacttc  64800
tcgcgttcgt tcagtcgtta atatggccag tgctgttgaa gccctgaact atctgacgga  64860
acgctattcg gataacacgg ttattgttat tgatgaattt gacctgatcc gtagcgagga  64920
gcagcgtgcc cgctttggtg ttttgctcaa gcagttaagc gatggggatg tacccgttcg  64980
tatcatcttc accgggattg ggcagtcggt atctgatttg attggcggac atctgtccag  65040
tcagagacag attgagcagg ttgatcttga acgtctgcac tggacaggtc gtcagcgtat  65100
cgttgaaagt gcatttagat attttgatat taatatccct gatgatatcg cagaccgtat  65160
atgcgcgttg agtgatggat ttccctacta tgtccatctc atgtgcagca agctccttca  65220
tgagtgttac atggcagatg aagtcgttag cacagttaca cgtgatctat ttctagcttc  65280
gctcgatgca gctgtattgt ctgctgagga aacgctcaga tcatgttatg aggcagctac  65340
ctgccgagat gagcatatgc atcacattct ttgggcgatg gctgaaggtg cagacctcaa  65400
cagaatgaaa gaccacatca ttacctccta tatccaggtg atgaagtacc tcgacattga  65460
acctctgacg cagaaaaact tcgacagtcg ttttgctcgg cttcgtaaag agaatcacgg  65520
atctattctg tgccatgcgc ttgtcgggaa ggatggtgtc cggccaggat ggtttcggtt  65580
cagggaaaac atgatcagag gctttgtcag aatgcaggca gagaagtgcg gaatagttct  65640
```

-continued

```
ggattttgat cggcagtata gcgcccatac agcaagtacc agaacagctg cagttagagg  65700
ggtatacaat cccctcagca cggtggaacg cagcgtagct cgcctcagac gtgatgatga  65760
aaaggaagct gaagaaaacg aataacgtat ttgtaaatga atggaatacc cgcgaattat  65820
atatgcaata ctcgggtatt cagcgtttgc atcatgtcga gttacccgta cagcggagtc  65880
ttgctcttct cctgtctctt gatcaggcaa ttactcaatt ttcgaggcta acatcttaat  65940
gctgttttag tgtcgggga tgctgctaac atcttcttca ggctgtgggg cacgaccagg  66000
cgcattgaac gtgatagtga tgatctttct ggccagcccc tcctctgaaa gggcatcatc  66060
cacactgaca tcacgaatca gtggactttc ctcttctata tgtcgggcaa tatcccgcag  66120
ccactctgcc agcatttctc tgtccatctt tctccgctcc ggttgtgtac attcagcatc  66180
aacataccac accagaaaaa gtgaagtctg cgtagtgtgg ttaaaagatg accgttttgt  66240
caggcgcgct gtcatccgtg ctggtagcga cctgcgcgga ataccctcat tttatacaca  66300
ggattgccca ccgaaattgt ggacagcaac gatgaaaata cgatgtcgct gcgctcctca  66360
ttcatatcgc tctgctgtga acgccgtgcc gctactgtag ccgggccgct gcgaatgcaa  66420
gggttcgctc tgccggtgtc ctcacccggt cgcagtttat ttcaaaggct ttacccgctg  66480
tcttcccgtc gttttccgtc tcaattttcg ccgtcaaacc gtccagccag cgtgggcttt  66540
ttcactgcgc tgcggcttgc ggcaccgccc ctgcattctc cgcttttcgc ccggctgtcg  66600
tatcggcacg gcgtaactgg cgccgcattt gagaaaggag aactaccatg tcccgattta  66660
tccagggtaa ttgcgtccat atcatgtccg gctttccgga taatgctgtc gatttcattc  66720
tcaccgaccc gccatatctc gtcggttttc gtgaccgtca ggggcgtacc atcgccggcg  66780
ataaaaccga tgaatggctg caacccgcct gccatgagat gtatcgcgtg ctgaaaaaag  66840
acgcgctgat ggtgagcttc tacggctgga accgcgtcga tcgctttatg gccgcctgga  66900
aaaatgcggg attcagcgtt gtcggccacc tggtgtttac caaaacctac acatcgaagg  66960
ccgcatatgt gggctatcgc cacgaatgcg cctacatcct tgcaaaaggc cgtccgcccc  67020
tgccgcaaaa cccgttgaat gacgtaattg cgtggaaata ttcaggcaac cggcaccacc  67080
cgaccgaaaa acccgtaacc agcctgcaac cgctgattga gtccttcaca catcccggcg  67140
cgattgtgct cgaccccttt gccggcagtg gctccacctg cgtggccgcc ctccaggctg  67200
gccgtcgtta catcggtatt gaattgcttg agcagtatca ccgggccgga cagcagcgtc  67260
tggccgccgt ccggcgcgcc atgcagtacc cggccgctaa cgacgagttc ccggaggccg  67320
cgtaatgaac tatgcaggac acgaaaaact ccgcgcagaa gtggcggaag tagccaacag  67380
catgtgtgac ctgcgggcga cgctgaacgg gatggagcac cgctatcgct ttgactctga  67440
tgtgctggtc gaacgcctga cccgtcagac cctttttcgc atcaatgccc tgtttatggc  67500
ggcatacaac gaaatgcttg agctggatgc ctgctttaag gactaaggag aaaaacatgt  67560
acggaacctg tgaaaccctc tgccgcttgt tgcgtgagca gtatcccgca gaaaccccgc  67620
tgaacctcat tgtctggtcc ccggcggata tcgaagcact ggccgacgga atggaatatg  67680
ccgtttcgga acaggacaca agggcggtac tggcgcgtat ggacgccata ccggaagaac  67740
aacagcttga gtcgggcgtg tctgccggtg cagtgatgga tctgattgaa caggtgaaag  67800
aggcagttcc ggcggtgatg gtgccggcgg atctgcttga aaccctgcta accactgccg  67860
aacaggcgtt atggcacagg gaatggaccg cccgtgacag caatcatccg gtcccggaaa  67920
gcgttacccg ccgcctggct gatgcggcga aagttcgcgc attactgaaa aaatgaaatc  67980
aacacgccgc ccgggcggcg tgtactgacc ccgttcagag gaacccatta tgcaggaaac  68040
```

-continued

```
caccacgtta aacgcccttg tgatgcgccg tgcgcgcgat ttgattgctg attatggatg  68100
gcctgaccat accgatgttg atcagcgtga tccggtcaat aaaccgggat ggataagcat  68160
ttatgtccgt ctggatgcgg caaatattgt tcatctgctt cctttacttt gtagcggtga  68220
catacccgca gagctgcaaa atgccatgac aaaaatagcc gggacgtcag cgcagattat  68280
tttatccggc agccgctatg ccgacgcgcc gcagcttccg gaggacggaa cacagatagc  68340
gttcccctgg gccggggaat ggctgacgga gccggagatt caggctgtaa cggattgcct  68400
gtcccgcgcc gtgcgggatg tatcccggca ggtatgggag gatgcgcgcc ggataaaggc  68460
ggcgctgacc acgcgcgggg aaacgctgtt ttatcgtcag acccgaaatt tccgtctggt  68520
tgtgaaggaa aatgatatgc cctgctggct ggacgatgat gacaatttgc cggtggtgct  68580
cgatgccatc ctgaacaaag gggcacgcta cagcagcgtc gagttctttg ttatcagcga  68640
caaagttgat caaatcctgg catgtggcca gatgtgcgat gtgctgcgta ttccgggcga  68700
gcctccgcgc cggtggatgg atttaaccct gttacatgag gtcatggcag aagcgcgtgc  68760
agaaatcagt cttgtccgca atgccctgtc agcaatccgg ccagtgtagc gaacagcagg  68820
gggcggcggc cccctgaatc taccacgaag gatgtcgccg gctccgcttt tacggctctt  68880
cctccacgtt gttccggctt cgcggtgagt aacgtcccga gcggtctgcg gcttacgccg  68940
tgcctctact ctagcccgaa cgctgcaaat gcaagggttc actgacgtcg atgctttcac  69000
ccggtcgccg tatgtttaaa tgcctgtcgc ggttcttccc gtcgttatct cgctcaatat  69060
tcgctcgcta accgtccaga ccctctccgc tatttaccgg cgctgcggct tcatgcatcg  69120
cccctgcatt tttcgctccc tgtcgggctg tcgtgtcggc acggcgtaag ccgtaactca  69180
gacaacatcg actatggagg attttttatg cgcactacga ccaccacacc ggctgtttat  69240
gtgggtacgt atcacaaata caactgcggc agcatttttg gcaaatggtt tgaactgacg  69300
gagtttgacg gcagggagga tttttacgag gcctgccagg cgctgcacgc cgatgaatgg  69360
gacgcagaat ttatgttcca ggaccaggaa ggtatcccgt cgcagttcgt ctctgaaagc  69420
gccattgact gggattttat cgccgcttac aaacgcgccg aagaagaggg cagggaagcc  69480
gcttttatcg cctgggcgga gtataccggc gagtgtgact atgacgcgtt tgatgatgca  69540
taccgcggcg aggcggaaag tgaggaagac tatgcgcagg agatggttga cgataacggc  69600
ctgttaaatg aggtgccgga gccgctgcgc agctacttcg attttgaggc gtatgcccgg  69660
gatttgttca gcagcggcta tgtgttccat gacggttatg tcttcggtaa ctgattttcc  69720
ccggcaggcg gtttagccgc ctgtcagccc gcgcgcaaaa ccctggcagg ctctgcctgc  69780
cggcgaagta cgccgcgcct gcggcgccgc gtatctccgc cagtgcctga tgtcccggtg  69840
gtgtcagggt atgaataccg gtttgttgca gcgggtcggt gttatttctg ttccggtgtt  69900
aatacctgcg ctgccgtagg caatagtggc cataccggtg gcgtactggc tgatatcgct  69960
gtcctgtcgg cttttcttcc cgggcgatat gactgtgggc gacttcccta gcgggaaccg  70020
gcgctgtcgt aaacggagcc ggtaaaccgt ctccgccctg tcgggcttcc atcgcactgt  70080
cgcaggttca acatcacgct tgcggcatcc gtaaacggat gcgccgctct caccagcccg  70140
gcggtaatgc tgccgggctt cttcggggca acgccgtttc gcgcccgcgc gttccgtcgt  70200
tgcagcgggt tcctgctcat tttctcctgg tcatttcacc cttttgagtc ctttcgccgg  70260
ggctgagaca agcacagccg ctgtcagctg tccagggtaa atggcacgcg gtaaaccgcg  70320
ccctggacat ccgccatcgc ccgcgctggt ttacgcccct gcggcgaacg gctctcaaac  70380
```

-continued

```
gggtgatggt ttttaaaagc aaaacaggtt cagaaggagg agcaacatga gcgaggcgct  70440
ggcggtttta cccgacgaca cctttacccg cgaacaggct gaggtcgttg cggcgcagta  70500
caccaacgtg gcaattgagg acgatcaggg ggcgcatttt cgcctggttg tccgtcagaa  70560
cggtgaaatg gtctggcgca cgtggaactt tgagccgggc ggcacgtact ggctcaaccg  70620
ttatatcgcg gactacggta tccgcaagcc gcagtaagaa agaggtgccc tgccggagcg  70680
cgaactccgc agggccagac aatcatcaat atccagtgag gtatcaacta tgtcagtaac  70740
cgatgttaaa gcaaaagccc ccaaaaaagc gagcagcaaa aaaatcacga aggcgcagga  70800
agaagctctg aaagccgccc ttgaggccgc tgtcatcgag tatgttccgc tgtccagtct  70860
cgctaaatcc ccgctgaacg tgcgcactat cccgtattcc gtggacagcg ttcgcggtct  70920
ggctgactcc atcgaggcgc tcggactgct gcagaacctg attgttcaca ccctcgcgga  70980
cggacaatcc ggcgtggccg caggtggtcg ccgactgact gccctgaatc tgctggcgca  71040
ggaagatcgt cttgcggctg atcataccgt catggtgaag cgagtctcag acgacattgc  71100
ggccctcgcc tcggttgccg agaacgagca gcgcgccgcc atgcatcccg ccgagcaaat  71160
cgcaggtttc cgtacgctgg cagagcaggg caaaactccc gcacagattg gcgacgccct  71220
cggcttcggc tcccgccacg tgcagcgcat gctgaagctg gcaaacctcg ccccgtccct  71280
gatggagaag ctcgcgcagg acgaactgac cgttgagcag tgtcaggcgc tctgtctcga  71340
ggacgatcct gcccgtcagg tcgaggtatt cgaaaacgtg aaggccagct ggtcgaacgc  71400
gcccgcacac ctgattaaac gcgctattac cgaaaccgag atgcgcaccg acaacgccaa  71460
atttcgtttt atcgggcgcg atgcctacga ggcagcaggg ggttacgtcc gtgaagatct  71520
gttcagccag gacgagggcg acggcacggc agacagcgtg ctggttgagc gtctggtgca  71580
ggagaagctg gagcgtatcg cgcaggacat tcagcagcgg gagggctggg catggagtcg  71640
cggacgcgca gcccgcatct ggtaccacgg cgaagacggt aaggagttcg tgcagcctgt  71700
tgaacccgat ccggtgtaca cccctgagca gcagcagcgt cttgatgcgc tgcgggagca  71760
gtacgataca tatgacagcg tttgcgacga gtcagatgcg atcgaagcgg acatcctcgc  71820
cattcaggag gcggcagaag ccagcgcgtg gactgacgac atgaagtcag gcgcgggagt  71880
gatggtcagc ctgtacgaag ggcaggtgta cgtgcagcgc ggtgtgcgcc tgaaagcgga  71940
tatgccggaa gaaaccgtaa ccagcagcgt aacggtgcca ttcacctcac gccagcccga  72000
cgccgcagag gggatcagcg ttccgctgct cactaaaatg acctccgagc gtacgctggc  72060
agtacaggcg gcgctgatgc agcagcccga aaaagcggtg gcgctgatgg tctggcgcat  72120
gtgtacctgc gtcttctcgg gctgtctgac cacgacgcac ccgttccgta tcagtctgac  72180
cgtgtcccac ggcagcctga cggagaacgc cccgtccggt aaggatggcg cagcgtttga  72240
gatgctcatg accgaacggg caaggctgaa agccctgctg ccggaagggt gggagaagga  72300
cttcaccacc ttctttgccc ttgacggcgg ggtgttgatg tcgctgatgg ccttctgcac  72360
ggcctgttcc gtggacgggg tacagacccg cgatatgggg cacacctccc gaagtccact  72420
cgatacggtc gaggcggcaa tcggattcca cctgcgcgac tggtggcagc cgacgaagga  72480
caactatttc ggtagcctga aacatccgca gattgtggcc tccctgaaag aggcggggct  72540
gacgggcgcg gcgggtgacg cggagaagat gaagaagggc gatgcagcag cgcatgcgga  72600
gcactttatg cagcacaccc gctgggttcc ggcatggctg aaaggaccag agccagcggc  72660
tgaatccggt gctgacgacg cggtttccga taccgacagc actgacaacg acaccaccaa  72720
cacggcacac gccgcctgat aacggagagc cgcccttgtg tgaacagggc ggcaattgta  72780
```

-continued

```
acgaacggtg caatagtgat ccacacccaa cgcctgaaat cagatccagg gggtaatctg  72840
ctctcctgat tcaggagagt ttatggtcac ttttgagaca gttatggaaa ttaaaatcct  72900
gcacaagcag ggaatgagta gccgggcgat tgccagagaa ctggggatct cccgcaatac  72960
cgttaaacgt tatttgcagg caaaatctga gccgccaaaa tatacgccgc gacctgctgt  73020
tgcttcactc ctggatgaat accgggatta tattcgtcaa cgcatcgccg atgctcatcc  73080
ttacaaaatc ccggcaacgg taatcgctcg cgagatcaga gaccagggat atcgtggcgg  73140
aatgaccatt ctcagggcat tcattcgttc tctctcggtt cctcaggagc aggagcctgc  73200
cgttcggttc gaaactgaac ccggacgaca gatgcaggtt gactggggca ctatgcgtaa  73260
tggtcgctca ccgcttcacg tgttcgttgc tgttctcgga tacagccgaa tgctgtacat  73320
cgaattcact gacaatatgc gttatgacac gctggagacc tgccatcgta atgcgttccg  73380
cttctttggt ggtgtgccgc gcgaagtgtt gtatgacaat atgaaaactg tggttctgca  73440
acgtgacgca tatcagaccg gtcagcaccg gttccatcct tcgctgtggc agttcggcaa  73500
ggagatgggc ttctctcccc gactgtgtcg ccccttcagg gcacagacta aaggtaaggt  73560
ggaacggatg gtgcagtaca cccgtaacag tttttacatc ccactaatga ctcgcctgcg  73620
cccgatgggg atcactgtcg atgttgaaac agccaaccgc cacggtctgc gctggctgca  73680
cgatgtcgct aaccaacgaa agcatgaaac aatccaggcc cgtccctgcg atcgctggct  73740
cgaagagcag cagtccatgc tggcactgcc tccggagaaa aaagagtatg acgtgcatct  73800
tgatgaaaat ctggtgaact tcgacaaaca ccccctgcat catccactct ccatctacga  73860
ctcattctgc agaggagtgg cgtgatgatg gaactgcaac atcaacgact gatggcgctc  73920
gccgggcagt tgcaactgga aagccttata agcgcagcgc ctgcgctgtc acaacaggca  73980
gtagaccagg aatggagtta tatggacttc ctggagcatc tgcttcatga agaaaaactg  74040
gcacgtcatc aacgtaaaca ggcgatgtat acccgaatgg cagccttccc ggcggtgaaa  74100
acgttcgaag agtatgactt cacattcgcc accggagcac cgcagaagca actccagtcg  74160
ttacgctcac tcagcttcat agaacgtaat gaaaatatcg tattactggg gccatcaggt  74220
gtggggaaaa cccatctggc aatagcgatg ggctatgaag cagtccgtgc aggtatcaaa  74280
gttcgcttca caacagcagc agatctgtta cttcagttat ctacggcaca acgtcagggc  74340
cgttataaaa cgacgcttca gcgtggagta atggcccccc gcctgctcat cattgatgaa  74400
ataggctatc tgccgttcag tcaggaagaa gcaaagctgt tcttccaggt catcgctaaa  74460
cgttacgaaa agagcgcaat gatcctgaca tccaatctgc cgttcgggca gtgggatcaa  74520
acgttcgccg gtgatgcagc actgacctca gcgatgctgg accgtatctt acaccactca  74580
catgtcgttc aaatcaaagg agaaagctat cgactcagac agaaacgaaa ggccggggtt  74640
atagcagaag ctaatcctga gtaaaacggt ggatcaatat tgggccgttg gtggagatat  74700
aagtggatca cttttcatcc gtcgttgaca gttgcctcaa tgtgcgctga cgggcaggac  74760
gtgtttcgtc gcttcctact gaaagatccg aaagccggtg tcggtatcag tctatgcaac  74820
aaggtgttcg aaaacccaat tccgaagttt gaggtacagc tggcgtctcc gtacaaggag  74880
aaaggcgaca aatacccatt taaaccaaac ccaaaggcca agtggccaat gatcggcagc  74940
ctcaaactcg atggtctccg ggttatctgc gaagtcatcg tggatgagga agaggtgaac  75000
ttcctgacgc gcaccggcaa tccgattacg tcactcgatc accttaaacc ggccatgctg  75060
gagcgtggcc ggctctccgg tttcaagcac atcttcttcg atggtgaggg tactgcaggt  75120
```

-continued

```
acgttcaacc agtccgtgtc ggcgcttcgc aagaagaacg tgaaagccat tggtgccgtt  75180
taccacatct tcgatttctt cttaccagag tggcgtgctc aggcaaaaag caaagagtac  75240
ctgaagaccg gtatgaagct gaaagagcgc ctggctatgc tggtgtcatt gttccgcaac  75300
acttgcgggg aagattacgc gcaagatatc cacctgcatc cgttctacat catccatagc  75360
catgaagact ttatcgaacg cttcatgaag cgcctggatg agaatgaaga gggggagatg  75420
ggcaaagatc cggattctgt ttacgagttc aagcgtaccc gcagctggtg gaagctgaaa  75480
gacgaggatt ccgaagacgg tgaaatcatc gacttcgagc caggcgaccc ggactctggc  75540
tttgcgcata cgctaggcaa gatagtgatt cgtctggaga acggcgtcat cgttcgtgcc  75600
agcggtatca aacataagta cctggatgag atctggaaca atcaggagaa atatcgtgga  75660
cgcatcgtcg aggttcactg ccatgagaaa acgccagacg gtagcttacg tcaccctcgt  75720
ctgaagtggc cgaaatgtct gcgtgatacc gaagatcgta ttggagataa agactgatgt  75780
tcggctggat gattgtattt ttggttgtcg gcattgttat cggcagtctg gttatgtcca  75840
gctgcatcaa cgattacgta aaagccggtg tcatgcagag gcgcggccgc atttaccgca  75900
ttgtagatat cacgtacaca ctgaaggaga ttaaggatga tcatgttaag taaacgggag  75960
aaggaaaccc tgcgtgaaat cagccagtgg aaggagttct acgctaactg gaagccaaag  76020
acccgcgcca aactggaacg catgaatctt gtcgctaacg tttcgccaaa gggatgcttg  76080
gagaactatc aactcactga aaaaggacac tcactgttgc agcaattgac tgaggctggt  76140
gcgttccaat gattccatac atcacattat cttttgctgg gggcgtggcc ctcggcttca  76200
gtatctgtcg cgatctggtc aggcaggaac tgaaaaccaa aacgcttcgc atcggtaagc  76260
gtctgtatcg ggttgttcac gagacaggag tgcagaaatg agcaatttga cctctttcga  76320
ctggtggctg gcaacctacc ttgtggcggc cggcttcgga tatgcctttt acgttggtca  76380
gttaatcgtg aagctattgc tgatcagatt tgccagccat aaacgcatag atgacggtct  76440
gtggcgcctg ggttctctgc tggagactca ctacggcgaa ctcaaggaga acgaaactat  76500
cactattcaa gcgaagcgtt ttaccgccat catcacgaga acgccggaac agaaggtgag  76560
tttgatcaaa aagatagcaa ctgaacgagt cacagacaaa taagtattta cttacttatc  76620
tattatgtat aagattcatt tgttttcgtt gggacgcgac tgtttgaacg ttaaatataa  76680
ctgcaaacga agatacgtac ctggcagtag cctaagaagc caaacaccag cgaggtcagt  76740
ttccagcctc gtcaccgaaa tgggacacac tgagcgagtg tgattgcaga acgcaggata  76800
gggcatgttg caccacccat gccctattcg atgaagtaac aggatgggcg gttggtttcc  76860
tcattccatt ccatcatccc ggtttcagcc agctgaccgt ccatcctgtt acgtcatttc  76920
cattacttat gtcgtttaat cttgggttaa aagcggcgac gtaacccggc tggctcggtt  76980
agccagcgca caacgttgag gtcactgttt tttcttttaa tcatacaggt gattccacag  77040
aactgtagtg actgatcaat atgttgggtc gaacataaat cggttcagtg gcctcaacgc  77100
tgtgaaatcc aaaataatta actctttggt aatcctaatg ttactgacat ttccggcttc  77160
acaatattat tgtgatatac ctgcatttca ttgtaaaact ccatgtcatc acaataaatc  77220
gggagaaaat aatgacaatc aatagtattg tcatttcgtc tttttatgac ctccacatcg  77280
taaccatccc gcttatttaa attataaata ggcaaagagt tataatatat gttgtacatg  77340
tgatgaacat actgatcata tgtatcattg aagaaaaaat aagcatacag gcctttatct  77400
acctttattt cactatcgct gaaatgctta ttcctatccc aaacaaccgt tcttgcaata  77460
atgtcattcg ttttatcatg aaaggggatt ctgtttgata ctgttatagc tgtatttttc  77520
```

-continued

```
ttcaacgaat catataactt acccaatcta cattttgaat ctatcccaga gtagaacact  77580
aaatccctaa aattaaagca ttgaccaatt atatttctct ctttaaggta acagattcgt  77640
ggttgaaggt attcacagtt aatttccctt ctacccaaca aacctttaaa ggaccaaaaa  77700
gggatcatcc tatactgccg tggggtataa ccaaatattt tcttaaattc tctggtgaat  77760
gtctgttgcg aatcataaaa aagctttgct gatatctcta ttattgtcag cctggtaagc  77820
cgtaatagtg cagcagctct actagccctt ctaactctaa tatatgttcc aataggcatt  77880
ccgacatatt ccttaaagga aatttgcaaa taccttctgc tgaatcctga atacaaaacc  77940
aaacagtcaa tgttaatgaa tttcgactcg agattctctt ctatatattg aataattgaa  78000
tttacagtca tctgttttag catgaatata acccaaatca aaataatagc attctagata  78060
gtgggccggc gccgggactt agctatttgc gcatacccag caacaccaat cttagctatt  78120
tgtgcacgcg catcaatatc aaaattagct atttgcgcaa caagcaagtg gagtgcgcga  78180
aaagctaaac tttgtgtgca tttttaaata aaattgttct cagtgaggct gtgctacgga  78240
tataaaaatc cccttcattt gttacccacc tttttacgca tatcgtcgat atgaaatgat  78300
ggggaggggg tgggaaggtg ttgtcaccat tccgtaagga ggttaagctc atgattttaa  78360
atagattaag tacgttagga attattactt tcggcatgct tagttttgct gcgaactctg  78420
ctcaaccaga tatcaaattc gcaagcaaag agtatggcgt gactataggt gagagtagga  78480
tcatataccc gttagatgct gctggcgtta tggtctcggt gaaaaacacc caagattatc  78540
cggttctcat tcagtctagg atctacgacg agaataaaga aaaagaatca gaggatcctt  78600
tcgtggtcac tccgccattg tttcgattgg atgctaagca acaaaattct ttgcgtatag  78660
ctcaggctgg aggtgttttc ccgcgagata aagagagcct aaagtggtta tgcgtaaaag  78720
ggattccacc aaaggatgaa gatatatggg ttgatgatgc gacaaataag caaaaattca  78780
atccagacaa agatgtggga gtgttcgtgc aattcgcaat taataattgc attaagcttt  78840
tggttcgacc gaatgaatta aaaggaaccc ctatacagtt tgctgaaaac ttaagctgga  78900
aagttgatgg ggggaagcta attgctgaaa acccctcacc tttctacatg aacataggtg  78960
aattaacatt tggagggaaa agtattcctt ctcactatat tccacctaaa tcgacgtggg  79020
cttttgattt gccaaaagga ctagcgggag cacgtaatgt ttcgtggaga ataattaatg  79080
atcagggagg gttggatcgt ttgtattcca aaaatgtgac tttatgatga tgtttaaagg  79140
ggacgggaat aatgaggtat tcaaagctgt tcctgtgtgc agggttaact ttggcaacat  79200
tgccttgttg gggacgcgca tatacttttg actctactat gcttgatacg aatagtggag  79260
agagtataga tgtatctctt tttaatcaag gacttcaact tccaggtaat tattttgtta  79320
atgtttttgt aaatggtcga aaggtagact ctggaaatat cgacttccgt ctagaaaaac  79380
ataatggaaa agaacttctt tggccatgcc tatcatcctt acaattgaca aagtatggca  79440
ttgatataga taaatatcct gatttaataa aatctggtac agagcaatgt gttgatttat  79500
tagcaatacc acattcagat gtgcagtttt attttaatca gcagaaatta tcgttaattg  79560
tgccaccaca ggcactttta cctagatttg atggcattat gccaatgcaa ttgtgggatg  79620
acggcattcc tgctctgttc atgaattata atacgaacat gcagacaaga aaattcagag  79680
aaggaggcaa gtctctggac tcttattatg ctcagttgca accgggatta aacatagggg  79740
cttggcgctt tcgtagttca acctcatggt ggaaacaaca aggatggcag cgttcgtata  79800
tttatgccga gcgaggattg aatacaatta agagccgttt gacattgggg gaaacctatt  79860
```

-continued

```
ctgatagcag tatctttgac agtatcccga ttaaggggat aaaaattgct tcagatgaat  79920
cgatggttcc ttattaccaa tggaattttg ctccagttgt tcgcggtatc gcacgtacac  79980
aagccagggt agaggtttta agagatggct acactgtaag taatgagttg gtgccctcgg  80040
gaccatttga gttagcaaat cttcctctgg gtggggggag tggtgagctg aaagtcatca  80100
ttcatgaaag tgatggaaca aagcaagttt ttacagttcc atatgacaca ccagcagtgg  80160
cattacggaa gggctatttc gaatattcaa tgatgggggg agaatatcgt ccagctaatg  80220
atcttacaca aacatcgtat gttggcgctc ttgggatgaa atatggtttg ccaaggaatc  80280
ttacgttata tggtggacta caagggtccc aaaattatca tgccgcagct ctgggtatcg  80340
gtgctatgtt gggtgatttt ggtgccatat ctacagatgt tactcaagca gacagccaga  80400
aaaataaaca aaaaaaagaa agcggccaac gttggcgcgt tcgatataat aagtacttgc  80460
agagtggaac atcgttaaac attgctagcg aggaatacgc cacagaagga tttaacaaac  80520
tcgctgacac gttaaatact tattgtaaac ctaatactag aaacgattgc cgttttgatt  80580
atgctaaacc caaaaacaaa gtgcaattca atttaagtca aagcatacct ggttcgggga  80640
cgcttaattt cagtggctac agaaaaaact attggcgtga cagtaggagc acaacttctt  80700
tttctgtagg ctataaccat ttttttagga atggtatgtc attgacttta aatttatcga  80760
agacacagaa tatcaataag tatggagaaa aaactagtga gctattatct aatatctggt  80820
tgagttttcc tctcagtcgc tggctaggta ataactcaat aaattcaaat taccaaatga  80880
catcagattc tcatggtaac actacccatg aggtaggtgt gtacggtgaa gcctttgatc  80940
gccaattata ctgggacgtt cgcgaacgtt ttaatgaaaa gggcagaaaa tatacctcca  81000
atgcactgaa tttgaattat cgaggaactt atggggagat cagtggtaac tacagctacg  81060
atcaaaccca aagccaactt ggtataggtg taaatggcaa tatggtaata actcagtacg  81120
gtataacggc tggccaaaaa actggagata ctattgcatt agtacaagcc cctgatataa  81180
gcggtgcttc agtgggatac tggccaggca tgaaaacaga ctttaggggg tacaccaatt  81240
atggttactt aaccccttac agagagaata aggtagaaat taacccagtt actttaccca  81300
atgatgcaga gataacaaat aatattgtta gcgtgatccc gacaaaggga gctgtagtat  81360
tagcaaaatt taacgcaagg attggtggac gattgttttt acatttaaaa cgctctgaca  81420
ataaacctgt tccatttggt tctatagtta ccattgaagg gcaatcatcc agctctggca  81480
ttgtcggaga taatagcggt gtctatttga ctggactacc taaaaaatca aaaatacttg  81540
ttaagtgggg gagagataaa aatcaatcat gttcatctaa tgtagttcta ccagaaaaaa  81600
cggatatttc tggtgcttat aggttatcca caacctgcat cttaaataac tgaaacggat  81660
gtttatttca aacaggacac aagccctctc tacgaatttg ttcgtggatt ggattattcg  81720
atagaggtaa tatatgaaaa aaatcagttc cgttatcgcc attgcattat ttggaactat  81780
tgcaactgct aatgcggcag atttaactgc aagcaccact gcaacggcaa ctcttgttga  81840
accagcccgc atcactctta catataagga aggcgctcca attacaatta tggacaatgg  81900
aaacatcgat acagaattac ttgttggtac gcttactctt ggcggctata aaacaggaac  81960
cactagcaca tctgttaact ttacagatgc cgcgggtgat cccatgtact taacatttac  82020
ttctcaggat ggaaataacc accaattcac tacaaaagtg attggcaagg attctagaga  82080
ttttgatatc tctcctaagg taaacggtga gaaccttgtg gggatgacg tcgtcttggc  82140
tacgggcagc caggatttct ttgttcgctc aattggttcc aaaggcggta aacttgcagc  82200
aggtaaatac actgatgctg taaccgtaac cgtatctaac caataatcca tatagataat  82260
```

-continued

```
agataaagga gggctattat gccctccttt aatatttatg aattatccta ctttgagcct  82320
aaccctcgct tttcttaatc acggcattga tagcaagact gacaaattta tgtgaagatc  82380
aatgttagga actaatgcag aaagccacgc cctcaataga tttcacataa tacactatta  82440
gctaagaata gagagcgcga agcaatataa taggctcata tttataactc tcaccttaat  82500
atgcacttgc aataccattg agtatattat ctggtgggaa tttttttctc ctaagcgagg  82560
atatggtgtt ccaaaagcga tttcaacata tccgcctaac tgcgggaaga attattgttt  82620
taggtgtggc aattatttta atggaaatct tgttgttagg gattttgttt tttattagcg  82680
aaataatccg aaatttataa tcaccctccc ttttgcgtca tttctttcag gcgccctcac  82740
cctcttgagg agagcaagag gggtatccat catccatgca acttcaacaa agcagccttt  82800
gccctcaccc cggggttttt ttatttggta gcaacccacg tcctgcagcc ctcaaaacct  82860
tcatagccgg taaaaatgat tccataccta ttaagtatgg aatcattgta caaaacaggc  82920
tattttatgg ttgatcatac aaaaacttat gcctaatata ctgttcatgc atacagttaa  82980
aagggcttca ctcagtgagt ggacgatgaa aaacaccttt gataaagcac gcgcagcaga  83040
aaatacctct cgggaagcca tcgagtacct cgaacgcgct tccggtttgt cggcagtgtc  83100
gaccgccaat ttcgacggag acatgtcgtt ttcttccgcc ttcatgttgt tcacccgctt  83160
atccttactg ataacgagac gtcgacctga aattgccgtt cattgtgttt tgatacatgt  83220
gatgccgcat atctctgaag taaaggtaag tgatataagt agggtcttgg tcaaccagct  83280
ggtgaaccca ctgatactgg aaggcaagat cgtccagggc agacgcgtgt tctccctgat  83340
gaaacagttc ctgagctggt gtgcctttca gggattgatt gatacttcac ctttgaatga  83400
tatgtcgctc aacaaagttg ccggtggcgc aaagccagta ccgcgcgaac gtaagctgac  83460
cgacgctgaa gtctgggtat tctggaatat ctgggattat ttcaacgtat gtgaaggtac  83520
aaagtgggcg gcaaggctat gtcttgttgc tgccaggcgt ccagatgaag tgctccgggc  83580
cagaaaggat gagttcaacc ttcaacgtga tgtatggaat caaggtacgc gaaacaaatc  83640
ggccagacag cacgcgctgc cgctaagtcc attaatgcgc aaatgcgtgg aagagttgtt  83700
cgaatacgga aagggcagcc agtggcttgt tccgtcaaat aagaagaagg gcgttgatac  83760
accaatgtcg aaggtggcca ttgcacaagc gttgagaaga attctggagc gcccagagct  83820
gatggatttg gaacctttca caccacgaga cctgagacgt accgctcgta gttattttcc  83880
agccctgggg atcaatcaag aagtggctcg taaaataatg aatcacagtt tggaaggcat  83940
agatcgcgtg tacgaccggc acgactatat ggatgagatg cgagacgcct tggatagatt  84000
ctcagcgtac atcgcatcca tcgtagagca acaagattta gacgaaattg accacaaatt  84060
taagggagat cgtctagcaa ctgagcttat tcgtgtaaat ttctcatagt ttcttgattg  84120
cttcaacaac ctgatctgat gcgccgcgtt gatcaccgaa acggttgcga aacgcttcta  84180
atactctttt ttcgtctgcg gaaaggggag ccgttccttc ttcgcggaag aactcaagca  84240
actccgggtg acgctcttcc aggaccatca gcattagccg aacagggtca gcgtccagag  84300
ctacggccag cgctcttacc ttatcaacgg ggagagggat ctttccgctt ttgatgagag  84360
acaggttgtt ggcgttttta taccctactt ccttggcaat agtagcctga cttttcggtg  84420
agatagtgat cagggaatca atataagccg cgtagcgacc ttgtttgcta tctgtttcgt  84480
tggtagccat gtaataacct tgcgtgttta atttgtctct ggtaagtgct tactgatatt  84540
acattaaagg tgagggttgt aaagacttat ctatttcttt cgataggcat caaaaccctt  84600
```

-continued

```
tacctatgcg cattatacat ctattaagcg gcaaattgtc attatcagct tgcatggttt  84660
gtcagacaaa tctgatatag atgtattccg tattgataca ataggtagta gtatttccga  84720
actttcgaac gtgttgagtt ggatgatatg agatgaaaaa tataacttct aatttgaacg  84780
cccttgaggt tggacatgca tatgcgctcg ggatggatgg cgtggcaacg atacttacag  84840
aacttaatac tgaagaactt ccgatagaca tgagcgacac gactgtcttc actttcgaac  84900
tcagcaacaa acatttcact ctcatcaata ctggctgcgg ctcacttgcc gtaagaaccc  84960
attaactgca aatcctacct attgaaacct gtacgaacag cttggccacc tgttcgtaca  85020
gcataaaatt acacacatta gaaaacaaat tgttttaata acaaggaaat tctcatgtcc  85080
aaagccatga ccagagctgt gctgaaagag gtacaggact tccgcgactg cgtaaaacga  85140
gttgtagcga tgctttcagg caaacagata cctgttgcag aacgaggcaa tgaagcgtat  85200
gtccgctaca accggcgcgg cgaaccagtg ctggtaaaca tcccatctat accggacgac  85260
gcatcaccaa ccctcatgaa cgcagtacgt ggttttctcg accatgaagt agcccatatc  85320
ctctttactg atccgaaagt cgcgatgaag atgcgcgaga gaggaaaggc tccgtctacc  85380
gggctttgga acgcgctgga agacgttttt attgaacgca gaatgggaca ggtattcaac  85440
ggaacccgtc gtaatttgct agccacacag aacctggtga tcgacaaata cttcaagggc  85500
aaagtgtcag aggcggtttc aatctgccac ggcaaccagc gtgaattgtt cctgaaattc  85560
ttcctttgcc cggtcgtccg cgcctgggat ggccaaagcc ctttcatcga ctttatggaa  85620
gaacactggc acctcatcga taagcctgta gccttgctca aagagcatgg tatcgacgtg  85680
gccgttcgca atatgtcgaa cacagaggac tgcgtaaagg tcgcagctgc tatcgcccaa  85740
atcatgcagg atatgaaaga caagccagag ggcaaattac ctgagcttaa atcatctgcc  85800
aaaaagccgt ctaagagcaa agacgagtcc gaggaaacac cagagtcagg cgacgatccg  85860
tctcatagtg aatctgcacc aaagcgaacc aaaggcgaag acgacgacaa ggaagagcaa  85920
gaagatgatg cctcagaaga ggaagattct ggggattctg atttgcctga ttcattagat  85980
aaggacttac ctatacatga taaagaaatt agtgatacag aaagtaaata tacagaagca  86040
ggcgaagatg agtcaggaga caccccagaa tccgatgatg ccggcatgga atcaggtgat  86100
tctgacgacg aaggtggtag tgatggcact ggcgctccaa cgcctggtga tggcattcgc  86160
gaagacgccg atgactccga tggttatggc tctggcgccg ctggcgatgg ggatagtgat  86220
aacggcgaag actccgatgc cggtcgtgag gagtccgaag gagaagacga aggcgaagag  86280
gacgtcgccg atcacactga cggcgaaggc aaggaaaatg aggatgccgc ggaagcgcct  86340
gaagacagtg agtcaggctt tgttcctgcg ccggatgaaa tgactctgga ggacgcactc  86400
aaggcgctcg acgagatgga agaaggaaca gacgaaatga ccgaagacgc actgtcggcc  86460
accatcagca aagagcttat gagcgcctca ctttctgagt atcgcccata cgatcgttca  86520
tacgacttta tcgggttgat tgatgaggct gaagagcatg taaaacgcac cagaaagaca  86580
ttcggcgcaa tcccaatgca ctcacctgtc gatcgctacc gcatggttcc ggaaggcaga  86640
aaactctttg aactgaaaat cgaaaaacat ctgtctgccg gcgtttcttc gactctggcc  86700
aaagacctgg agcgagctat cgccagccgc aaccgagttc agttcatacc gggtcagaga  86760
cgtgggcgga tacatggcgc gaacctgtat cgtctggcaa tgaacgacga ccgcgtgttc  86820
cgcaagaaag aagaccacag agcggtgaac gcgtgcgtcc agcaggtgat cgacttgtcc  86880
ggctcaatgg gcggcaggaa gattcaactg gcactcgcca gcgcctacac cattgcggat  86940
gctctggatc gtatcaatgt gcctaacatc atcaccggct ttacaacgtt tggtagccca  87000
```

-continued

```
gattatgaaa ccatgtcgaa gcgcgggttt acacgtttcg aggcgctcat gctgcccatt  87060
atcaaaaact ggaatgagaa agctaactca ccagagatcc gcgcccgcat gggctgcgta  87120
tgtgagacgt tccccctgct caataacgtc gatggtgaga gcgtcgcgca gctggccact  87180
ctgtttgcag ggcgaatgga ggacaaaaaa atcatgctgg ttatgagcga cggggcacca  87240
tgtgctgcag gcgatgggtt ccatgagcat ttgcgaaccg tcaccaaaga aattgagacg  87300
ttaagtgaca tcgatttgat ggctatcggt gttctgactg acgcaccacg acgctactac  87360
aaaaattacg cactggttaa cagcgtagaa gagttagggc cgtcagtcgt cactgagcta  87420
tctcgtatca ttcttgggta agaacttcac ccttaaaaaa taagtaatta cttactatac  87480
agtctaatat atttatataa gatatacccc acgaacgaca aacagtaagg aaaaacacat  87540
gaccgctact gcactacagc aagaagaaca tttgccggaa gccatcgtct gcaagtggtg  87600
tggcaaatct tttcattacc tgaaatccca tatctctatg ggccgttgcg agaacattcc  87660
tgagtccgcg aagggtctgg acgtggacga agtggtgaaa atgtacacct ctgcgtttcc  87720
agatgaacca acgatctctc gcacggcact ggtcaaactc aatgagaagc gtgccgaaag  87780
acattcagga gaaggaaaag tagcggagat tagcgcacat ccgggctacg caggaacggt  87840
cgaatacaag accgaactgg tggccgcgca cgagctgctt ggcgtaacga tcaaagagct  87900
gggaacgcca cgcggaaaac cactacaggt gacggttaac gtcaacacac cctatccgga  87960
gttcgtgcct gaagcgaaga agaactatgt gtatggcgac tttgacctga ttaaagacat  88020
cttcatgatg ctggaaatcg gaatcccagg ctatctctgg ggtcatgcag gaaccggtaa  88080
atcttctctt cctacgcagc tatgcgccct gctgaatcga ccactgatcc gcgcccagca  88140
tacggcgtct atggaagaag cacacgttac aggccagatc ctcgctcgcg atggctccac  88200
ctacttcgag ccgggtttgc tggcgctggc gatgaaaaat ggctgggtgt acctagctga  88260
tgaatatgac ttcgcgttcc cgcagattct gggtgtgtac cagccagttc ttgaaggaga  88320
accgctgatc atcaaagagg caactccgga ctggcgccgt atcactccgc ataaacgctt  88380
tgccttcatt ggcactggca acactaacgg ctctggcgac gaaacgggtc tctatcaagg  88440
tacgaacatc cagaacgcgg cgaacttctc gcgcttcggc attgtttcga acgtgaagta  88500
catgagcact aaggctgaag tcaacatgct ggctgaggct ggcgtcatcc gcgaatacgc  88560
cgagaagatg gtgaaattcg cgaaccttgt ccgtgaaggt tatgagcagc atctgatcag  88620
ccagccaatc ggtcctcgcg agctgctgct atccgcaaaa atcggaatga tgcgcggtga  88680
tttctctgcc ggcatcgaaa agtcatttat caataaactt ccatccacgt ctgcacaggc  88740
agcgcgtgaa gtggttcaga agatcttcgg ttaatcgtgc gtaaaggatg tttcggctct  88800
cttatcgcag cgtctgaaac tggccgggct tgtctggcgt gtccggatag gtccgagtgc  88860
caccagtcag ccaaagaggt tgcgatttcg atgtatggga agttcgttgg cttccccaat  88920
gacaaaatca agaaaaccag aaaggtaaaa acacatgaag gctctgatgg tcagaactga  88980
cttctccctg ggagagtcag ctctaaaagc agaaaacgcg gtgaaaatcg cgagagacgc  89040
tggctacact gctgtcattt ccgctgacag catgaacatt gccagtgtga ttcccctgca  89100
gcgtgccgct ggcgacgata tggcggttat ttgtggtgtt aagctgaatg tggtcgacga  89160
tccgacatac gagcaccgcg cccgccttgc gaaagaatca gagagatgta tggaatcatt  89220
ggtgcgtgat cgcagctact gcttcacggc actgataaag aatgagcaag gttatcgcga  89280
cgtgtgcgaa ctgatgacct tagcgaacaa gcgcgagcaa ttctactttg tcccgcgtct  89340
```

-continued

```
ggcgctcgac caactggcgg ccgcgtatgc caaaggcaac atcatcctgc tgacgtccga  89400
cattggcagt gtattccagc gccgggactt cgcaaagatt atcgggacgc tggtcacagc  89460
tggaggacgc gataacttct acagcgtggt ttatccgcac cctaccccat tctacgacca  89520
gattaacgtc cgggcgatga aagtagcgag cgcactgaaa atagagccag tggcgttcta  89580
tcccgcttat tacgaagcgg tcgacgacgc tgacattaaa gacattgcgc acatggttac  89640
gaacaacatc aaaatcgacc agccgcatcg tctgcgtatt ccccaccagc gagataacgc  89700
cgttaatggt cgccgccatc tccttgaagc gctgaaagcc ttctccgttc gcatggatgt  89760
accggtaaca gctgcaatgg cctcaacaac gcaggacacc attatcgaag cctgcacatg  89820
gcgctggcat gaattgccac cagcactgcc caagatggca gacgacgagc ctgcaacgct  89880
gatgaagctg gctgtcgcgg ggctgcgcaa gcgtcttact accaaagagt ttggctacac  89940
accaccggct tctgagcacc gcgtgtatgt tgatcgtctg aagtacgaaa tggacacgct  90000
gacccgtctg ggcttctgtg gctacttcct gatggtgcgc gacctgatga atcacagccg  90060
tgaaactggc attcctgtcg ggccaggtcg tggttcctct gccggttctc tggtggcgtg  90120
gtgcatcggc ataaccaacg tcgatcctat ccgtcacggt cttctgtttg agcgtttcat  90180
caaccctgaa cgtctcgact taccggatgc ggatctggac ttcagccagg cacgtcgcca  90240
tgaggtgatc gagtatctga atgaacgcta tggcgaagat tacgttgccg gtattccgaa  90300
cttcacctat ctgggcgcgg cttctgcgct gcgtgacacc gcacgtattt acggtgtcga  90360
tgctgcggat atggcggtat ccaaagagtt caagaatctg gaggacgata gcctgtcgct  90420
ggaagagctg cgcgagcaac tggccagcct ggacaaatac gccacgaaat acccggaagc  90480
gttcaaagcg gcgtgtaagc tgcaaagcct gatgcgtggt tttggtcgcc acgctgcggg  90540
gatgatcgtc gctggcgttc cactggtaga gcgcacgccc gtcgagctgc gtggcaatgc  90600
tcgctgtatt gcattcgata aacgttactg cgaggcgatg ggctgatta agctggacgt  90660
tctcggtctg gcaacgctcg atctgttgga tagcgcgaaa cgctacatca aagagagtac  90720
cggggaagac atcaatctcg atgctatccc actggacgat cgtaaggttc tggatgggtt  90780
cgctgcaggg tacacgcagg gcgtattcca gctggagtcc ggtcccatgc gcaagctgct  90840
taaagatctg ggcggtggca tcgagccaat gagcttcaaa accgttgtcg ccacgaccgc  90900
actcttccga cctggcccga ttcaatccgg catgttggac gactatgtct ccgtggccaa  90960
aggcttcatg gctccacagt cgctgcaccc ggtactggac gagcttaccg cggaaaccaa  91020
cggcgtgatt ctgtatcagg aacagacgat gaacgcgaca cgattgctgg ccggtttcac  91080
gatggccgaa gcagatggtg tacgtaaagc gatcggtaaa aaggatatgg aaaagatgaa  91140
gagcatgggc gagaagttcg tcgttcaggc tcaagctggt tggatcgacg ttgagatgga  91200
agacggcacc acgcagcgta ttcaccgcgc ggaacacttc aaatgtgagg acggcgcact  91260
gcggacggtc gaagaagcgc tggaggcagg tgtgaaattg ccgatggctg ctgtacgcgt  91320
tacagggtca caaccgggct tgtctgagac gaaagctaag gagatctggg atgccttcga  91380
gaagaacggt gcgtatcagt tcaacaaatc acatcccgtt gcctactcgc tgatcagcta  91440
tcagtctatg tggttaaaga cacattaccc tgctgagttt ttcgctgctg cgctcaccat  91500
tctgggcgag gataagcacc aggggctggt taaggatgcg ctgacctatg gcattcacgt  91560
attgccacca gacgttaacg tgtcatctaa ccgaattgag atccgcacgc tggaagacgg  91620
cagccaggtt ctgtatgcgc cattctctgc tgtaaaaggc tgctctgaga atggttgcca  91680
ggccatcatg agagcgcgtg agaaagttgg cggcaaattc gagtcacttg agcaatttga  91740
```

-continued

```
ggaagcggtc gagaagcgtg cgtgtgcgtg taacagccgg gtacgcgagt cactgcaaaa  91800
agtaggtgcg ttcgcatcga ttgagcctgg cagtctgcca gcgacagatc cggaacggct  91860
gcgcgaccag gctgaattga tgggcaatct ggtgatcgac gctgtaaaag cctctcgacc  91920
gttcgagatg aaccctaaac gctctgccga agtgaatgta ctgatgacac gcatggcggc  91980
tgaaatgggt ctgggagacg acctgatacg cccaagcatt ggcattaagc cgaaaatcat  92040
ggtcattctg gacaacgcga acggcaatga tgggcgtact ggctacttca tggagaacgg  92100
ctacgacgac tttaaggcga agttgcttac tgcaggcgat ttgcgcatgg gagatctcta  92160
cgtcaccggc gtgtgcaaaa aggtgaagga caaagagaag gactacacca aagacgagat  92220
aggccagttc accgacttta tgcgtgaaga gatcaatctg gtgcgtccga cctatgtgct  92280
gacgtgtggc agccgggcga cgtcactctt caacaacaag agcaaaccat ccgacctggt  92340
tggacgcaaa gagtatctgc cagagctgga tgtgaccgtt ttctacggat ttaacccgaa  92400
cattttgtac tttcgcccag aggaaggcga aaagctggaa gcaattctgg cagaggtagc  92460
ggagacaatt agcaaatgaa taaagagaac accatgaacg aagcacagaa gattgcacaa  92520
gcgctggcgg ctatcccagc ggattttcag gataaagcag ttgcagccac catgcggtcg  92580
cagttctggg aaatcatcga ctgcccggtc acgttagatc tggcgctggc gttcgccggg  92640
ctggatggtg ccgataaagt cagtcgtctg cgtaaatgtg ccagagcgct ggcgcttaaa  92700
acgcaagatc cgaaggcgtg ccagtatctg ctggagattt acgaatcgga taacccagag  92760
gaacagctgg aggcgttcaa agtgttccgc aatcggctgg tgctgaaggt ggccaaagag  92820
tttatggaag tgaacaagat tggcgatgtg agacagtaca ggctgaaacg ccagaccaga  92880
gtcacgctat ccaacatttt tggtaagaaa gtcgcataaa gcaaaaaccc gccaatcggc  92940
gggtttttc atgcgcattc ggcgtgatga cgtcgacgtg cgataagtga agaagcgata  93000
tgttcaatct caacaaagtc ttttgagacg ctattgcgaa gggccaaatt ccacttactt  93060
aatacgcgag cattgtgtgc cagctctgcg ttttctttaa ggcgtccatt ggcttcaagc  93120
cagttcgcca catcagccca atcccatagc ggggactgtc cctggattct ctggataggg  93180
caagggaagt cgccaccacc acgaagccca tctttaagca tggtaattgc ttgtcgggac  93240
atgcccgtca tttcagctac atcgctcagg ccaactaagg ccgagtcgac tgattctaca  93300
atcgcgccga taccggcaga ttcgatattg tcgaccgctg atgcaatggc tgcatccagc  93360
gatttggctt cgcggtcgaa ctcaacatag acggagtttc catatgcgca aacaatcgca  93420
tcgccacagc cgctttcgta cagcgcatct tccaatcctt cggtctcata ggttacgcct  93480
gagagagtca gagtgaagtt ataaagcgcc ataaaacctc tttatctaaa gtgaagtatt  93540
aatgtacctt tggaacaaat ggcggccaaa accgccacta actactattt tttgctcatc  93600
tggtttttga tgcgaccaca ctggtcgacc gcttgcctga tttgcgtggc atggtgctcc  93660
ggtacatctg gagtcgacca tacacttctg tggtgacttg tatgttcacc tgatttatcg  93720
ccgcagcgca gcttgcagaa gcaatgtgct gacttacctg ctggaaccca aacccagcct  93780
ttactcaacg cgtattcaat ggcctcttga atatgcttat tcggatgtga tttcattttc  93840
ctccgatgtc attatgatag gtatagtgtg agcgcgtgtc aacactgtct attttctgac  93900
gtctacggcc gcagaaaacg gctatagatt atcagaacac tccctgtttt catcaactta  93960
ccgaccccac cccctaactt cttccttcta taagctccat ccttcatttc tttcatggta  94020
aaattgatat atagaaataa gctggaacat atcaaaatga gtgcagatat ctacgaaaaa  94080
```

-continued atcatgtccg atctggagtt cgaccgcgac aatcttgagg aagtctggcg tcagcaaccg 94140
cgcctgttga tggagtacgg ctctaagctg gcgcgggcag aacgcgaggt cgcagatgca 94200
aaactctccc tcgatgcgat tgaggcaaaa atctactaca atgagcgtaa gaacctgagt 94260
atgaacggca ttaagttcaa tgaatccgta ctggaggcga aggttagaac caacccgcaa 94320
tacctcgcaa agcgccagaa actcgatgat gcccggcaca ttgcagatct atacaagcac 94380
gctgtaaccg ccttctctca ccgccgtgac atgattgtcc aggcgtccaa aatggctatc 94440
gtggagattg aacgcttggg cgccgaacgt ttccactcgc cccgttaatt tatcctagat 94500
gataagtaag tactgatcta ttatccttct cgctcgaaag agccacgaat aaacgaatgc 94560
ccaacgcgca tagcgccaat ggccacaatc acaaaaagga gaaatacatg tctaagtcat 94620
tacttgatct gcttaacaag acccgtggcg atattgcttc taaacgtggc aataacgttg 94680
atttgacccg tctgaaagac ggcaataact atctgcgcat ttttccgaac aaggacgacc 94740
cgaatggtgt gttcttccag actttcggta tgcactacgt taagcatcag aatgaggaag 94800
gcaaagatgt aaccaccgcc tacatctgcg aacagcacac ccacggccac gcttgccagc 94860
tgtgtgagat ggttatggaa ggtcgtgctc gctttaaggg caacaaagcg atggaagagc 94920
gcattaacag tatgcgtgct acaccgcgtt atctggtcaa tggtgttctg tctgcgcgag 94980
aagactttgc agacgcagag aaatgccagt tgattgagct gccgtctacg gtcttcgacg 95040
atatctgcaa agtgatgtcc gaagatattg ctgatgatat cggcaaccca ctgagcaaag 95100
aagaaggcta tgcgttcctg attaagcgta ccggttccgg tcgtgacacc aagtatgacg 95160
tatccccgaa acgtaaagtc tacaaaggcg acattcctga gaagctctgg actacccaac 95220
acgatctgat cgcatacgcg aaccaggctg acgaaacccg tctgctgtct acggctcgca 95280
ctatgggtcg tctgattggt attgcggctc cggcagcaac aatgtcctct ccggccattt 95340
cttccgctgc aaaatcagct gctgctgaac tgccaggctt tggctctatc actggtcata 95400
cggaaggcgc agctgctgtc gctacagcac acacaccggc tccagagtcc accagcctgg 95460
ttgatgaaga gatcctgcgt gccgctgaag ctgagttcaa accggaaact aaaccggaaa 95520
aggttaaagc tccggaagcc gccgcagctg caagtgcttc cgcatctgct gccgctgcat 95580
ctgtaccagc tgacgaaggt ctcgatgacc tgctggctga actggacgct ctgtaatccc 95640
ataacgtgac cagtaaggcg tctacggacg ccttactttt tggaaggagt gtaccggtga 95700
attatctctt tgtggacggt aacagcctgg gctattacca ccagcaatcc gacaaattac 95760
acaacggcga gatggaagtt caggcggctt ttggcttcgt gaagaacgtt cgtcgttacg 95820
cctcaattct ccatgcccgc ccaatgatct tgtgggatgg attcagcgac aaacgtcgcg 95880
acttctaccc ggagtacaaa gcgaatcgcg atgacgaccc ggatatgaag aagatgaaag 95940
aaggttttgc catccagaag ccgtacatct tgaaaatgat gaccgcgctg ggcgttaacc 96000
aactcattgc aaaggatgca gaagcggacg acctggcagg aatgctggtc tctcgcctgg 96060
ctccgcagcc gaccgttgat catatctacc tgctgactgg cgatggcgac tggcttcagc 96120
tggttcgcga gaatgtgagc tgggtaagcc tgcgtgaaga tgccaagcac aagcaggtga 96180
acttcgaaca gttcgcagag ctgaccggtc tgccgacgcc acgcgcgttt ctggaagcga 96240
aagcgttgca gggcgatacc tcggacaaca tcaaaggcgt aggtggcatt ggtgatggtg 96300
gcgcgaaaga gctgcttcat gaatggggaa gtgtggccgc aatggtacgc ggcattaacg 96360
acggctccat tgtcatcaac aaaggtcgct ataagacggc attcaacaag ctggcaaaga 96420
acgccttcaa cgagaagaca ggctgccgga tgctcgaagc ctttaagcgc aacatgatgc 96480

-continued

```
tgatgaacct tatcgacaca aaattcccac ccagcgaaat cgagtcgatt aaaggcgcac  96540
gcgacatgaa cgccttcgaa cagatgtgtt gcgagctgaa tttccggtcg tttctggaag  96600
atctggaagt gtttgttctg ccatttgaga ggtactgctg atgctgaaat ccatcattaa  96660
tggcggggca actacgccaa ccatgctggc taaagagatt gtcttctgcc acggcgaaca  96720
cgctgtggtg gcgctgccga acattctggg cgctgctggc atttctgcta ctgagcgtga  96780
gttcgcgctg gtcagcgagc aggtcgtgaa gatcatcgct cgcgtcgcca aacacctgaa  96840
ccacgacgca atcaagtttg acgaagccgc agcttcgaag cgaatcaacg aatcaaaagg  96900
agcctaatca tggcaaaagg caaatccgca ctggcactgg cgctgaaaaa gaaaatcggc  96960
agcaatgacg agattcagaa ggtctcccac tggattgact ccggtttccc tccactgaac  97020
aaagccattt ccggacgtta cgacggtggt tttccgtgtg ggcgtatcgt tgaagtcttc  97080
gggccaccaa gcgccggtaa aaccttttg gcgacggctg cgatggtatc agcacagaaa  97140
caggatggtc tggccgtatt ccttgaccac gaaaacagct tcgacgttgg tcttgcggtg  97200
gcgaatggct tgaacgccga cgaagacgac ggtcagtggg tctacaaaca gccggatacc  97260
ttcgaagact ccgttgagct gatcggcaca atcctcaagc tggtgcgcga cgaagagctt  97320
atcccggaaa cagcccctat ctgcatcgtt gccgactctc tggcgtcgat ggtaccgaac  97380
tcgaaagctg agaagttcga caagatggca gaaggcactg cgaaggacaa agatcagctg  97440
aacatgaacg acaacacggc gctggcgcgc gcgacgagtg cgaacttccc tactctggcg  97500
ctttgggcgc gtaagtacaa cgcgtgcatt atcttcttaa accaggtgcg taccaaaatt  97560
ggcgtgatgt ttggcgatcc gactacgtct ccgggcggcg actctccgaa gttctacgcg  97620
tcggtgcgca tccgtctggg agcatccgtc atgaaggatg gcaaagagaa gatcggacag  97680
gacgttggcg ccgagtgcat taaaaacaaa gtcgcgcctc cgtttggtaa atgctcatgg  97740
aaattctact tcgacccgac tcgcgggctg gacgtcatcg aatctctggt tgagtacatg  97800
ctggaagaag gatacctgcc aaagaacgcc agcgggcgtg tggaaattag cgataagaga  97860
tataccaaat cgcagatcgt cgagatgtac cgcgagaagc cactcccgga aatcatcgca  97920
gcactccagg cgatagacga acggcgagcg aaagagtcgt ccccagcaga gacagaagaa  97980
gcgtaatcac aaggcgccca ttgggcgcct ttttatactt gaaaatatat aagtacttac  98040
ttattatttc tgcaccaaaa cgacaaaagg aaacacatga ttaagggtta tctcatggct  98100
gtttcagcgg tggtgtcagt ctgctttatc tacggtttac tggttccatc gcttatctca  98160
gctaaaagcg atctggcctt ctttatcgga cttgccatcg ctgtagtctt cccggttgcc  98220
ttgttaaaag ctggccgcag gtatatcaac tcactcaata aaactaagga gaagtaagta  98280
atgaagaaag gtttactggc ggtgactttg gctgctattt gcacaatggg tctgaccggc  98340
tgcgatcgcg tggaaccggg atacgttggc attaaggtaa acaaattggg tgaagacaaa  98400
ggtatcggtg aagttgtcgg cgttggccgt cagtggactg gtctgaatac cgagctgtac  98460
accttcccca ctttcaaaca gatgaaaacc tacgatgagc cgttcacatt ccagatgagc  98520
gacggtacag ccatcggcca caaaattggt gtggcatatc tggttaatcg caacaaagta  98580
actaccgtat tccagaccta tcgcaaaggt gttgacgaca ttaccgacac tgatctgcgc  98640
cagaagattg cggattcact gaaccgtctg gccagccgca tgactaccga cacgttcatc  98700
gacggtggca aggcgtctct gctcgacaat gcgttgaaag acattcaggc agaaatgtca  98760
ccggtaggta ttgaggttat tagcctgtca tgggtgggca aaccagacta cccggacacg  98820
```

-continued

```
gtcatcgaat ctatcaatgc caaagtgacc gcgaaccaga aaacgctcca gcgccagcag  98880

gaagttgagc agcgcaaggc agaagcgaac atgctgcgtg aacaagccga aggtgaagcc  98940

gacgctatcc gcaaacgtgc tcaagcagaa gctgacgcca tcaagttgcg cggtgaagca  99000

ttacgtcaga acccgaacgt catggagctg gaagccatca acaaatggaa tggccagttg  99060

cctcagtaca tgactgaagg ggctaatact ccgtttatcg cgttgaagta acaccctttt  99120

caaagatacg gcgtccactt ggacgccttt tttatttccg tattatcacc aacaagaaaa  99180

caaattggtt actaatacgg aattaacttc cgttgaagta aaaagtgaca acgccacgca  99240

atttctgaaa gaaggagatg atgaatgaaa aactacgctg aaatgacgga ctttgagatt  99300

aactgcctgg tcgcggaagc aaccggccat cgccccctca tctcacaata tggctggaaa  99360

ggctcacaag ttggagatta cacaaaagtg attgcgattg ggccaaacgg agcgggttct  99420

ttcgactggt gcaacaatcc ggtagatgcc tgggacatca tttccagaaa cagaatcggc  99480

atcattccag ccagacaggc tggcgagtgg agagcggccc acaggctggt ggatagctca  99540

acaccacaac atctgatcca gaaccctaac cctttcagag cggcaatgat cgtgtttctt  99600

ttgatgcagg agaaaaaacg tgaaaaaact gtatgacgcg gccaacgctg cgctggatgt  99660

agtggatacc gaaattgccc agggcttccc ggagccagaa tgggcgacgc agctgcgtga  99720

ggcgattgca gagatgaacg caccggaacc ttcagaagat gaagccgact ggcagcgttt  99780

catcagaatg tacgcggaag agattggccc gacgccaacc gctgaacagg ccatgctgct  99840

caagtacttc aaggaggctg gggagaatct gccggttgat gacacaccgc actggtttca  99900

cgccgcctgg cgtaagttcg acgtgatcta cacccgcgat ctgggaagta aagatatggt  99960

cgtctggcat ctgatgcaca ttgataaggc tgtcgaccgc acgctggaga agttctttcc 100020

accagcctga acacaatgat tgtgtaccgc atggcgcaca ttagtataaa taagtactta 100080

ccaacaagga gaagcacatg aagattttgg ttcgcatttc atcaagcacc gactatgacg 100140

tttatccgtt gttcatggtc aagtgcgacg gtctgaacga tgaagaaatc caagcggcaa 100200

ttgagcgcaa tctcgttgag tatactggta tggatgcgga ttctgtgcat gtcgatgatg 100260

acggtgtttg ttggagcaat ggtagttgtt ggtatgtaga cgacacgacg ccggtaagcg 100320

atgaagacgc tgctcacctt gagcgtattt taggcatcag cacttttgag tgatatttac 100380

agcaaataat atataagtta gtatttacct atcatgaaaa ccgtattaga caccttatta 100440

cttattatct cgatagcttt tgtgctcgat tgcatcttca ccggagtaat ccataaagcg 100500

ctggcgcctg ttaatagcgc gatgattaat gcgctggccg tagtgctgtt attcgactca 100560

gcattcggcg ttatccaagg agtcgtggca tgaagaaaac agccctggct ctggcactgt 100620

tcactctccc tgtctacgcg aacacacatg tctatgagtg tgaaatgtct gtggccgaag 100680

tgaaaaacga cgagatctgc aacgtcgtca aagctaacta cggcgcgatg attgtggaca 100740

gcggcgaaca gttttatgtc gtgcgcgatg atcgcgtcct gtcttcaccc tatctcacca 100800

gacgtaacgg caaactgtct ggcgtgggtg aagataagtt cgtttacgac aaatcaggtg 100860

atgtttacgg cgttcacgcg aagaacgcca gctacctttt cgatgactgc aaggaggttg 100920

gttgatggcg gttacaatgg caggtcttga aatcgaaaaa acaagcggct actggcgtgc 100980

caaagggttt                                                        100990
```

<210> SEQ ID NO 3
<211> LENGTH: 9960
<212> TYPE: DNA
<213> ORGANISM: Yersinia pestis -continued

<400> SEQUENCE: 3

```
tggcgtgatg atggaactgc aacatcaacg actgatggcg ctcgccgggc agttgcaact     60
ggaaagcctt ataagcgcag cgcctgcgct gtcacaacag gcagtagacc aggaatggag    120
ttatatggac ttcctggagc atctgcttca tgaagaaaaa ctggcacgtc atcaacgtaa    180
acaggcgatg tatacccgaa tggcagcctt cccggcggtg aaaacgttcg aagagtatga    240
cttcacattc gccaccggag caccgcagaa gcaactccag tcgttacgct cactcagctt    300
catagaacgt aatgaaaata tcgtattact ggggccatca ggtgtgggga aaacccatct    360
ggcaatagcg atgggctatg aagcagtccg tgcaggtatc aaagttcgct tcacaacagc    420
agcagatctg ttacttcagt tatctacggc acaacgtcag ggccgttata aaacgacgct    480
tcagcgtgga gtaatggccc cccgcctgct catcattgat gaaataggct atctgccgtt    540
cagtcaggaa gaagcaaagc tgttcttcca ggtcatcgct aaacgttacg aaaagagcgc    600
aatgatcctg acatccaatc tgccgttcgg gcagtgggat caaacgttcg ccggtgatgc    660
agcactgacc tcagcgatgc tggaccgtat cttacaccac tcacatgtcg ttcaaatcaa    720
aggagaaagc tatcgactca gacagaaacg aaaggccggg gttatagcag aagctaatcc    780
tgagtaaaac ggtggatcaa tattgggccg ttggtggaga tataagtgga tcacttttca    840
tccgtcgttg acaccctgat gaattcacgt gttcacgcct gaataacaag aatgccggag    900
atacgcagtc atatttttta cacaattctc taatcccgac aaggtcgtag gtcgttatag    960
gaaaattctt agcaccattc cggaacaatc agaacagcag gccatgaacg actgacaaca   1020
ttacgaatat aaaaaacgca cccgggccag acattccccc tactgattaa accagccgga   1080
cttgtccacg gaacggtctt tttaaaccga cacacagtct gagtacagat acatgtcacg   1140
atgatgcagg attagcggaa gagtgtgagc acgtttccgg gaactgtggt gaaccatagc   1200
tcaatattcg agtgagggca taccggaaac gcgctcagat tcgttgtaac gcgattttcc   1260
gtaccgggca attttttcag ttgttttttc gtttcatgtc gtcagaaacg ttctgagcgc   1320
gtttccggca tctgatgcta cgcaaaccat ccccatggtc agttgacagc cggaaacacg   1380
cgggtgtcgt tttagcgtat cgacgggacg gcgtcgagaa gcacaaaaaa cagatgttgt   1440
actcagtcag ttgttttaca gacagcactg cggcagattg aaaaagtacc gtactttcag   1500
gaatgtccag aaaccatgtg tcagacttcg ttctccccct tccgggtgaa tttttttgtc   1560
atccgttcag gaatctcttt ataacgatta ctccatttca ggattttttta tgtggcgttt  1620
actacaggca ggatattcaa aggcaaaaaa atccccccgga acaggcggaa cccggacagg  1680
gggagaacga atcgctaaat aattttcgta gttgtatttc ccatcgttgc tactgcaacg   1740
ggatgaattt gccgcagttt atcctgtaaa acaatcctga tttactcaca ctccacatat   1800
cactgacgga gcacaacgga atagtgaaca aacaacaaca aactgcgctg aatatggcgc   1860
gatttatcag aagccagagc ctgatactgc ttgaaaaact ggatgctctg gatgccgacg   1920
agcaggcggc catgtgtgaa cgactgcacg aactcgcgga agaactccag aacagcatcc   1980
aggctcgctt tgaagccgaa agtgaaacag gaacataacg aagctcccgg agacggtcac   2040
agcttgtctg tgaacggatg ccgggagcag acaagcccgt cagggcgcgt cagcgggttt   2100
tagcgggtgt cggggcgcag ccatgaccca gtcacgtagc gatagcggag tgtatactgg   2160
cttagtcatg cggcatcagt gcggattgta tgaaaagtgc accatgtacg gtgtgaaatg   2220
ccgcacagat gcgtaaggag aacatgcaga tgccgatgct cttccgcttc ctcgctcact   2280
```

-continued

```
gactcgctgc gctcggtcgt tcggctgcgg cgagcggtgt ctgctcactc aaaagcggtg   2340
atactgttat ccacacaatc aggggataac gccggaaaga acatgtgagc aaaaaacgaa   2400
gaccccagaa aaggccgcgc cggaggcgct ttttccatag gctccgcccc cctgacgagc   2460
atcacaaaaa tcgacgctca agtcagaggt ggcgaaaccc gacaggactt aaagatacca   2520
ggcgtttccc cccggaagct ccctcgtgcg ctctcctgtt ccgaccctgc cgcttaccgg   2580
atacctctcc gcctttctcc cttcgggaag cgtggcgctt tctcatagct cacgctgttg   2640
gtatctcagt tcggtgtagg tcgttcgctc caagctgggc tgtgtgcacg aaccccccgt   2700
tcagcccgac cactgcgcct tatccggtaa ctatcgtctt gagtccaacc cggtaagaca   2760
cgactttacg ccactggcag cagccattgg taactgaaaa gtggatttag atacgcagaa   2820
ctcttgaagt tgaagcctta tcgcggctac actgaaagga cagcatttgg tatctgtgct   2880
ccacttaagc cagctaccac aggttagaaa gcctgagaaa cttctaacct tcgaaagaac   2940
ccacgcctga gaacgtgggt tttttcgttt acaggcagca gattacgcgc agaaaaaaag   3000
gatctcaaga agatcctttg atcttttcta ctgaattgcg ctcccgatca gttcagcaga   3060
agattatgat ggggttctat gggtattgct gcggtaacac ccatgttact tgaggttgta   3120
tgtagtctgt gtagaattat acacataagg cttaaactgc tcttttttt caatatgcaa   3180
ttggaagttc attgactaca taaatagatt attccaaata atttatttat gtaagaacag   3240
gatgggaggg ggaatgatct caaagttatt ttgcttggct ctcatatttt tatcatcaag   3300
tggccttgca gaaaaaaaca catatacagc aaaagacatc ttgcaaaacc tagaattaaa   3360
tacctttggc aattcattgt ctcatggcat ctatgggaaa cagacaacct tcaagcaaac   3420
cgagtttaca aatattaaaa gcaacaccaa aaaacacatt gcacttatca ataaagacaa   3480
ctcatggatg atatcattaa aaatactagg aattaagaga gatgagtata ctgtctgttt   3540
tgaagatttc tctctaataa gaccgccaac atatgtagcc atacatcctc tacttataaa   3600
aaaagtaaaa tctggaaact ttatagtagt gaaagaaata aagaaatcta tccctggttg   3660
cactgtatat tatcattaat agcaagcccc tcattattat gaggggctca tggttatttt   3720
aacaatccac tatcgatatc tttttgcacc agagcgccct ctcgtttacg tctgtcagac   3780
attccatcaa caatattatt aaaagcattt acaaggccat tccagtcttt tgcgataact   3840
ttattccata ctgtgggagc agttctggat aacttaaacc ctttttgata tccaatagac   3900
accagtgctg tacgggttct caacggtaaa tcgctgaacc gaagaccgat attagcgtca   3960
ttgaaaagac cttcaatctt atgtgagaat ttatcaatat aaatattaga taagagatga   4020
gcttcattat cagaaagcgt cagaggtgct gttctcactt tatcataagc ctccttccct   4080
cgaagcatat aatacccatc aagtctatct gcaatatact gagggacacc gtcattcaat   4140
aaatcctgtt tgcttcgctg accaaggtca accccggaac cgaatgtaac accggtactg   4200
ttaaaataat cgctactagg attagacgga aaatgacttg tcggattaaa cccttcaaaa   4260
ccattactgg agaaaatatc gtggtcaaca atatttaccg aacgacgtaa aaattccttc   4320
agttgactaa tattgtcaaa gttaatgaca gtgttgtccg ctaggacgat gcgatttcgg   4380
ttattattca gaatgtcttc gttctctttc twatcgagat gttcaataga ttcggcaatc   4440
gttccctcaa gaaccatgac acggtagact ttcacaccgt ctttttcctg acctgtttca   4500
acagttattt tctgttcgta agacacggtc ccttcagttt ttgaaatttt actttcctgg   4560
cggatcttat ttgaatattc actgtctttc tccatctccg tatcaatcgg aaaccccata   4620
atgtacatca gtttaaaatt actccggcca ggcagatcca cataatgtgg taatgcaatt   4680
```

-continued

```
gtaatcgaat tagcttcaaa atttggtctg taactgctta atgtacttcc ggaaaagaga   4740
aaagccggaa caccacctga accattcact accattgtat ctgacataaa aattcctctt   4800
taacacataa aaaaacaata agttaaaaaa aaatactgta cataaaacca ctgtttttat   4860
gtacagtaat aaaattacgc cgctttattt tctctgtcaa taatatgaaa tttcattttt   4920
gtgatctgaa tcactcttat aaaaatcagg aagggaagat tcgcagcaga aaaacagcac   4980
cgggtaacat cagaaaaaaa cagaaaggag ataacgtgag caaaacaaaa tctggtcgcc   5040
accgactgag caaaacagac aaacgcctgc tggctgcact tgtcgttgcc ggatacgaag   5100
aacggacagc ccgtgacctc atccagaaac acgtttacac actgacacag gccgacctgc   5160
gccatctggt cagtgaaatc agtaacggtg tgggacagtc acaggcctac gatgcgattt   5220
accaggcgag acgcattcgt ctcgcccgta aatacctgag cggaaaaaaa ccggaagggg   5280
tggaaccccg ggaagggcag gaacgggaag atttaccata actcccgtta tcagtaccat   5340
cggctcaacg ctcgttgtcg gatctgaaaa attcgctcaa aagatcatat ttccctggat   5400
attttccacc gtttcttatg tgagcaaagt cacataattc tgtcagacga cgagaaaacg   5460
gatatcgatt attgtttaat atttttacat tattaaaaat gaaattagat aatcagatac   5520
aaataatatg ttttcgttca tgcagagaga ttaagggtgt ctaatgaaga aaagttctat   5580
tgtggcaacc attataacta ttctgtccgg gagtgctaat gcagcatcat ctcagttaat   5640
accaaatata tcccctgaca gctttacagt tgcagcctcc accgggatgc tgagtggaaa   5700
gtctcatgaa atgctttatg acgcagaaac aggaagaaag atcagccagt tagactggaa   5760
gatcaaaaat gtcgctatcc tgaaaggtga tatatcctgg gatccatact catttctgac   5820
cctgaatgcc aggggggtgga cgtctctggc ttccgggtca ggtaatatgg atgactacga   5880
ctggatgaat gaaaatcaat ctgagtggac agatcactca tctcatcctg ctacaaatgt   5940
taatcatgcc aatgaatatg acctcaatgt gaaaggctgg ttactccagg atgagaatta   6000
taaagcaggt ataacagcag gatatcagga aacacgtttc agttggacag ctacaggtgg   6060
ttcatatagt tataataatg gagcttatac cggaaacttc ccgaaaggag tgcgggtaat   6120
aggttataac cagcgctttt ctatgccata tattggactt gcaggccagt atcgcattaa   6180
tgattttgag ttaaatgcat tatttaaatt cagcgactgg gttcgggcac atgataatga   6240
tgagcactat atgagagatc ttactttccg tgagaagaca tccggctcac gttattatgg   6300
taccgtaatt aacgctggat attatgtcac acctaatgcc aaagtctttg cggaatttac   6360
atacagtaaa tatgatgagg gcaaaggagg tactcagacc attgataaga atagtggaga   6420
ttctgtctct attggcggag atgctgccgg tatttccaat aaaaattata ctgtgacggc   6480
gggtctgcaa tatcgcttct gaaaaataca gatcatatct ctcttttcat cctcccctag   6540
cggggaggat gtctgtggaa aggaggttgg tgtttgacca accttcagat gtgtgaaaaa   6600
tcaccttttt caccataatg acggggcgct cattctgttg ttttgccttg acattctcca   6660
cgtctttcag ggcatggaga aggtcaaatt agacatggaa cgctactctc cttcctgtag   6720
gaagctcaac atccaagctt aatttgcctc ccattgcttc aacgtaacgc tttaacgtcg   6780
ccagctttaa atcatttccg cgctgctcca gctttgttac tgctggctgg cttataccca   6840
tcgcctcagc aacttgtttt tgtgataact ggagttcttc acgcatcatc tgcaagccga   6900
cctcaagaat catctcatct gccatttctt taattcgtgt ctggctttca ggtgaacgac   6960
tggcaatcac ctcatctaat gttctcatta cttgctctcc agtgtgttca gatgtgctgt   7020
```

-continued

```
aaattcatcc tcagctatac gcaccagttt ttcataaaac cgcttatcat tacttttatc   7080

tcctgcacaa agaacgatag cccgacgaat cggatcgaac gcataaaagg ctcttatcgg   7140

acggccagaa aactgaacgc gaagctcttt catatttttg taccgagaac ctttcacggt   7200

atcggcatat ggcctgggta actcaggtcc gtaaacctgt agctttttca aatcagccaa   7260

aaccttttcc tgaagagcgt cttcttgctc atttagccag tcgtcaaatc gctggctaaa   7320

aagtaccatc cacatgctca accctataac ctgtagctta ccccactaac aatataacct   7380

acgagttata ttttcaagaa aagctggcta tttaacataa cggcaatttg tacgcaccac   7440

tgaaatgcgt tcagcgcgat cacggcaaca gacaggcaaa aatagcaaca aacctcccga   7500

aaaaccgccg cgatcgcgcc tgataaattt taaccttatg catatctatg cagccaggcg   7560

aatcacgaac gaattgcctg cctgatgtaa ctgaaacggg tgtttttttcc tgatttggtg   7620

ggcgtggaag acggaacatg aacgggaaaa cagaattcat gccagatgag cgcgatctgg   7680

caattaaggc aaaacacagc aacaaagaca cgccagaatc gcgcccggat atgttttaac   7740

gcgattttca gactcagaca aattcagcag aatgctactc cattcaccgg gctgatggtg   7800

aatacatgcg tatccaggat gagtacattt ctggctctgc cacagctctg tctgttggca   7860

gctttcgcct gtccggaaac ctgcttaaaa cgctcccgaa aggcctctga accagaaagc   7920

aacaaaacac aggccattaa gtaaatcgcg ttaaaacacg tctgatggat tgctgcaaaa   7980

aaaagtccct aatggagcag ggactgttaa acccagtgaa tagcgtctaa attaaagtaa   8040

gaatacgacc aggtactctt cagaaaagag attaatccac cgcacagaat aatcaacagt   8100

aaaaacaaac aaccctgatt ttttattttt cttttttttcg ataaaaacaa aattaaagaa   8160

ataattaatc agaacattcc ttaacttcag ggcattgcct gtgttccatt ttgtgattag   8220

tctgaaactt ccgaaggtgg ataacacccg gtattttttt gctcacataa agcccctcct   8280

tcaggcagag ggcttttttc tttgccacca cataaaaaag gccctcacag gaggtgttct   8340

gtgagggcgt atgataagga ctgaatcgat ggttaatatg tctagtcctg acttttgcat   8400

ctccgaatat aaaaccctgt ttaacggcat gcaaaaccaa aaaataaaaa tgtgacatcg   8460

caatgccaga taatattgac gcatgaggga atgcgtaccc cgacccctgt gtaacgaacg   8520

gtgcaatagt gatccacacc caacgcctga aatcagatcc agggggtaat ctgctctcct   8580

gattcaggag agtttatggt cacttttgag acagttatgg aaattaaaat cctgcacaag   8640

cagggaatga gtagccgggc gattgccaga gaactgggga tctcccgcaa taccgttaaa   8700

cgttatttgc aggcaaaatc tgagccgcca aaatatacgc cgcgacctgc tgttgcttca   8760

ctcctggatg aataccggga ttatattcgt caacgcatcg ccgatgctca tccttacaaa   8820

atcccggcaa cggtaatcgc tcgcgagatc agagaccagg gatatcgtgg cggaatgacc   8880

attctcaggg cattcattcg ttctctctcg gttcctcagg agcaggagcc tgccgttcgg   8940

ttcgaaactg aacccggacg acagatgcag gttgactggg gcactatgcg taatggtcgc   9000

tcaccgcttc acgtgttcgt tgctgttctc ggatacagcc gaatgctgta catcgaattc   9060

actgacaata tgcgttatga cacgctggag acctgccatc gtaatgcgtt ccgcttcttt   9120

ggtggtgtgc cgcgcgaagt gttgtatgac aatatgaaaa ctgtggttct gcaacgtgac   9180

gcatatcaga ccggtcagca ccggttccat ccttcgctgt ggcagttcgg caaggagatg   9240

ggcttctctc cccgactgtg tcgcccccttc agggcacaga ctaaaggtaa ggtggaacgg   9300

atggtgcagt acacccgtaa cagtttttac atcccactaa tgactcgcct gcgcccgatg   9360

gggatcactg tcgatgttga aacagccaac cgccacggtc tgcgctggct gcacgatgtc   9420
```

-continued

```
gctaaccaac gaaagcatga aacaatccag gcccgtccct gcgatcgctg gctcgaagag   9480
cagcagtcca tgctggcact gcctccggag aaaaaagagt atgacgtgca tcttgatgaa   9540
aatctggtga acttcgacaa acaccccctg catcatccac tctccatcta cgactcattc   9600
tgcagaggag tggcgtgatg atggaactgc aacatcaacg actgatggcg ctcgccgggc   9660
agttgcaact ggaaagcctt ataagcgcag cgcctgcgct gtcacaacag gcagtagacc   9720
aggaatggag ttatatggac ttcctggagc atctgcttca tgaagaaaaa ctggcacgtc   9780
atcaacgtaa acaggcgatg tatacccgaa tggcagcctt cccggcggtg aaaacgttcg   9840
aagagtatga cttcacattc gccaccggag caccgcagaa gcaactccag tcgttacgct   9900
cactcagctt catagaacgt aatgaaaata tcgtattcac tggggccatt caggtgtggg   9960
```